(12) United States Patent
Manwaring et al.

(10) Patent No.: US 9,078,655 B2
(45) Date of Patent: Jul. 14, 2015

(54) HEATED BALLOON CATHETER

(75) Inventors: Kim Manwaring, Phoenix, AZ (US);
David McNally, Salt Lake City, UT (US)

(73) Assignee: Domain Surgical, Inc., Salt Lake City, UT (US)

( * ) Notice: Subject to any disclaimer, the term of this patent is extended or adjusted under 35 U.S.C. 154(b) by 975 days.

(21) Appl. No.: 13/224,254

(22) Filed: Sep. 1, 2011

(65) Prior Publication Data

US 2012/0071712 A1 Mar. 22, 2012

Related U.S. Application Data

(63) Continuation-in-part of application No. 12/647,358, filed on Dec. 24, 2009, now Pat. No. 8,506,561.

(60) Provisional application No. 61/170,203, filed on Apr. 17, 2009, provisional application No. 61/170,220, (Continued)

(51) Int. Cl.
*A61B 18/04* (2006.01)
*A61B 18/10* (2006.01)
(Continued)

(52) U.S. Cl.
CPC .............. *A61B 18/10* (2013.01); *A61B 18/082* (2013.01); *A61B 17/285* (2013.01);
(Continued)

(58) Field of Classification Search
CPC ............. A61B 1/07; A61B 17/320068; A61B 17/320092; A61B 18/04; A61B 18/18; A61B 2002/2864; A61B 2017/00106; A61B 2017/0011; A61B 2017/320072; A61B 2018/00089; A61B 2018/00095; A61B 2018/00601; A61B 2018/00876; A61B 2018/1407; A61B 2018/141; A61B 2018/144; A61B 2018/1465; A61F 2002/2864; A61F 2002/4651; A61F 7/123; A61F 9/0079; A61M 2205/368; A61M 2205/3693; A61N 1/40; A61N 1/403; A61N 2/02
USPC .................................... 606/47, 113; 607/103
See application file for complete search history.

(56) References Cited

U.S. PATENT DOCUMENTS 300,155 A 6/1884 Starr
770,368 A 9/1904 Heath
(Continued)

FOREIGN PATENT DOCUMENTS

EP 0033958 8/1981
EP 0 130 671 9/1985
(Continued)

OTHER PUBLICATIONS

Center for Research in Scientific Computation. *A Domain Wall Theory for Ferroelectric Hysteresis*, Jan. 1999.
(Continued)

*Primary Examiner* — Jaymi Della
(74) *Attorney, Agent, or Firm* — Snow, Christensen & Martineau; Randall B. Bateman; Christopher L. Wight

(57) ABSTRACT

Thermally adjustable surgical tools include a conductor and a ferromagnetic material. The ferromagnetic material may be quickly heated when subjected to high frequency alternating current through the conductor. The ferromagnetic material may also cool rapidly because of its relatively low mass and the small thermal mass of the conductor. The thermally adjustable surgical tools may be used to sculpt, melt, break and/or remove biological material. The thermally adjustable surgical tools may also include balloon catheters which can heat fluid to thereby treat biological material.

27 Claims, 38 Drawing Sheets

Related U.S. Application Data filed on Apr. 17, 2009, provisional application No. 61/170,207, filed on Apr. 17, 2009, provisional application No. 61/380,179, filed on Sep. 3, 2010, provisional application No. 61/473,715, filed on Apr. 8, 2011.

(51) Int. Cl.
  *A61B 18/08* (2006.01)
  *A61B 17/285* (2006.01)
  *A61B 17/42* (2006.01)
  *A61B 18/00* (2006.01)
  *A61B 18/14* (2006.01)

(52) U.S. Cl.
  CPC *A61B 2017/4216* (2013.01); *A61B 2018/0022* (2013.01); *A61B 2018/00107* (2013.01); *A61B 2018/00422* (2013.01); *A61B 2018/00559* (2013.01); *A61B 2018/00642* (2013.01); *A61B 2018/00791* (2013.01); *A61B 2018/00815* (2013.01); *A61B 2018/00821* (2013.01); *A61B 2018/046* (2013.01); *A61B 2018/141* (2013.01); *A61B 2018/1412* (2013.01); *A61B 2218/002* (2013.01); *A61B 2218/007* (2013.01)

(56) References Cited

U.S. PATENT DOCUMENTS

| | | | |
|---|---|---|---|
| 1,104,053 | A | 7/1914 | Lea |
| 1,280,052 | A | 9/1918 | Lidberg |
| 1,335,987 | A | 4/1920 | Reid |
| 1,366,231 | A | 1/1921 | Winter et al. |
| 1,401,104 | A | 12/1921 | Kruesheld |
| 1,794,296 | A | 2/1931 | Hyams |
| 2,027,854 | A | 1/1936 | Breth et al. |
| 2,050,904 | A | 8/1936 | Trice |
| 2,120,598 | A | 6/1938 | Beuoy |
| 2,250,602 | A | 7/1941 | Pierce |
| 2,278,633 | A | 4/1942 | Bagnall |
| 2,375,154 | A | 5/1945 | Volterra |
| 2,412,977 | A | 12/1946 | Eskin |
| 2,501,499 | A | 3/1950 | Crowley |
| 2,670,425 | A | 12/1954 | Stone |
| 2,735,797 | A | 2/1956 | Schjeldahl |
| 2,782,290 | A | 2/1957 | Lannan et al. |
| 2,831,242 | A | 4/1958 | Kieffer et al. |
| 2,846,560 | A | 8/1958 | Jacoby et al. |
| 2,863,036 | A | 12/1958 | Mitchell et al. |
| 2,947,345 | A | 8/1960 | Schjeldahl |
| 2,960,592 | A | 11/1960 | Pierce |
| 3,084,242 | A | 4/1963 | Vogler et al. |
| 3,213,259 | A | 10/1965 | Bennet et al. |
| 3,350,544 | A | 10/1967 | Lennox |
| 3,352,011 | A | 11/1967 | Alexander et al. |
| 3,400,252 | A | 9/1968 | Hayakawa |
| 3,404,202 | A | 10/1968 | Carlson et al. |
| 3,413,442 | A | 11/1968 | Buiting et al. |
| 3,414,705 | A | 12/1968 | Marcoux |
| 3,434,476 | A | 3/1969 | Shaw et al. |
| 3,501,619 | A | 3/1970 | Buiting et al. |
| 3,515,837 | A | 6/1970 | Ando |
| 3,520,043 | A | 7/1970 | Darling |
| 3,556,953 | A | 1/1971 | Schulz |
| 3,768,482 | A | 10/1973 | Shaw |
| 3,825,004 | A | 7/1974 | Durden, III |
| 3,826,263 | A | 7/1974 | Cage et al. |
| 3,834,392 | A | 9/1974 | Lampman et al. |
| 3,978,312 | A | 8/1976 | Barton et al. |
| RE29,088 | E | 12/1976 | Shaw |
| 4,089,336 | A | 5/1978 | Cage et al. |
| 4,091,813 | A | 5/1978 | Shaw et al. |
| RE30,190 | E | 1/1980 | Shaw |
| 4,185,632 | A | 1/1980 | Shaw |
| 4,196,734 | A | 4/1980 | Harris |
| 4,198,957 | A | 4/1980 | Cage et al. |
| 4,206,759 | A | 6/1980 | Shaw |
| 4,207,896 | A | 6/1980 | Shaw |
| 4,209,017 | A | 6/1980 | Shaw |
| 4,256,945 | A | 3/1981 | Carter et al. |
| 4,359,052 | A | 11/1982 | Staub |
| 4,364,390 | A | 12/1982 | Shaw |
| 4,371,861 | A | 2/1983 | Abdelrahman et al. |
| 4,374,517 | A | 2/1983 | Hagiwara |
| RE31,723 | E | 11/1984 | Shaw |
| 4,481,057 | A | 11/1984 | Beard |
| 4,485,810 | A | 12/1984 | Beard |
| 4,492,231 | A | 1/1985 | Auth |
| 4,493,320 | A | 1/1985 | Treat |
| 4,523,084 | A | 6/1985 | Tamura et al. |
| 4,549,073 | A | 10/1985 | Tamura et al. |
| 4,600,018 | A | 7/1986 | James et al. |
| 4,622,966 | A | 11/1986 | Beard |
| 4,658,819 | A | 4/1987 | Harris et al. |
| 4,658,820 | A | 4/1987 | Klicek |
| 4,701,587 | A | 10/1987 | Carter et al. |
| 4,752,673 | A | 6/1988 | Krumme |
| 4,807,620 | A | 2/1989 | Strul |
| 4,839,501 | A | 6/1989 | Cowell |
| 4,848,337 | A | 7/1989 | Shaw et al. |
| 4,860,745 | A | 8/1989 | Farin et al. |
| 4,877,944 | A | 10/1989 | Cowell et al. |
| 4,914,267 | A | 4/1990 | Derbyshire |
| 4,915,100 | A | 4/1990 | Green |
| 4,927,413 | A | 5/1990 | Hess |
| 4,938,761 | A | 7/1990 | Ensslin |
| 5,003,991 | A | 4/1991 | Takayama et al. |
| 5,047,025 | A | 9/1991 | Taylor et al. |
| 5,053,595 | A | 10/1991 | Derbyshire |
| 5,057,106 | A * | 10/1991 | Kasevich et al. ............... 606/33 |
| 5,071,419 | A | 12/1991 | Rydell et al. |
| 5,087,256 | A | 2/1992 | Taylor et al. |
| 5,087,804 | A | 2/1992 | McGaffigan |
| 5,098,429 | A | 3/1992 | Sterzer |
| 5,107,095 | A | 4/1992 | Derbyshire |
| 5,182,427 | A * | 1/1993 | McGaffigan ............... 219/663 |
| 5,189,271 | A | 2/1993 | Derbyshire |
| 5,197,649 | A | 3/1993 | Bessler et al. |
| 5,203,782 | A | 4/1993 | Gudov et al. |
| 5,209,725 | A * | 5/1993 | Roth ............... 604/508 |
| 5,211,646 | A | 5/1993 | Alperovich et al. |
| 5,217,460 | A | 6/1993 | Knoepfler |
| 5,300,068 | A | 4/1994 | Rosar et al. |
| 5,300,750 | A | 4/1994 | Carter, Jr. et al. |
| 5,308,311 | A | 5/1994 | Eggers et al. |
| 5,318,564 | A | 6/1994 | Eggers |
| 5,364,392 | A | 11/1994 | Warner et al. |
| 5,370,645 | A | 12/1994 | Klicek et al. |
| 5,370,675 | A | 12/1994 | Edwards et al. |
| 5,376,094 | A | 12/1994 | Kline |
| 5,382,247 | A | 1/1995 | Cimino et al. |
| 5,400,267 | A | 3/1995 | Denen et al. |
| 5,411,508 | A | 5/1995 | Bessler et al. |
| 5,423,808 | A | 6/1995 | Edwards et al. |
| 5,425,731 | A | 6/1995 | Daniel et al. |
| 5,445,635 | A | 8/1995 | Denen et al. |
| 5,472,443 | A | 12/1995 | Cordis et al. |
| 5,475,203 | A | 12/1995 | McGaffigan |
| 5,480,397 | A | 1/1996 | Eggers |
| 5,480,398 | A | 1/1996 | Eggers |
| 5,496,312 | A | 3/1996 | Klicek |
| 5,496,314 | A | 3/1996 | Eggers |
| 5,507,743 | A | 4/1996 | Edwards et al. |
| 5,540,679 | A | 7/1996 | Fram et al. |
| 5,540,681 | A | 7/1996 | Strul et al. |
| 5,542,916 | A | 8/1996 | Hirsch et al. |
| 5,571,153 | A * | 11/1996 | Wallsten ............... 607/98 |
| 5,573,533 | A | 11/1996 | Strul |
| 5,593,406 | A | 1/1997 | Eggers et al. |
| 5,595,565 | A | 1/1997 | Treat et al. |
| 5,611,798 | A | 3/1997 | Eggers |
| 5,628,771 | A | 5/1997 | Mizukawa et al. |
| 5,674,219 | A | 10/1997 | Monson et al. |

(56) References Cited

U.S. PATENT DOCUMENTS

| | | | |
|---|---|---|---|
| 5,707,369 | A | 1/1998 | Vaitekunas et al. |
| 5,707,402 | A | 1/1998 | Heim |
| 5,807,392 | A | 9/1998 | Eggers |
| 5,807,393 | A | 9/1998 | Williamson, IV et al. |
| 5,827,269 | A | 10/1998 | Saadat |
| 5,836,874 | A | 11/1998 | Swanson et al. |
| 5,836,943 | A | 11/1998 | Miller, III |
| 5,843,019 | A | 12/1998 | Eggers et al. |
| 5,911,719 | A | 6/1999 | Eggers |
| 5,964,759 | A | 10/1999 | Yamanashi et al. |
| 6,004,316 | A | 12/1999 | Laufer |
| 6,006,755 | A | 12/1999 | Edwards |
| 6,015,415 | A | 1/2000 | Avellanet |
| 6,035,238 | A | 3/2000 | Ingle et al. |
| 6,038,017 | A | 3/2000 | Pinsukanjana et al. |
| 6,039,733 | A | 3/2000 | Buysse et al. |
| 6,066,138 | A | 5/2000 | Sheffer et al. |
| 6,161,048 | A | 12/2000 | Sluijter et al. |
| 6,190,355 | B1 * | 2/2001 | Hastings ................ 604/96.01 |
| 6,190,382 | B1 | 2/2001 | Ormsby et al. |
| 6,210,403 | B1 | 4/2001 | Klicek |
| 6,228,084 | B1 | 5/2001 | Kirwan, Jr. |
| 6,241,723 | B1 | 6/2001 | Heim et al. |
| 6,287,305 | B1 | 9/2001 | Heim et al. |
| 6,290,697 | B1 | 9/2001 | Tu et al. |
| 6,350,262 | B1 | 2/2002 | Ashley |
| 6,358,273 | B1 | 3/2002 | Strul et al. |
| 6,454,781 | B1 | 9/2002 | Witt et al. |
| 6,533,781 | B2 | 3/2003 | Heim et al. |
| 6,602,252 | B2 | 8/2003 | Mollenauer |
| 6,604,003 | B2 | 8/2003 | Fredricks et al. |
| 6,626,901 | B1 | 9/2003 | Treat et al. |
| 6,632,182 | B1 | 10/2003 | Treat |
| 6,692,489 | B1 | 2/2004 | Heim et al. |
| 6,726,683 | B1 | 4/2004 | Shaw |
| 6,821,273 | B2 | 11/2004 | Mollenauer |
| 6,860,880 | B2 | 3/2005 | Treat et al. |
| 6,908,463 | B2 | 6/2005 | Treat et al. |
| 6,911,026 | B1 | 6/2005 | Hall et al. |
| 6,912,911 | B2 | 7/2005 | Oh et al. |
| 6,980,862 | B2 | 12/2005 | Fredricks et al. |
| 6,980,865 | B1 | 12/2005 | Wang et al. |
| 7,011,656 | B2 | 3/2006 | McGaffigan |
| 7,025,065 | B2 | 4/2006 | McGaffigan et al. |
| 7,083,613 | B2 | 8/2006 | Treat |
| 7,112,201 | B2 | 9/2006 | Truckai et al. |
| 7,122,030 | B2 | 10/2006 | Flores et al. |
| 7,164,968 | B2 | 1/2007 | Treat et al. |
| 7,175,621 | B2 | 2/2007 | Heim et al. |
| 7,211,079 | B2 | 5/2007 | Treat |
| 7,211,080 | B2 | 5/2007 | Treat et al. |
| 7,235,073 | B2 | 6/2007 | Levine et al. |
| 7,300,452 | B2 | 11/2007 | Gleich |
| 7,317,275 | B2 | 1/2008 | Treat |
| 7,326,202 | B2 | 2/2008 | McGaffigan |
| 7,329,255 | B2 | 2/2008 | McGaffigan |
| 7,377,919 | B2 | 5/2008 | Heim et al. |
| 7,396,356 | B2 | 7/2008 | Mollenauer |
| 7,435,249 | B2 | 10/2008 | Buysse et al. |
| 7,473,250 | B2 | 1/2009 | Makin et al. |
| 7,473,253 | B2 | 1/2009 | Dycus et al. |
| 7,494,492 | B2 | 2/2009 | Da Silva et al. |
| 7,528,663 | B2 | 5/2009 | Naletov et al. |
| 7,533,719 | B2 | 5/2009 | Hinson |
| 7,540,324 | B2 | 6/2009 | de Rouffignac |
| 7,549,470 | B2 | 6/2009 | Vinegar |
| 7,553,309 | B2 | 6/2009 | Buysse et al. |
| 7,556,095 | B2 | 7/2009 | Vinegar |
| 7,556,096 | B2 | 7/2009 | Vinegar |
| 7,559,367 | B2 | 7/2009 | Vinegar |
| 7,559,368 | B2 | 7/2009 | Vinegar |
| 7,562,706 | B2 | 7/2009 | Li et al. |
| 7,562,707 | B2 | 7/2009 | Miller |
| 7,578,815 | B2 | 8/2009 | Howell |
| 7,581,589 | B2 | 9/2009 | Roes et al. |
| 7,584,789 | B2 | 9/2009 | Mo et al. |
| 7,588,565 | B2 | 9/2009 | Marchitto et al. |
| 7,588,566 | B2 | 9/2009 | Treat et al. |
| 7,591,310 | B2 | 9/2009 | Minderhoud |
| 7,597,147 | B2 | 10/2009 | Vitek |
| 7,604,052 | B2 | 10/2009 | Roes |
| 7,610,962 | B2 | 11/2009 | Fowler |
| 7,613,523 | B2 | 11/2009 | Eggers et al. |
| 7,631,689 | B2 | 12/2009 | Vinegar |
| 7,631,690 | B2 | 12/2009 | Vinegar |
| 7,632,295 | B2 | 12/2009 | Flores |
| 7,635,023 | B2 | 12/2009 | Goldberg |
| 7,635,024 | B2 | 12/2009 | Karanikas |
| 7,635,025 | B2 | 12/2009 | Vinegar |
| 7,678,105 | B2 | 3/2010 | McGreevy et al. |
| 7,686,804 | B2 | 3/2010 | Johnson et al. |
| 7,699,842 | B2 | 4/2010 | Buysse et al. |
| 7,702,397 | B2 | 4/2010 | Fredricks et al. |
| 7,776,035 | B2 | 8/2010 | Rick et al. |
| 7,828,798 | B2 | 11/2010 | Buysse et al. |
| 7,871,406 | B2 | 1/2011 | Nields et al. |
| 7,879,033 | B2 | 2/2011 | Sartor et al. |
| 7,887,535 | B2 | 2/2011 | Lands et al. |
| 7,922,713 | B2 | 4/2011 | Geisel |
| 7,931,649 | B2 | 4/2011 | Couture et al. |
| 7,938,779 | B2 | 5/2011 | Sakurai et al. |
| 7,951,149 | B2 | 5/2011 | Carlton |
| 7,951,150 | B2 | 5/2011 | Johnson et al. |
| 7,959,633 | B2 | 6/2011 | Sartor et al. |
| 7,963,965 | B2 | 6/2011 | Buysse et al. |
| 7,972,334 | B2 | 7/2011 | McGreevy et al. |
| 7,972,335 | B2 | 7/2011 | McGreevy et al. |
| 7,981,113 | B2 | 7/2011 | Truckai et al. |
| 8,062,290 | B2 | 11/2011 | Buysse et al. |
| 8,100,896 | B2 | 1/2012 | Podhajsky |
| 8,100,908 | B2 | 1/2012 | McGaffigan et al. |
| 8,104,956 | B2 | 1/2012 | Blaha |
| 8,105,323 | B2 | 1/2012 | Buysse et al. |
| 8,211,105 | B2 | 7/2012 | Buysse et al. |
| 8,241,284 | B2 | 8/2012 | Dycus et al. |
| 8,287,528 | B2 | 10/2012 | Wham et al. |
| 8,377,052 | B2 | 2/2013 | Manwaring et al. |
| 8,377,057 | B2 | 2/2013 | Rick et al. |
| 8,398,626 | B2 | 3/2013 | Buysse et al. |
| 8,480,666 | B2 | 7/2013 | Buysse et al. |
| 8,568,402 | B2 | 10/2013 | Buysse et al. |
| 8,591,506 | B2 | 11/2013 | Wham et al. |
| 8,667,674 | B2 | 3/2014 | Buysse |
| 8,672,938 | B2 | 3/2014 | Buysse et al. |
| 2001/0014804 | A1 | 8/2001 | Goble et al. |
| 2002/0019627 | A1 * | 2/2002 | Maguire et al. ............... 606/27 |
| 2002/0019644 | A1 | 2/2002 | Hastings et al. |
| 2002/0026188 | A1 | 2/2002 | Balbierz et al. |
| 2002/0029037 | A1 | 3/2002 | Kim |
| 2002/0029062 | A1 * | 3/2002 | Satake ........................ 606/194 |
| 2002/0068931 | A1 | 6/2002 | Wong et al. |
| 2002/0087156 | A1 * | 7/2002 | Maguire et al. ............... 606/41 |
| 2002/0120261 | A1 | 8/2002 | Balbierz et al. |
| 2002/0133148 | A1 | 9/2002 | Daniel et al. |
| 2002/0173787 | A1 | 11/2002 | Buysse et al. |
| 2003/0004507 | A1 | 1/2003 | Francischelli et al. |
| 2003/0055417 | A1 | 3/2003 | Truckai et al. |
| 2003/0055424 | A1 | 3/2003 | Ciarrocca |
| 2003/0060818 | A1 | 3/2003 | Kannenberg et al. |
| 2003/0073987 | A1 | 4/2003 | Sakurai et al. |
| 2003/0073989 | A1 | 4/2003 | Hoey et al. |
| 2003/0109871 | A1 | 6/2003 | Johnson et al. |
| 2003/0144660 | A1 | 7/2003 | Mollenauer |
| 2003/0171747 | A1 | 9/2003 | Kanehira et al. |
| 2003/0176873 | A1 | 9/2003 | Chernenko et al. |
| 2003/0195499 | A1 | 10/2003 | Prakash et al. |
| 2003/0199755 | A1 | 10/2003 | Halperin |
| 2004/0006335 | A1 | 1/2004 | Garrison |
| 2004/0030330 | A1 | 2/2004 | Brassell et al. |
| 2004/0034349 | A1 | 2/2004 | Kirwan, Jr. et al. |
| 2004/0049185 | A1 | 3/2004 | Latterell et al. |
| 2004/0059345 | A1 | 3/2004 | Nakao et al. |
| 2004/0073256 | A1 | 4/2004 | Marchitto |
| 2004/0167506 | A1 | 8/2004 | Chen |

(56) References Cited

U.S. PATENT DOCUMENTS

| | | |
|---|---|---|
| 2004/0176756 A1 | 9/2004 | McGaffigan |
| 2004/0187875 A1 | 9/2004 | He et al. |
| 2004/0243120 A1 | 12/2004 | Orszulak et al. |
| 2005/0021016 A1 | 1/2005 | Malecki et al. |
| 2005/0033338 A1 | 2/2005 | Ferree |
| 2005/0072827 A1 | 4/2005 | Mollenauer |
| 2005/0107776 A1 | 5/2005 | Mcgaffigan et al. |
| 2005/0113824 A1 | 5/2005 | Sartor et al. |
| 2005/0197661 A1 | 9/2005 | Carrison et al. |
| 2005/0245919 A1 | 11/2005 | Van der Welde |
| 2005/0273111 A1 | 12/2005 | Ferree et al. |
| 2005/0283067 A1 | 12/2005 | Sobe |
| 2005/0283149 A1 | 12/2005 | Thorne et al. |
| 2005/0288659 A1 | 12/2005 | Kimura et al. |
| 2006/0127706 A1 | 6/2006 | Goebel et al. |
| 2006/0142824 A1 | 6/2006 | Zikorus et al. |
| 2006/0161149 A1 | 7/2006 | Privitera et al. |
| 2006/0167450 A1 | 7/2006 | Johnson et al. |
| 2006/0212030 A1 | 9/2006 | McGaffigan |
| 2006/0212031 A1 | 9/2006 | McGaffigan et al. |
| 2006/0217700 A1 | 9/2006 | Garito et al. |
| 2006/0217706 A1 | 9/2006 | Lau et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0271037 A1 | 11/2006 | Maroney et al. |
| 2007/0005054 A1 | 1/2007 | Heim et al. |
| 2007/0005055 A1 | 1/2007 | Heim et al. |
| 2007/0005056 A1 | 1/2007 | Heim et al. |
| 2007/0005057 A1 | 1/2007 | Heim et al. |
| 2007/0005058 A1 | 1/2007 | Heim et al. |
| 2007/0005059 A1 | 1/2007 | Heim et al. |
| 2007/0005060 A1 | 1/2007 | Heim et al. |
| 2007/0016181 A1 | 1/2007 | van der Weide et al. |
| 2007/0060920 A1 | 3/2007 | Weitzner |
| 2007/0073282 A1 | 3/2007 | McGaffigan et al. |
| 2007/0100336 A1 | 5/2007 | McFarlin et al. |
| 2007/0106294 A1 | 5/2007 | Nesbitt |
| 2007/0127897 A1 | 6/2007 | John et al. |
| 2007/0131428 A1 | 6/2007 | Boestert |
| 2007/0173811 A1 | 7/2007 | Couture et al. |
| 2007/0208339 A1 | 9/2007 | Arts et al. |
| 2007/0239151 A1 | 10/2007 | Atalar et al. |
| 2007/0270924 A1 | 11/2007 | McCann et al. |
| 2008/0017380 A1 | 1/2008 | Vinegar |
| 2008/0033419 A1 | 2/2008 | Nields et al. |
| 2008/0035346 A1 | 2/2008 | Nair et al. |
| 2008/0035347 A1 | 2/2008 | Brady |
| 2008/0035705 A1 | 2/2008 | Menotti |
| 2008/0038144 A1 | 2/2008 | Maziasz |
| 2008/0077129 A1 | 3/2008 | Van Wyk et al. |
| 2008/0119841 A1 | 5/2008 | Geisel |
| 2008/0128134 A1 | 6/2008 | Mudunuri et al. |
| 2008/0135253 A1 | 6/2008 | Vinegar |
| 2008/0135254 A1 | 6/2008 | Vinegar |
| 2008/0142216 A1 | 6/2008 | Vinegar |
| 2008/0142217 A1 | 6/2008 | Pieterson |
| 2008/0161800 A1 | 7/2008 | Wang et al. |
| 2008/0173444 A1 | 7/2008 | Stone et al. |
| 2008/0174115 A1 | 7/2008 | Lambirth |
| 2008/0185147 A1 | 8/2008 | Vinegar |
| 2008/0187989 A1 | 8/2008 | McGreevy et al. |
| 2008/0217003 A1 | 9/2008 | Kuhlman |
| 2008/0217016 A1 | 9/2008 | Stegemeier |
| 2008/0228135 A1 | 9/2008 | Snoderly |
| 2008/0236831 A1 | 10/2008 | Hsu |
| 2008/0277113 A1 | 11/2008 | Stegemeier |
| 2008/0281310 A1 | 11/2008 | Dunning et al. |
| 2008/0281315 A1 | 11/2008 | Gines |
| 2008/0319438 A1 | 12/2008 | DeCarlo |
| 2009/0014180 A1 | 1/2009 | Stegemeier |
| 2009/0014181 A1 | 1/2009 | Vinegar |
| 2009/0093811 A1 | 4/2009 | Koblish et al. |
| 2009/0112200 A1 | 4/2009 | Eggers |
| 2009/0118729 A1 | 5/2009 | Auth et al. |
| 2009/0118730 A1 | 5/2009 | Mollenauer |
| 2009/0198224 A1 | 8/2009 | McGaffigan |
| 2009/0248002 A1 | 10/2009 | Takashino et al. |
| 2009/0292347 A1 | 11/2009 | Asmus et al. |
| 2009/0306644 A1 | 12/2009 | Mayse et al. |
| 2009/0312753 A1 | 12/2009 | Shadduck |
| 2010/0004650 A1* | 1/2010 | Ormsby et al. ............... 606/41 |
| 2010/0082022 A1 | 4/2010 | Haley et al. |
| 2010/0152725 A1 | 6/2010 | Pearson et al. |
| 2010/0198216 A1 | 8/2010 | Palanker |
| 2010/0228244 A1 | 9/2010 | Hancock et al. |
| 2010/0268205 A1 | 10/2010 | Manwaring |
| 2010/0268206 A1 | 10/2010 | Manwaring |
| 2010/0268207 A1 | 10/2010 | Manwaring |
| 2010/0268208 A1 | 10/2010 | Manwaring |
| 2010/0268209 A1 | 10/2010 | Manwaring |
| 2010/0268210 A1 | 10/2010 | Manwaring |
| 2010/0268211 A1 | 10/2010 | Manwaring |
| 2010/0268212 A1 | 10/2010 | Manwaring |
| 2010/0268213 A1 | 10/2010 | Manwaring |
| 2010/0268214 A1 | 10/2010 | Manwaring |
| 2010/0268215 A1 | 10/2010 | Manwaring |
| 2010/0268216 A1 | 10/2010 | Manwaring |
| 2010/0268218 A1 | 10/2010 | Ormsby et al. |
| 2011/0004204 A1 | 1/2011 | Dodde et al. |
| 2011/0054456 A1 | 3/2011 | Thompson et al. |
| 2011/0092971 A1 | 4/2011 | Sartor et al. |
| 2011/0152857 A1 | 6/2011 | Ingle |
| 2012/0059367 A1 | 3/2012 | Buysse et al. |
| 2012/0130256 A1 | 5/2012 | Buysse et al. |
| 2012/0150170 A1 | 6/2012 | Buysse et al. |
| 2012/0303026 A1 | 11/2012 | Dycus et al. |
| 2013/0041367 A1 | 2/2013 | Wham et al. |
| 2014/0058381 A1 | 2/2014 | Wham et al. |
| 2014/0058384 A1 | 2/2014 | Buysse et al. |
| 2014/0058385 A1 | 2/2014 | Wham et al. |
| 2014/0100559 A1 | 4/2014 | Wham et al. |
| 2014/0180266 A1 | 6/2014 | Buysse et al. |

FOREIGN PATENT DOCUMENTS

| | | |
|---|---|---|
| EP | 2036512 A1 | 3/2009 |
| EP | 2070486 | 6/2009 |
| GB | 2 022 974 | 12/1978 |
| GB | 1 546 624 | 5/1979 |
| JP | 03-051179 | 6/1987 |
| JP | 2558584 | 9/1996 |
| RU | 2 072 118 | 1/1997 |
| WO | WO-82/00746 | 3/1982 |
| WO | WO 92/17121 | 10/1992 |
| WO | WO-93/21839 | 11/1993 |
| WO | WO-96/26677 | 11/1996 |
| WO | WO 9937227 A1 | 7/1999 |
| WO | WO-01/06943 | 2/2001 |
| WO | WO-2004/014217 | 2/2004 |
| WO | WO-2004/076146 | 9/2004 |
| WO | WO-2006/017517 | 2/2006 |
| WO | WO-2006/029649 | 3/2006 |
| WO | WO 2007080578 A2 | 7/2007 |
| WO | WO-2008/060668 | 5/2008 |

OTHER PUBLICATIONS

International Search Report from related PCT Patent Application No. PCT/US2010/031114, Jan. 21, 2011.

International Preliminary Report on Patentability from related PCT Patent Application No. PCT/US2010/031114, Nov. 1, 2011.

Metcal Soldering Iron Catalog—2006.

URSI EMTS 2004, pp. 489-491, *Electromagnetic Probes for Living Tissue Cauterization.*

Translation of Office Action from related Japanese Patent Application No. 2012-506188, PCT US2010-031114.

International Preliminary Report on Patentability from related PCT Patent Application No. PCT/US2012/032659, Nov. 23, 2012.

International Preliminary Report on Patentability from related PCT Patent Application No. PCT/US2012/038005, Nov. 23, 2012.

(56) References Cited

OTHER PUBLICATIONS

International Preliminary Report on Patentability from related PCT Patent Application No. PCT/US2012/032656, Oct. 23, 2012.
Written Opinion of the International Preliminary Examining Authority from related PCT Patent Application No. PCT/US2011/050417, Feb. 6, 2013.
Visioli, Antonio. Practice PID Control: London: Springer-Verlag, 2006. 1-18. Print.
International Search Report and Written Opinion from related PCT Application US2012/032661, Aug. 19, 2013.
International Search Report and Written Opinion from related PCT Application US2012/032659, Oct. 8, 2013.
International Search Report and Written Opinion from related PCT Application US2012/032565, Oct. 8, 2013.
"High Temp Metals." NI2001201 Technical Data. High Temp Metals, Inc., n.d. Web. Jul. 13, 2012. <http://www.hightempmetals.com/techdatafnitempNi200data.php.
International Preliminary Report on Patentability from PCT/US2012/068027, dated Jun. 10, 2014.
International Search Report and Written Opinion from related PCT Application US2012/038005, Nov. 19, 2013.
International Preliminary Report on Patentability from related PCT Patent Application No. PCT/US2011/050417, Apr. 12, 2012.
International Preliminary Report on Patentability from related PCT Patent Application No. PCT/US2012/055229, Feb. 1, 2013.
International Preliminary Report on Patentability from related PCT Patent Application No. PCT/US2012/068027, Feb. 25, 2013.
European Search Report from European Application No. 12865504.0-1652, dated Nov. 28, 2014.

* cited by examiner

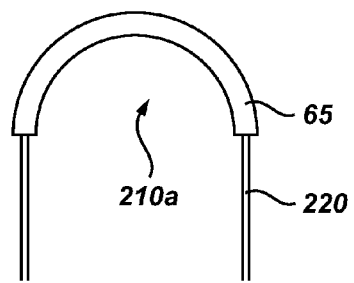
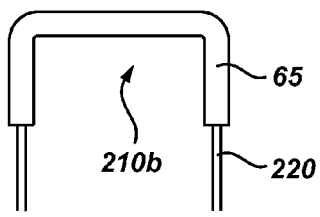
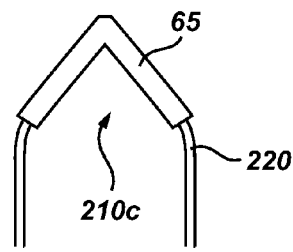
*Fig. 7A*  *Fig. 7B*  *Fig. 7C*
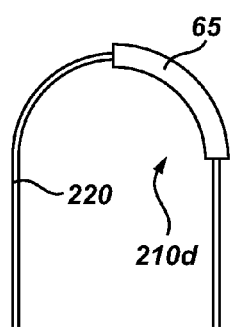
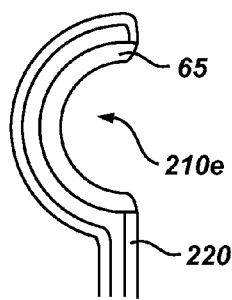
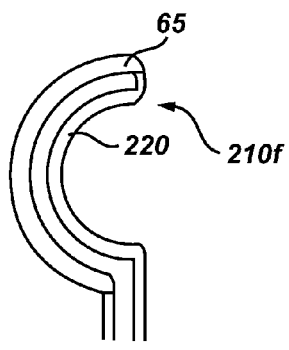
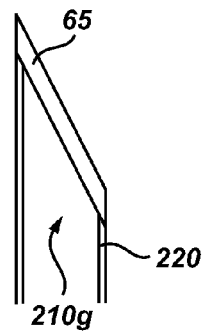
*Fig. 7D*  *Fig. 7E*  *Fig. 7F*  *Fig. 7G*

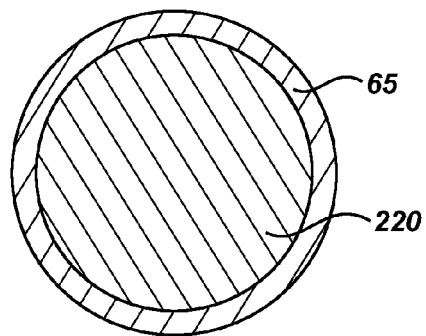
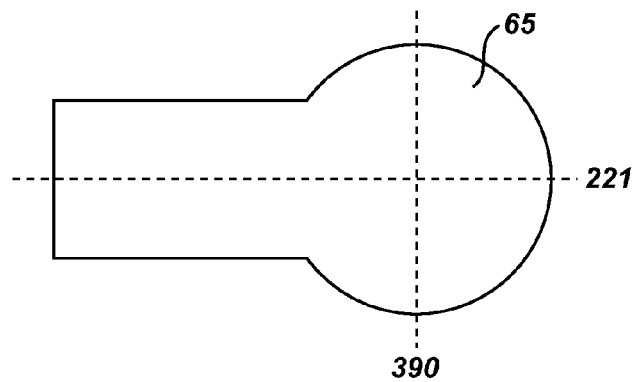
*Fig. 13*  *Fig. 14A*
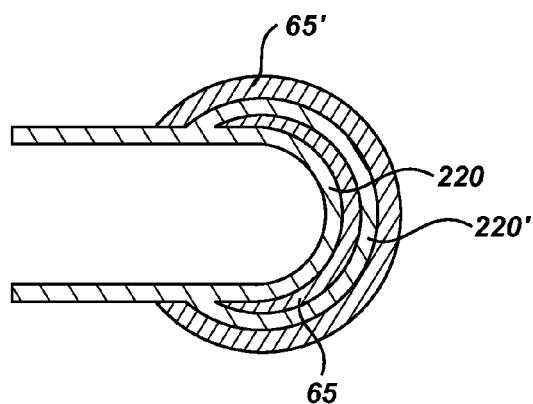
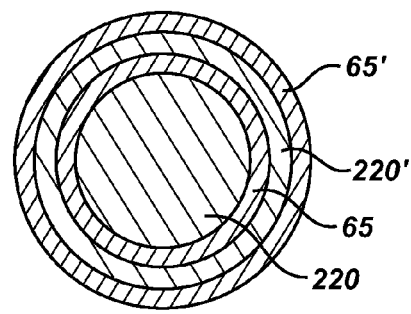
*Fig. 14B*  *Fig. 15*

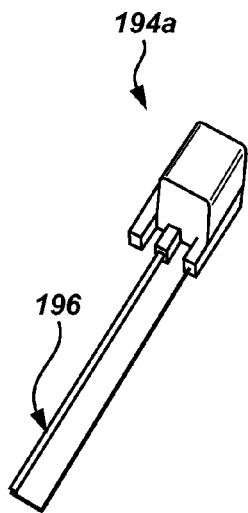 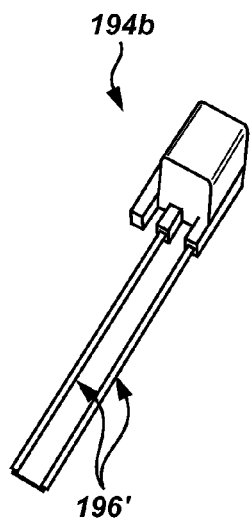 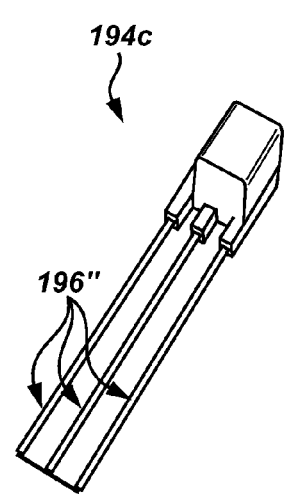
*Fig. 18A*  *Fig. 18B*  *Fig. 18C*
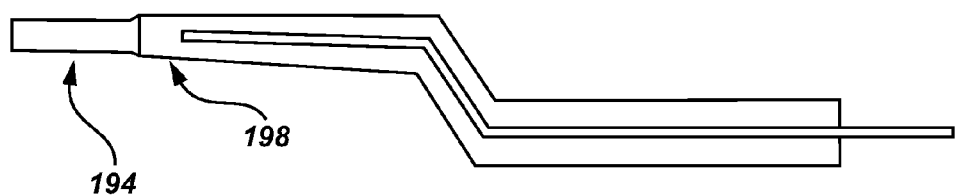
*Fig. 18D*

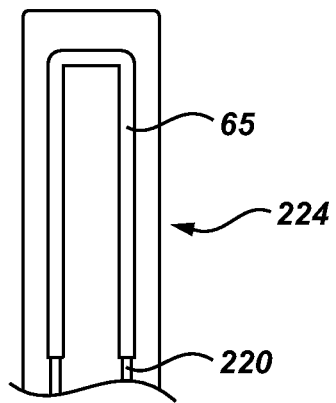
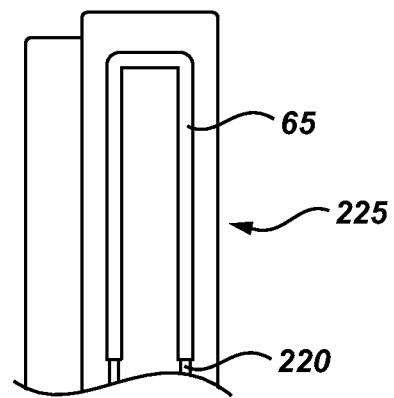
Fig. 20A  Fig. 20B
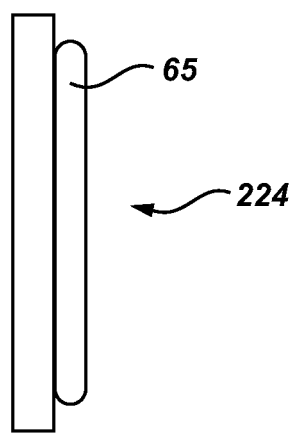
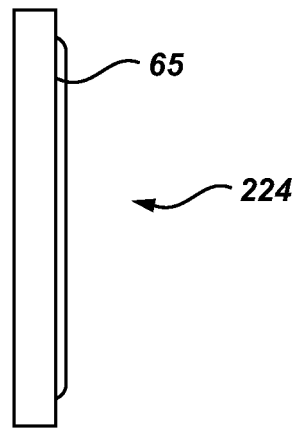
Fig. 20C  Fig. 20D

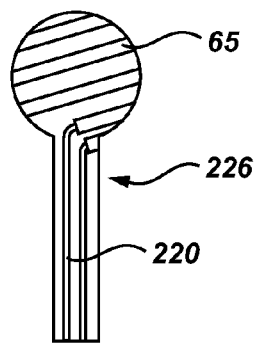
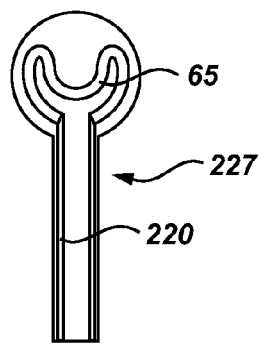
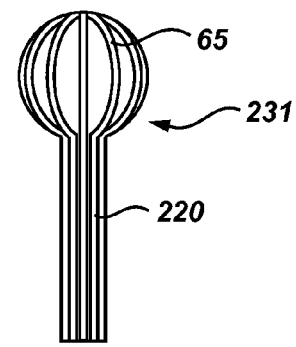
*Fig. 21A*     *Fig. 21B*     *Fig. 21C*

HEATED BALLOON CATHETER

RELATED APPLICATIONS

The present application is a continuation-in-part of U.S. patent application Ser. No. 12/647,358, filed Dec. 24, 2009, now U.S. Pat. No. 8,506,561, which claims the benefit of U.S. Provisional Patent Application Ser. No. 61/170,203, filed Apr. 17, 2009, U.S. Provisional Patent Application Ser. No. 61/170,220, filed Apr. 17, 2009, and U.S. Provisional Patent Application Ser. No. 61/170,207, filed Apr. 17, 2009, each of which are incorporated hereby by references in their entirety. The present application also claims the benefit of U.S. Provisional Application Ser. No. 61/380,179, filed on Sep. 3, 2010, and U.S. Provisional Application Ser. No. 61/473,715, filed on Apr. 8, 2011, which are each incorporated herein by reference in their entirety.

BACKGROUND OF THE INVENTION

1. The Field of the Invention

The present invention relates to surgical tools. More specifically, the present invention relates to thermally adjustable surgical tools, such as balloon catheters, used in open and minimally invasive surgical procedures and interventional surgical and therapeutic procedures.

2. State of the Art

Surgery generally involves cutting, repairing, removing and/or destroying tissue or other materials. There are multiple electrosurgery modalities used for cutting, coagulating, desiccating, ablating, or fulgurating tissue. Many of these, however, have undesirable side effects and drawbacks.

Monopolar and bipolar electrosurgery modalities generally have disadvantages relating to "beyond the tip" effects. These effects are caused by passing alternating current through tissues in contact with conducting instruments or probes.

Monopolar surgical instruments require electric current to pass through the patient. A return electrode is placed on the patient, often on the patient's thigh. Electricity is conducted from a "knife" electrode through the tissue and returns through the return electrode. Other forms of monopolar instruments exist, such as those which use the capacitive effect of the body to act as the return electrode or ground.

A low voltage, high frequency waveform will incise, but has little hemostatic effect. A high voltage waveform will cause adjacent tissue hemostasis and coagulation. Therefore, when hemostasis is desirable, high voltage is used. The high voltage spark frequently has deeper tissue effects than the cut because more electricity must pass through the patient. The damage to the tissue extends away from the actual point of coagulation. Furthermore, there are complaints of return electrode burns. Yet, any reduction of voltage reduces the effectiveness of hemostasis. Further, the temperature of the spark or arc cannot be precisely controlled, which can lead to undesirable charring of target tissue.

Bipolar surgical instruments can produce tissue damage and problems similar to monopolar devices, such as sparking, charring, deeper tissue effects and electric current damage away from the application of energy with varying effects due to the differing electrical conductivity of tissue types, such as nerve, muscle, fat and bone, and into adjacent tissues of the patient. However, the current is more, but not completely, contained between the bipolar electrodes. These electrodes are also generally more expensive because there are at least two precision electrodes that must be fabricated instead of the one monopolar electrode.

Electrocautery resistive heating elements reduce the drawbacks associated with charring and deeper tissue damage caused by other electrosurgery methods. However, such devices often present other tradeoffs, such as the latency in controlling heating and cooling time, and effective power delivery. Many resistive heating elements have slow heating and cooling times, which makes it difficult for the surgeon to work through or around tissue without causing incidental damage.

Tissue destruction instruments generally heat tissue to a predetermined temperature for a period of time to kill, or ablate, the tissue. In some controlled heating of tissues, a laser is directed to an absorptive cap to reach and maintain a predetermined temperature for a predetermined amount of time. While this provides the benefits of thermal heating, it is expensive due to the complexity and expense of laser hardware.

In another tissue destruction procedure, a microwave antenna array is inserted into the tissue. These arrays are powered by instruments that cause microwave energy to enter and heat the tissue. While such devices are often effective at killing, or ablating, the desired tissue, they often cause deeper tissue effects outside the desired area. Additionally the procedures can require expensive equipment.

Tissue destruction with resistively heated tools can produce unintended collateral tissue damage, in addition to having slow heating and cooling attributes.

Uses of ferrite beads and alloy mixes in ceramics have been examined as alternatives. When excited by the magnetic field associated with high frequency current passing through a conductor, ferrite beads and alloy mixes in ceramics can reach high temperatures very quickly. However, one major problem with the use of these materials is that a large temperature differential can cause the material to fracture, especially when it comes into and out of contact with liquids. In other words, if a hot ferrite surgical instrument is quenched by a cooler pool of liquid, such as blood or other body fluids, the material's corresponding temperature drops rapidly and may cause the material to fracture. These fractures not only cause the tool to lose its effectiveness as a heat source, because the magnetic field is disrupted, but may require extraction of the material from the patient. Obviously, the need to extract small pieces of ferrite product from a patient is highly undesirable.

Thus, there is a need for improved thermal surgical tools for tissue destruction and other therapies.

SUMMARY OF THE INVENTION

It is an object of the present invention to provide an improved thermally adjustable surgical or therapeutic tool, which may include cutting instruments, shaping instruments and instruments designed to apply heat to a broader area, such as heated balloon catheters.

According to one aspect of the invention, a thermal surgical tool system is provided with a ferromagnetic coating over a conductor and an oscillating electrical energy source for generating heat at the location of the coating. The oscillating electrical energy may cause inductive heating of the ferromagnetic coating. Moreover, the surgeon may be able to quickly turn the surgical or therapeutic tool on and off due to a small heat latency. This may provide the advantage of allowing the surgeon to rapidly deliver a thermal effect only at desired locations, which may also prevent the accidental delivery of undesired thermal effects while waiting for the tool to cool.

According to another aspect of the invention, a thermal surgical tool system may be configured so that the power delivery to a ferromagnetic element may be altered by the surgeon in near real-time to achieve different tissue effects.

According to another aspect of the invention, controlled thermal tissue destruction may be performed.

According to another aspect of the invention, the coated conductor may be incorporated in a catheter or endoscope, which could also provide for sensing, viewing, aspiration, irrigation, delivery of a thermally-cured material, or removal of a thermally-melted or ablated material, through a channel.

According to another aspect of the invention a catheter may be used to deliver a ferromagnetic coated conductor into an area for a desired therapeutic effect.

According to another aspect of the invention, the thermal system may also be used to sculpt, melt, break and/or remove biological material. This includes blockages of the body that may be reduced in size, have their shape altered or material transitioned into a liquid state to help the body remove such substances. Similarly, biological material may be altered to aid in removal of tissue or other substances during laparoscopic or other small surgical hole procedures.

According to another aspect of the invention, a thermal system may be used to sculpt portions of biological material. For example, a herniated spinal disc may be sculpted such that the herniated portion is removed so that the disc remains within the spinal column. Likewise, biological material, such as cartilage may be smoothed to repair damage and/or to prevent further damage of an uneven surface. Furthermore, a thermal tool may be used to reduce plaque formations in blood vessels or to smooth ducts to thereby improve flow there through. Moreover, tissue may be thermally treated to reduce size and/or allow for easier removal of the tissue, such as, for example, reducing the size of stones in a gall bladder prior to removal from a small incision.

According to one aspect of the invention, a thermal system can be formed as part of a balloon catheter. A fluid filling the balloon catheter may be heated as it enters the balloon chamber. By heating the fluid as it enters the balloon chamber the fluid inside the catheter may remain at a desired temperature or within a desired range due to heating or thermal elements (discussed interchangeably as heating elements or thermal elements) in the catheter. Furthermore, the fluid entering the catheter may be monitored for temperature and cause adjustment to the heating element, ensuring a more consistent temperature in the balloon.

According to another aspect of the invention, a sensor network may monitor the fluid and/or the tissue surface. The heat output by the heating element may be monitored and adjusted based on the feedback by the sensors. By monitoring the temperature and adjusting the heating element, a more consistent temperature may be maintained.

These and other aspects of the present invention are realized in an improved thermally adjustable surgical or therapeutic tool as shown and described in the following figures and related description.

BRIEF DESCRIPTION OF THE DRAWINGS

Various embodiments of the present invention are shown and described in reference to the numbered drawings wherein:

FIG. 7A shows a close-up view of ferromagnetic coated conductor surgical tool tip with a loop geometry in accordance with one aspect of the present invention;

FIG. 7B shows a close-up view of a ferromagnetic coated conductor surgical tool tip with a generally square geometry in accordance with one aspect of the present invention;

FIG. 7C shows a close-up view of a ferromagnetic coated conductor surgical tool tip with a pointed geometry;

FIG. 7D shows a close-up view of a ferromagnetic coated conductor surgical tool tip with an asymmetrical loop geometry;

FIG. 7E shows a close-up view of a ferromagnetic coated conductor surgical tool tip with a hook geometry in which the concave portion may be used for therapeutic effect, including cutting;

FIG. 7F shows a close up view of a ferromagnetic coated conductor surgical tool tip with a hook geometry in which the convex portion may be used for therapeutic effect, including cutting;

FIG. 7G shows a close up view of a ferromagnetic coated conductor surgical tool tip with an angled geometry;

FIG. 13 shows an axial cross-sectional view of a single layer ferromagnetic coated conductor surgical tool in the ferromagnetic-coated region;

FIG. 14A shows a perspective view of a multi-layer ferromagnetic coated conductor surgical tool tip;

FIG. 14B shows a side cross-sectional view of a multi-layer ferromagnetic coated conductor surgical tool tip shown in 14A;

FIG. 15 shows an axial cross-section of the multi-layer ferromagnetic coated conductor surgical tool tip shown in FIG. 14A;

FIG. 18A shows a single edge ferromagnetic coated conductor surgical tool tip in accordance with one aspect of the invention;

FIG. 18B shows a double edge ferromagnetic coated conductor surgical tool tip;

FIG. 18C shows a three wire ferromagnetic coated conductor surgical tool tip;

FIG. 18D shows a handpiece or receptacle for the tips shown in FIGS. 18A through 18C;

FIG. 20A shows a thermal surgical tool with a spatula shaped geometry;

FIG. 20B shows a thermal surgical tool with a spatula shaped geometry in a forceps configuration;

FIG. 20C shows a top view of the thermal surgical tool of FIG. 20A with the ferromagnetic coated conductor upon the primary geometry;

FIG. 20D shows a top view of the thermal surgical tool of FIG. 20A with the ferromagnetic coated conductor embedded within the primary geometry;

FIG. 21A shows a thermal surgical tool with a ball shaped geometry and horizontal winding;

FIG. 21B shows an alternate embodiment of a thermal surgical tool with a ball shaped geometry and horseshoe configuration;

FIG. 21C shows an alternate embodiment of a thermal surgical tool with a ball shaped geometry and vertical orientation;

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

As used herein, the term "ferromagnetic," "ferromagnet," and "ferromagnetism" refers to any ferromagnetic-like material that is capable of producing heat due to magnetic induction, including but not limited to ferromagnets and ferrimagnets. It is not intended that such materials must be heated exclusively due to magnetic induction and such may acquire heat from resistive loses, including the skin effect due to eddy currents, in addition to magnetic induction.

Figure 1:
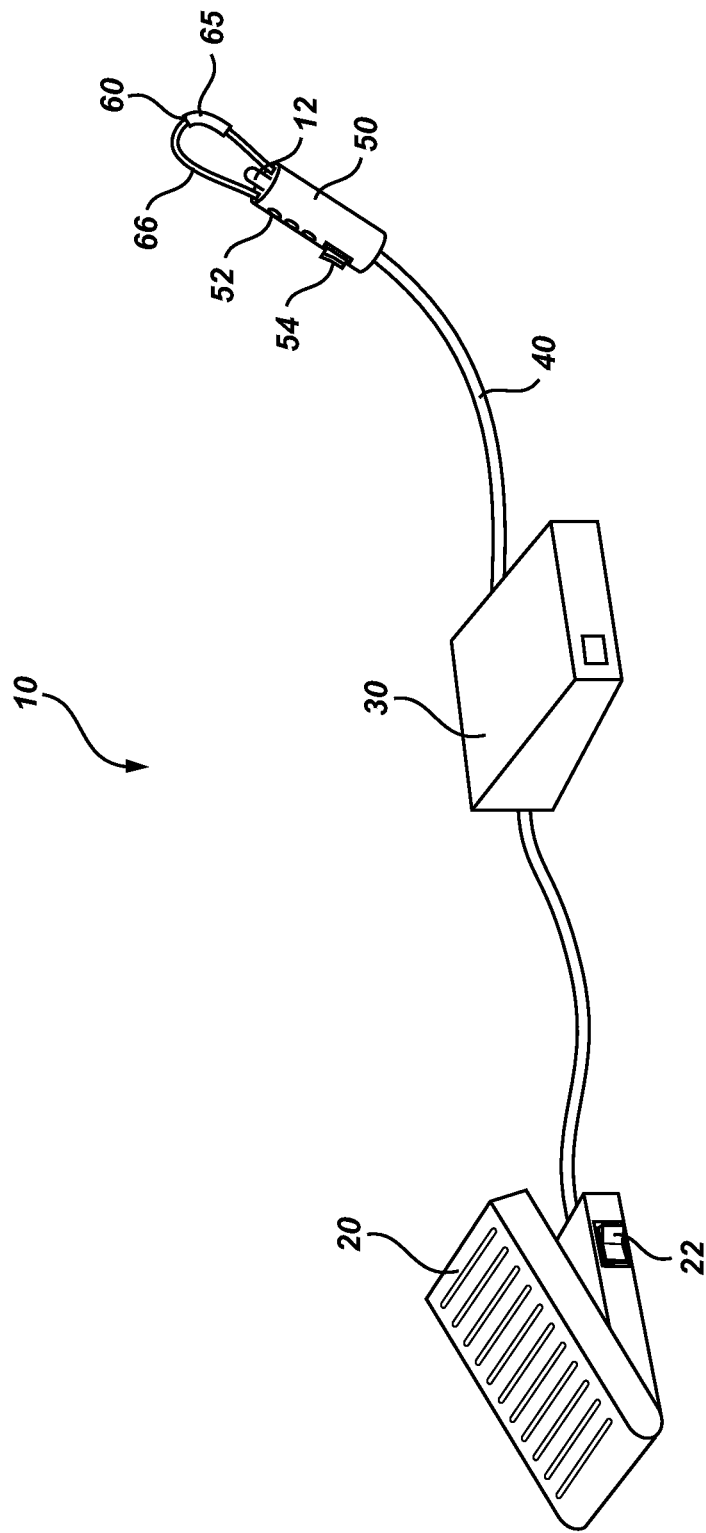
FIG. 1 shows a perspective view of a thermal surgical tool system in accordance with the principles of the present invention.

Turning now to FIG. 1, there is shown a perspective view of a thermal surgical tool system, generally indicated at 10. As will be discussed in additional detail below, the thermal tool system may use a ferromagnetic coated conductor to treat or destroy tissue (i.e. endothelial tissue welding, homeostasis, ablation, etc).

It will be appreciated that the thermal surgical tool may use heat to incise tissue, rather than cutting tissue in the sense of a sharp edge being drawn across the tissue as with a conventional scalpel. While the embodiments of the present invention could be made with a relatively sharp edge so as to form a cutting blade, such is not necessary as the heated coating discussed herein will separate tissue without the need for a cutting blade or sharp edge. However, for convenience, the term cutting is used when discussing separating tissue.

In the embodiment shown as thermal surgical tool system 10, a control mechanism, such as a foot pedal 20 is used to control output energy produced by a power subsystem 30. The energy from the power subsystem 30 may be sent via radio frequency (RF) or oscillating electrical energy along a cable 40 to a handheld surgical tool 50, which contains a conductor 60 having a section thereof circumferentially coated with a ferromagnetic coating 65. The ferromagnetic coating 65 may transfer the electrical energy into available thermal energy at the location of the ferromagnetic material disposed around or adjacent to a conductor wire. The heating may occur via induction and corresponding hysteresis losses in the ferromagnetic material disposed around or adjacent a conductor wire 66, and may also utilize resistive loses, including the skin effect due to eddy currents, etc. (While conductor wire is used for ease of reference, it will be appreciated that the conductor material need not be a wire and those skilled in the art will be familiar with multiple conductors which will work in light of the disclosure of the present invention.)

Application of a magnetic field to (or magnetizing) the ferromagnetic coating may produce an open loop B-H curve (also known as an open hysteresis loop), resulting in hysteresis losses and the resultant thermal energy. Electrodeposited films, such as a nickel-iron coating like PERMALLOY™, may form an array of randomly aligned microcrystals, resulting in randomly aligned domains, which together may have an open loop hysteresis curve when a high frequency current is passed through the conductor.

The RF energy may travel along the conductor's surface in a manner known as the "skin effect". The alternating RF current in the conductor's surface produces an alternating magnetic field, which may excite the domains in the ferromagnetic coating 65. As the domains realign with each oscillation of the current, hysteresis losses in the coating may cause inductive heating.

The RF conductor from the signal source up to and including the tip, may form a resonant circuit at a specific frequency (also known as a tuned circuit). Changes in the tip "detune" the circuit. Thus, should the ferromagnetic coating 65 or the conductor wire 66 become damaged, the circuit may likely become detuned. This detuning should reduce the efficiency of the heating of the ferromagnetic coating 65 such that the temperature will be substantially reduced. The reduced temperature should ensure little or no tissue damage after breakage.

It should be understood that the handheld surgical tool 50 may include indicia of the power being applied and may even include a mechanism for controlling the power. Thus, for example, a series of lights 52 could be used to indicate power level, or the handheld surgical tool 50 could include a switch, rotary dial, set of buttons, touchpad, etc., or slide 54 that communicates with the power source 30 to regulate power and thereby affect the temperature at the ferromagnetic coating 65 to having varying effects on tissue. While the controls are shown on the foot pedal 20 or the handheld surgical tool 50, they may also be included in the power subsystem 30 or even a separate control instrument. Safety features such as a button or touchpad that must be contacted to power the handheld surgical tool 50 may be employed, and may include a dead man's switch.

While the ferromagnetic coating 65 heats through induction, it also provides a temperature cap on the inductive component (and skin effect component due to eddy currents) of its heating due to its Curie temperature. A Curie temperature is the temperature at which the material becomes paramagnetic, such that the alignment of each domain relative to the magnetic field decreases to such an extent that the magnetic properties of the coating are lost. When the material becomes paramagnetic, the heating caused by induction may be significantly reduced or even cease. This causes the temperature of the ferromagnetic material to stabilize around the Curie temperature if sufficient power is provided to reach the Curie temperature and if any resistive component of heating is minimal. Once the temperature has dropped below the Curie temperature, induction may again start causing heating of the material up to the Curie temperature. Thus, the temperature in the ferromagnetic coating may reach the Curie temperature during inductive heating with the application of sufficient power, but will not likely exceed the Curie temperature if resistive effects are minimized.

The thermal surgical tool system 10 allows the power output to be adjustable in order to adjust the temperature of the tool and its effect on tissue. This adjustability gives the surgeon precise control over the effects that may be achieved by the handheld surgical tool 50. Tissue effects such as cutting, hemostasis, tissue welding, tissue vaporization and tissue carbonization occur at different temperatures. By using the foot pedal 20 (or some other user control) to adjust the power output, the surgeon (or other physician, etc.) can adjust the power delivered to the ferromagnetic coating 65 and consequently control the tissue effects to achieve a desired result.

Thermal power delivery can be controlled by varying the amplitude, frequency or duty cycle of the alternating current waveform, or alteration of the circuit to affect the standing wave driving the ferromagnetic coated conductor, which may be achieved by input received by the foot pedal 20, the power subsystem 30, or the controls on the handheld surgical tool 50.

One additional advantage achieved by the inductive heating is that the ferromagnetic material can be heated to a cutting temperature in a small fraction of a second (typically as short one quarter of a second). Additionally, because of the relatively low mass of the coating, the small thermal mass of the conductor, and the localization of the heating to a small region due to construction of the handheld surgical tool 50, the material will also cool extremely rapidly (e.g. approximately one half of a second). This provides a surgeon with a precise thermal tool while reducing accidental tissue damage caused by touching tissue when the thermal tool is not activated.

It will be appreciated that the time period required to heat and cool the handheld surgical tool 50 will depend, in part, on the relative dimensions of the conductor 60 and the ferromagnetic coating 65 and the heat capacity of the structure of the surgical tool. For example, the above time periods for heating and cooling of the handheld surgical tool 50 can be achieved with a tungsten conductor having a diameter of about 0.375 mm and a ferromagnetic coating of a Nickel Iron alloy (such as NIRON™ available from Enthone, Inc. of West Haven, Conn.) about the tungsten conductor which is about 0.0375 mm thick and two centimeters long.

One advantage of the present invention is that a sharp edge is not needed. When power is not being supplied to the surgical tool, the tool will not inadvertently cut tissue of the patient or of the surgeon if it is dropped or mishandled. If power is not being supplied to the conductor wire 66 and coating 65, the "cutting" portion of the tool may be touched without risk of injury. This is in sharp contrast to a cutting blade which may injure the patient or the surgeon if mishandled.

Other additions may also be placed on the handpiece in various locations. This may include a sensor stem 12 including a sensor to report temperature or a light to illuminate the surgical area.

Figure 2:
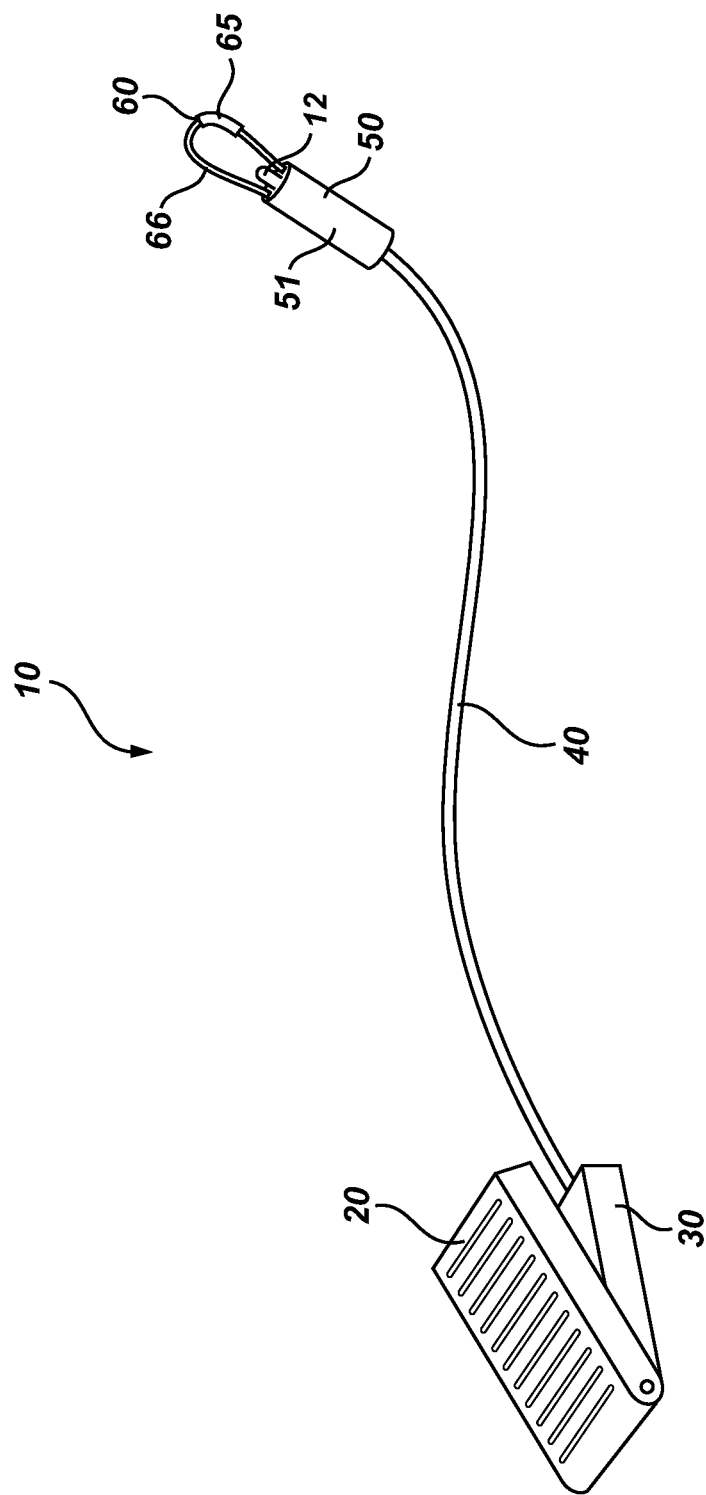
FIG. 2 shows a perspective view of an alternate embodiment of a thermal surgical tool system in accordance with the present invention.

Turning now to FIG. 2, a perspective view of an alternate embodiment of a thermal surgical system 10 is shown. In FIG. 2, the power source 30 is contained within the foot pedal 20. Depending on the application and power required, the instrument may even be entirely battery powered for relatively low power applications. An alternate embodiment for low power requirements may include the battery, power adjustment and power delivery, all self-contained in the handle 51 of the handheld surgical tool 50. Furthermore, a wireless communication module can be employed to send and receive information from the handheld surgical tool 50, including status and control settings that would enable users to monitor system performance and alter power settings remotely from the handheld surgical tool 50 itself.

It is our understanding that this thermal solution may provide advantages over monopolar and bipolar electrical systems currently available because the thermal damage may remain very close to the ferromagnetic surface of the coated region, whereas monopolar and bipolar electrical tissue ablation may frequently cause tissue damage a distance away from the point of contact. It is our understanding that this method may also overcome disadvantages of other thermal devices based upon resistive heating, which may require more time to heat and cool, and thus present greater patient risk, while potentially having higher voltage requirements at the point of heating.

Furthermore, the thin ferromagnetic coating 65, disposed along a small segment of the conductor, may reduce the heating of other non-target material in the body, such as blood when working within the heart in atrial ablation—which can lead to complications if a clot is formed. The small thermal mass of the conductor wire 66, and localization of the heating to a small region provided by the construction of the tool (i.e. ferromagnetic coating 65 and adjacent structures) provides a reduced thermal path for heat transfer in directions away from the location of the ferromagnetic coating 65. This reduced thermal path may result in the precise application of heat at only the point desired. As this technology alone does not employ a spark or an arc like monopolar or bipolar technology, risks of ignition, such as by anesthetic gasses within or around the patient by sparks, are also reduced.

The thermal surgical tool system 10 may be used for a variety of therapeutic means—including sealing, "cutting" or separating tissue, coagulation, or vaporization of tissue. In one configuration, the thermal surgical tool system 10 may be used like a knife or sealer, wherein the surgeon is actively "cutting" or sealing tissue by movement of the ferromagnetic coating 65 through tissue. The thermal action of the embodiments disclosed here may have distinct advantages including substantial reduction, if not elimination, of deep tissue effects compared with those associated with monopolar and bipolar RF energy devices.

In another configuration, the ferromagnetic coated conductor 60 may be inserted into a lesion and set to a specific power delivery or variable power delivery based on monitored temperature. The thermal effects on the lesion and surrounding tissue may be monitored until the desired thermal effect is achieved or undesired effects are noticed. One advantage of the application of the ferromagnetic coated conductor is that it may be cost-effective compared to microwave or thermal laser modalities and avoids the undesired tissue effects of microwave lesion destruction. Thus, for example, a surgeon can insert the ferromagnetic coated conductor into a tumor or other tissue to be destroyed and more precisely control the tissue damage that is created by activating the handheld surgical tool 50.

Sensors may be used to monitor conditions of the handheld surgical tool 50 or the tissue, such as an infrared detector or sensor stem 12. For instance, the temperature of the device or tissue may be important in performing a procedure. A sensor in the form of a thermocouple, a junction of dissimilar metals, thermistor or other temperature sensor may detect the temperature at or near the ferromagnetic coating 65 or tissue. The sensor may be part of the device, such as a thermocouple placed as a part of the conductor or near the ferromagnetic coating, or separate from the handheld surgical tool 50, such as a separate tip placed near the tissue or ferromagnetic coating 65. The temperatures may also be correlated with tissue effects, seen in FIG. 27. Other useful conditions to monitor may include, but are not limited to, color, spectral absorption, spectral reflection, temperature range, water content, proximity, tissue type, transferred heat, tissue status, impedance, resistance, voltage and/or visual feedback (e.g. a camera, fiberoptic or other visualization device).

The handheld surgical tool 50 may be configured for repeat sterilization or single patient uses. More complex devices may be useful for repeat sterilization, while more simple devices may be more useful for single patient use.

A method for treating or cutting tissue may include the steps of: selecting a surgical tool having a cutting edge and a conductor disposed adjacent the cutting edge, at least a portion of which is coated with a ferromagnetic material; applying oscillating electrical energy to the conductor to heat the ferromagnetic material; treating or cutting the tissue with the cutting edge.

Optional steps of the method may include: treating the tissue by causing hemostasis within cut tissue; using the heated ferromagnetic material to incise tissue; or using the heated ferromagnetic material to cause vascular endothelial welding.

Figure 3:
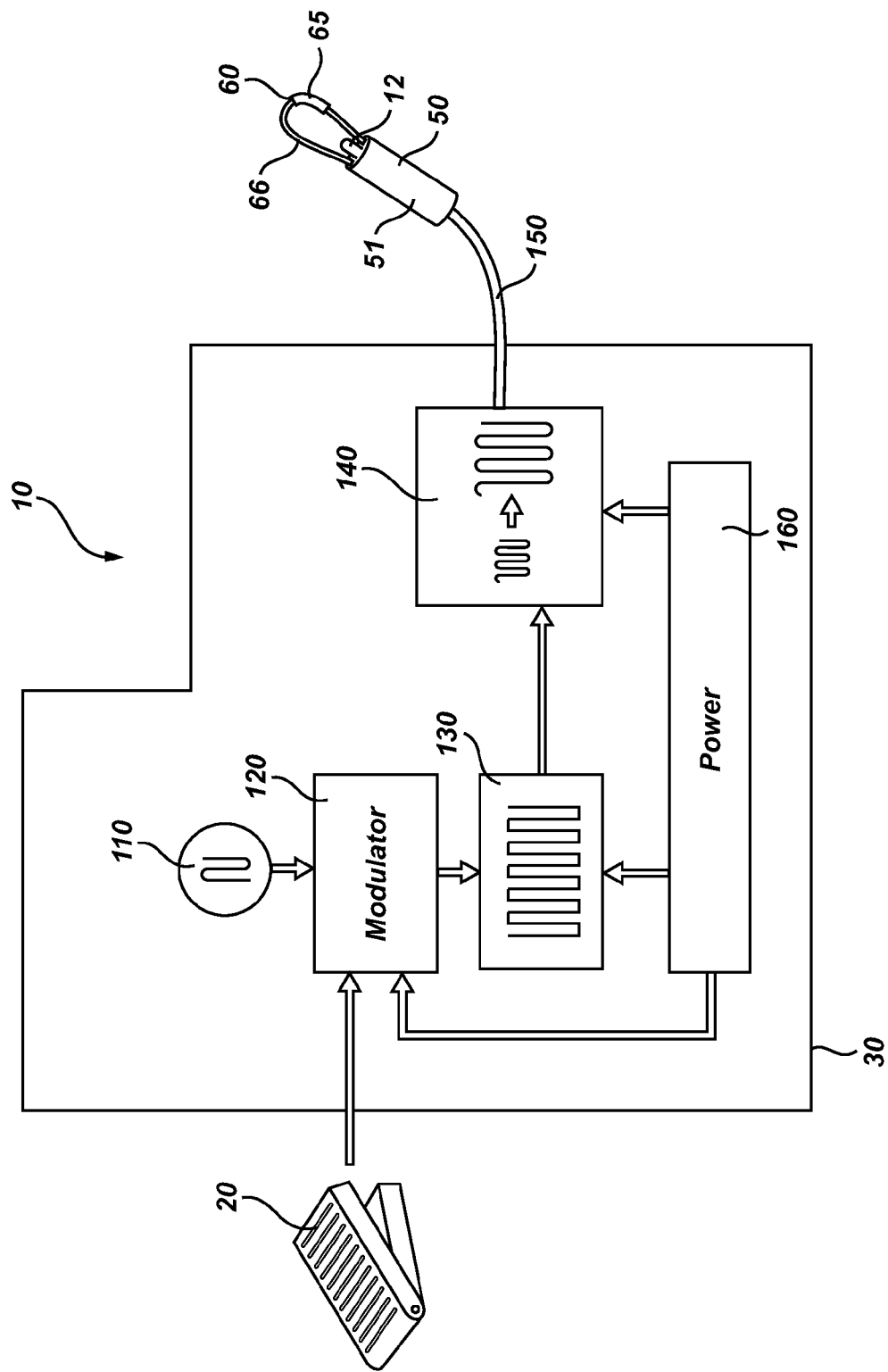
FIG. 3 shows a diagram of a thermal surgical tool system in accordance with the principles of the present invention.

Referring now to FIG. 3, a diagram of an embodiment of the adjustable thermal surgical tool system 10 is shown. The power delivery to the ferromagnetic coating 65 is controlled by a modulated high frequency waveform. The modulated waveform allows power delivery to be controlled in a manner that adjustably modifies, allows or blocks portions of the waveform based on the desired power delivery.

In FIG. 3, an initial waveform 110 is passed through a modulator 120 receiving commands from a foot pedal 20. The waveform is created by an oscillator 130 to the desired frequency, and modulated by the modulator 120, which may include, but is not limited to, one or more of amplitude, frequency or duty cycle modulation, including a combination thereof. The resultant signal is then amplified by an amplifier 140. The amplified signal is sent across a tuned cable 150, meaning that the cable is tuned to provide a standing wave with maximum current and minimum voltage at the location of the ferromagnetic coating 65 of the handheld surgical tool 50. Alternatively, the cable 150 may not be tuned, but a circuit may be placed in the handle 51 to impedance match the ferromagnetic coated conductor 60 as a load to the power source 30.

The thermal surgical tool system 10 may be tuned by specifying the location of the ferromagnetic coating 65 with respect to the amplifier 140 (such as cable length) and tuning the high frequency signal to approximately a resonant standing wave such that current is maximized at the location of the ferromagnetic coating 65.

It should be recognized that the surgical tool may operate in a dynamic environment. Thus when used herein, approximately a standing wave means that a circuit may be tuned such that the signal may be near an optimal standing wave but may not achieve it, may only achieve the wave for small amounts of time, or may successfully achieve a standing wave for longer periods of time. Similarly, any use of "standing wave" without the modifier of approximate should be understood to be approximate in the context of the thermal surgical tool.

One method for achieving such current maximization is to connect the ferromagnetic coated conductor 60 to a cable 150 that is an odd multiple of one-quarter wavelengths in length and connected to the output of the amplifier 140. The design of the circuit having a resonant standing wave is intended to optimize power delivery to the ferromagnetic coating. However, in one embodiment, the power source 30 could be positioned at the location of (or closely adjacent to) the ferromagnetic coating 65, and tuning could be achieved with electrical components, all within a single handheld, battery-powered instrument.

Alternatively, electrical components necessary for impedance matching can be located at the output stage of the amplifier 140. Such may involve the use of an autotuning circuit that automatically monitors power delivery and selects the optimal combination of electrical component values in order to maximize power delivery to the ferromagnetic coating. Further, electrical components, such as a capacitor or inductor, can be connected in parallel or series to the ferromagnetic coated conductor 60, at the location of the connection of the conductor wire 66 to the cable 150, in order to complete a resonant circuit.

For example, a processor may monitor power delivery, such as by monitoring standing wave ratio (SWR), and adjust electronically controlled capacitors, electronically controlled inductors, and/or electronically controlled resistors. In some embodiments, a matching circuit may be made more useful over a larger range of devices by including variable inductance, capacitance and/or resistance in the matching circuit. The matching circuit may thus be able to accommodate more surgical elements and/or more frequencies.

Dynamic load issues can be caused by the interaction of the ferromagnetic coated conductor 60 with various tissues. These issues may be minimized by the standing wave being maximized at the load location. Multiple different frequencies can be used, including frequencies from 5 megahertz to 24 gigahertz, preferably between 40 MHz and 928 MHz. In some regulated countries it may be preferable to choose frequencies in the ISM bands such as bands with the center frequencies of 6.78 MHz, 13.56 MHz, 27.12 MHz, 40.68 MHz, 433.92 MHz, 915 MHz, 2.45 GHz, 5.80 GHz, 24.125 GHz, 61.25 GHz, 122.5 GHz, 245 GHz. In one embodiment, the oscillator 130 uses an ISM Band frequency of 40.68 MHz, a class E amplifier 140, and a length of coaxial cable 150, all of which may be optimized for power delivery to a ferromagnetic coated tungsten conductor 60 with a ferromagnetic coating 65 consisting of a thickness of between about 0.05 micrometer and about 500 micrometers, and preferably between about 1 micrometer and about 50 micrometers. A useful estimate may be to start the ferromagnetic coating thickness at about 10% of the conductor diameter, and up to about 5 cm long. However, the ferromagnetic coating may be disposed as far along the length or along multiple regions of the conductor as where heating may be desired. (The ferromagnetic coating 65 may be formed from a Nickel Iron (NiFe) alloy, such as NIRON™ from Enthone, Inc. of West Haven, Conn., or other ferromagnetic coatings, including without limitation Co, Fe, $FeOFe_2O_3$, $NiOFe_2O_3$, $CuOFe_2O_3$, $MgOFe_2O_3$, MnBi, Ni, MnSb, $MnOFe_2O_3$, $Y_3Fe_5O_{12}$, $CrO_2$, MnAs, Gd, Dy, EuO, magnetite, yttrium iron garnet, aluminum, PERMALLOY™, and zinc.)

The size of the conductor, size of the ferromagnetic coating, associated thicknesses, shape, primary geometry, composition, power supply and other attributes may be selected based on the type of procedure and surgeon preferences. For example, a brain surgeon may desire a small instrument in a light handheld package designed for quick application within the brain, while an orthopedic surgeon may require a larger device with more available power for operation on muscle.

The conductor may be formed from copper, tungsten, titanium, stainless steel, platinum and other materials that may conduct electricity. Considerations for the conductor may include, but are not limited to, mechanical strength, thermal expansion, thermal conductivity, electrical conduction/resistivity, rigidity, and flexibility. It may be desirable to form the conductor wire 66 of more than one material. Connection of two dissimilar metals may form a thermocouple. If the thermocouple were placed in the vicinity of or within the ferromagnetic coating, the thermocouple may provide a temperature feedback mechanism for the device. Further, some conductors may have a resistivity that correlates to temperature, which may also be used to measure temperature.

The tuning of the power source 30 may also reduce the amount of high frequency energy radiating into the patient to near zero, as voltage is low, and ideally zero, at the location of the ferromagnetic coating 65. This is in contrast to monopolar devices, which require a grounding pad to be applied to the patient, or bipolar devices, both of which pass current through the tissue itself. The disadvantages of these effects are well known in the literature.

In many of these embodiments discussed herein, the combination of cable length, frequency, capacitance and inductance may also be used to adjust efficiency and tool geometry by tuning the power source 30 to deliver maximum power to the ferromagnetic coating 65, and therefore, maximum heat to the tissue. A tuned system also provides for inherent safety benefits; if the conductor were to be damaged, the system would become detuned, causing the power delivery efficiency to drop, and may even shut down if monitored by an appropriate safety circuit.

The amount of power delivered to the patient tissue may be modified by several means to provide precise control of tissue effects. The power source 30 may incorporate a modulator 120 for power delivery as described above. Another embodiment uses modification of the magnetic field by altering the geometry of the conductor wire 66 and the ferromagnetic coating 65 through which it passes, such as would be caused by a magnet. Placement of the magnet nearby the ferromagnetic coating 65 would similarly alter the induction effect and thereby change the thermal effect.

While modulation has been discussed as a method to control power delivery, other methods may be used to control power delivery. In one embodiment, the output power, and correspondingly the temperature, of the tool is controlled by tuning or detuning the drive circuit, including the conductor wire 66 and ferromagnetic coated conductor 60.

Figure 4A:
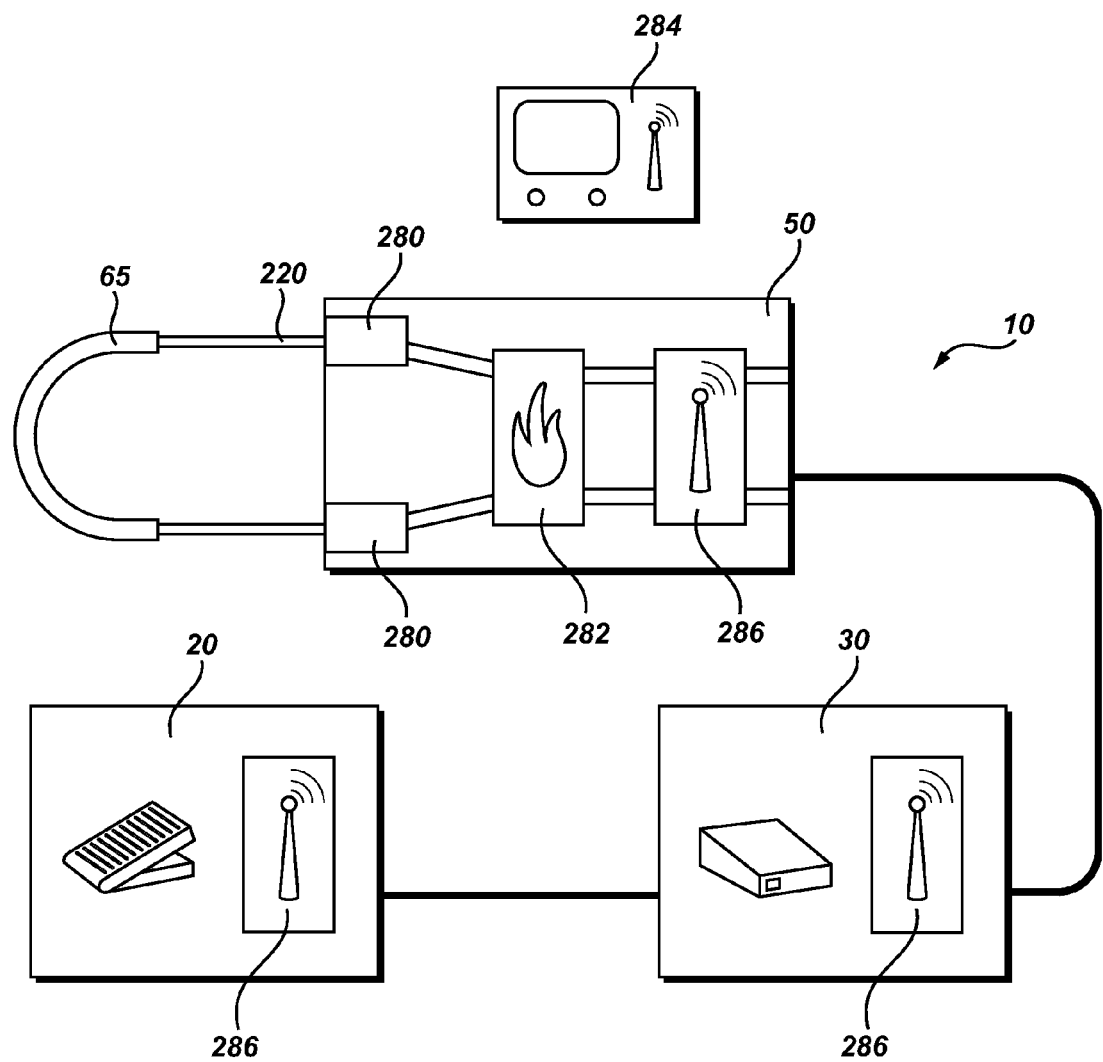
FIG. 4A shows a thermal surgical tool system with heat prevention terminals, a heat sink, and wireless communication devices.

Turning now to FIG. 4A, a thermal surgical tool system 10 with connectors which attach to opposing first and second ends of a wire conductor is shown. The conductors as shown in FIG. 4A may be formed by heat prevention terminals 280, such as crimp connectors that provide thermal isolation. One or more heat sinks 282, and wireless communication devices 286 may also be included. The wire conductor 220 may be connected to the handheld surgical tool 50 by terminals 280 and/or a heat sink 282 at opposing first and second ends of the conductor. Portions of the conductor may extend into the handle into terminals 280, while the ferromagnetic coating portion of the conductor may extend beyond the handle. The terminals 280 may have a poor thermal conductance such that the terminals 280 reduce the heat transfer from the conductor into the handheld surgical tool 50. In contrast, the heat sink 282 may draw any residual heat from the terminals 280 and dissipate the heat into other mediums, including the air. Connectors and connections may also be achieved by wire bonding, spot and other welding, in addition to crimping.

Preventing thermal spread may be desirable because the other heated portions of the handheld surgical tool 50 may cause undesired burns, even to the operator of the handheld surgical tool 50. In one embodiment, terminals 280 are used to conduct the electric current, but prevent or reduce thermal conduction beyond the ferromagnetic coated conductor.

The thermal surgical tool may also communicate wirelessly. In one embodiment, the user interface for monitoring and adjusting power levels may be housed in a remote, wirelessly coupled device 284. The wirelessly coupled device may communicate with a wireless module 286 contained within the thermal surgical tool system 10, including the handheld surgical tool 50, the control system (such as foot pedal 20), and/or the power subsystem 30. By housing the control interface and display in a separate device, the cost of the handheld surgical tool 50 portion may be decreased. Similarly, the external device may be equipped with more processing power, storage and, consequently, better control and data analysis algorithms.

Figure 4B:
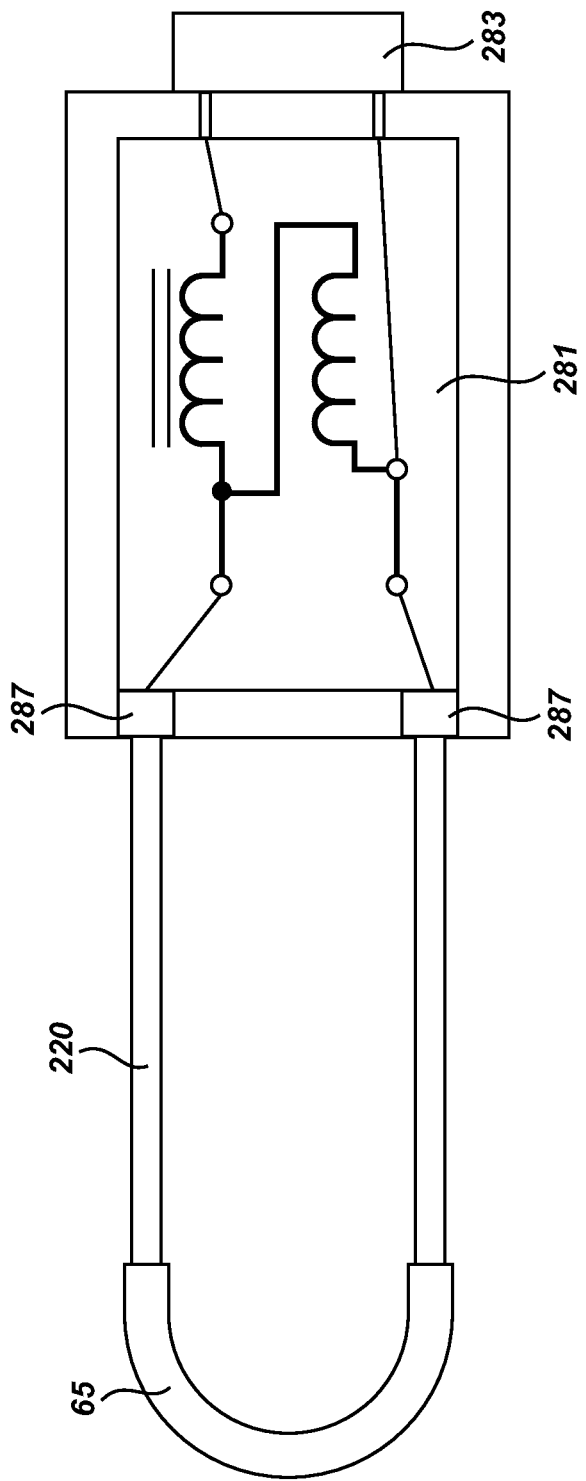
FIG. 4B shows a thermal surgical tool system with an impedance matching network.

Turning now to FIG. 4B, a thermal surgical tool system with an impedance matching network is shown. The impedance matching network may match the output impedance of the signal source to the input impedance of the load. This impedance matching may aid in maximizing power and minimizing reflections from the load.

In one embodiment, the impedance matching network may be a balun 281. This may aid in power transfer as the balun 281 may match the impedance of the ferromagnetic coated conductor terminals 287 to the amplifier cable terminals 283 (shown here as a coaxial cable connection). In such a configuration, some baluns may be able to act as a heat sink and provide thermal isolation to prevent thermal spread from the thermal energy at the ferromagnetic coating 65 transferred by the wire conductor 220 to terminals 287. The appropriate matching circuitry may also be placed on a ceramic substrate to further sink heat away or isolate heat away from the rest of the system, depending on the composition of the substrate.

It should be recognized that the elements discussed in FIGS. 4A and 4B can be used in conjunction with any of the embodiments shown herein.

Figure 5:
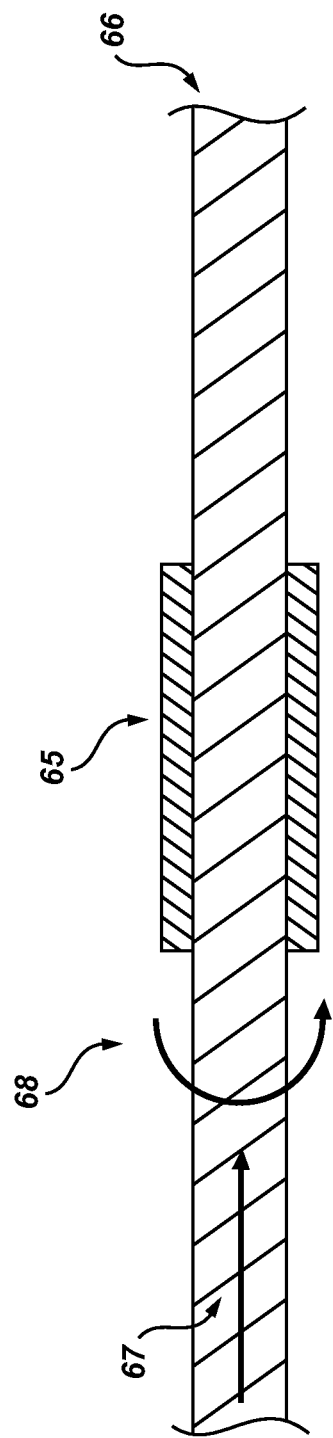
FIG. 5 shows a close-up, side cross-sectional view of a single layer ferromagnetic coated conductor tip in accordance with one aspect of the present invention.

Turning now to FIG. 5, a longitudinal cross section of the ferromagnetic coated conductor is shown. As an alternating current 67 is passed through conductor 66, a time varying magnetic field 68 is induced around conductor 66. The time varying magnetic field 68 is resisted by the ferromagnetic coating 65, causing the ferromagnetic coating 65 to dissipate the inductive resistance to the time varying magnetic field 68 as heat. Should the ferromagnetic coating 65 reach it's Curie point, the magnetic resistive properties of ferromagnetic coating 65 become substantially reduced, resulting in substantially decreased resistance to time varying magnetic field 68. As there is very little mass to the ferromagnetic coating 65, the magnetic field causes the ferromagnetic coating 65 to quickly heat. Similarly, the ferromagnetic coating 65 is small in mass compared to conductor 66 and therefore heat will quickly dissipate therefrom due to thermal transfer from the hot ferromagnetic coating 65 to the cooler and larger conductor 66, as well as from the ferromagnetic coating 65 to the surrounding environment.

It should be appreciated that while the figures show a solid circular cross-section, the conductor cross-section may have various geometries. For instance, the conductor may be a hollow tubing such that it reduces thermal mass. Whether solid or hollow, the conductor may also be shaped such that it has, for example, an oval, triangular, square or rectangular cross-section.

As is also evident from FIG. 5, the ferromagnetic coating may be between a first section (or proximal portion) and a second section (or distal portion) of the conductor. This may provide the advantage of limiting the active heating to a small area, instead of the entire conductor. A power supply may also connect to the first and second section to include the ferromagnetic coating within a circuit providing power.

A method of using the surgical tool may include the steps of: selecting a conductor and plating a ferromagnetic coating upon the conductor. Optional steps to the method may include: selecting a size of a conductor having a ferromagnetic coating disposed on a portion thereof according to a desired procedure; selecting a thermal mass of a conductor having a ferromagnetic coating disposed on a portion thereof according to a desired procedure; selecting a conductor from the group of loop, solid loop, square, pointed, hook and angled; configuring the oscillating electrical signal to heat the coating to between about 37 and about 600 degrees Centigrade; configuring the oscillating electrical signal to heat the coating to between about 40 and about 500 degrees Centigrade; causing the coating to heat to between about 58-62 degrees Centigrade to cause vascular endothelial welding; causing the coating to heat to between about 70-80 degrees Centigrade to promote tissue hemostasis; causing the coating to heat to between about 80-200 degrees Centigrade to promote tissue searing and sealing; causing the coating to heat to between about 200-400 degrees Centigrade to create tissue incisions; or causing the coating to heat to between about 400-500 degrees Centigrade to cause tissue ablation and vaporization. Treatment may include incising tissue, causing hemostasis, ablating tissue, or vascular endothelial welding.

Figure 6:
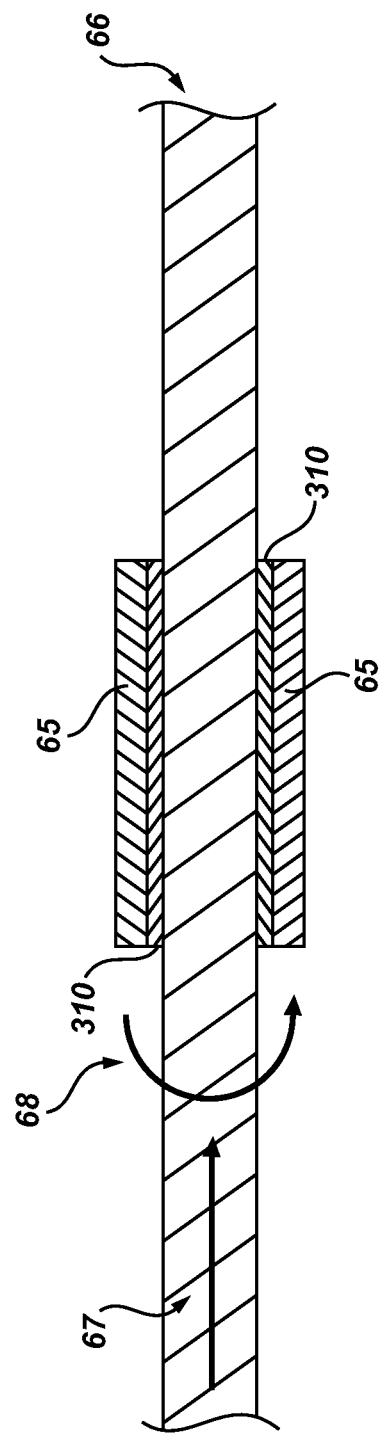
FIG. 6 shows a close-up, side cross-sectional view of a single layer ferromagnetic coated conductor tip with a thermal insulator in accordance with one aspect of the present invention.

Turning now to FIG. 6, a close-up, longitudinal cross-sectional view of a single layer cutting tip with a thermal insulator 310 is shown. A layer of thermal insulator 310 may be placed between the ferromagnetic coating 65 and the conductor 66. Putting a layer of thermal insulator 310 may aid in the quick heating and cool-down (also known as thermal response time) of the tool by reducing the thermal mass by limiting the heat transfer to the conductor 66.

The thickness and composition of the thermal insulator may be adjusted to change the power delivery and thermal response time characteristics for a desired application. A thicker coating of thermal insulator 310 may better insulate the conductor 66 from the ferromagnetic coating 65, but may require increased power compared with a thinner coating of thermal insulator 310 to induce a magnetic field sufficient to cause the ferromagnetic coating to heat.

The embodiments shown in FIGS. 7A through 7G include a plurality of surgical tips 210 comprising a wire conductor 220 which has a portion of its length coated with a relatively thin layer of ferromagnetic coating 65. As shown in FIGS. 7A through 7G, the ferromagnetic coating 65 may be a circumferential coating around a wire conductor 220. When the wire conductor 220 is excited by a high frequency oscillator, the ferromagnetic coating 65 will heat through induction according to the power delivered, with an absolute limit provided by its Curie temperature. Because of the small thickness of ferromagnetic coating 65 and the tuned efficiency of high frequency electrical conduction of the wire at the position of the ferromagnetic coating 65, the ferromagnetic coating 65 will heat very quickly (e.g. a small fraction of a second) when the current is directed through the wire conductor 220, and cool down quickly (e.g. a fraction of a second) when the current is stopped.

FIGS. 7A, 7B, 7C, 7D, 7E, 7F and 7G show ferromagnetic coated conductor surgical tips 210a, 210b, 210c, 210d, 210e, 210f and 210g, respectively. In each of these embodiments, a portion of wire conductor 220 is bent and coated with a ferromagnetic coating 65 such that the ferromagnetic coating 65 is only exposed to tissue where the desired heating is to occur. FIGS. 7A and 7B are loop shapes that can be used for tissue cutting or excision, depending upon the orientation of the tool to the tissue. FIG. 7A shows a rounded geometry, while FIG. 7B shows a squared geometry. FIG. 7C shows a pointed geometry for heated tip applications that can be made very small because the process of tissue dissection, ablation, and hemostasis requires only a small contact point. FIG. 7D shows an asymmetric tool with a loop geometry, where the ferromagnetic coating 65 is only disposed on one side of the tool. FIG. 7E shows a hook geometry where the ferromagnetic coating 65 is disposed on the concave portion of the hook. FIG. 7F shows a hook geometry where the ferromagnetic coating 65 is disposed on the convex portion of the hook. FIG. 7G shows an angled geometry, which may be used in similar situations as a scalpel. Use of these various geometries of ferromagnetic coating 65 upon a wire conductor 220 may allow the surgical tip to act very precisely when active and to be atraumatic when non-active. It will be appreciated that the geometry of the ferromagnetic coated conductor surgical tips shown in FIGS. 7A through 7G are only illustrative, and that ferromagnetic coated conductor surgical tips having alternate geometries may be used.

In one representative embodiment, the electrical conductor may have a diameter of about 0.01 millimeter to about 1 millimeter and preferably about 0.125 to about 0.5 millimeters. The electrical conductor may be tungsten, copper, other metals and conductive non-metals, or a combination such as two dissimilar metals joined to also form a thermocouple for temperature measurement. The electrical conductor may also be a thin coating of conductor, such as copper, dispersed around a non-metallic rod, fiber or tube, such as glass or high-temperature plastic, and the conductive material, in turn, may be coated with a thin layer of ferromagnetic material. The magnetic film forms a closed magnetic path around the electrically conductive wire. The thin magnetic film may have a thickness of about 0.01% to about 50% and preferably about 0.1% to about 20% of the cross-sectional diameter of the wire. Due to the close proximity of the coating to the wire, a small current can produce high magnetic fields in the coating and result in significant temperatures. Since the magnetic permeability of the film is high and it is tightly coupled to the electrical conductor, low levels of current can result in significant hysteresis losses.

It is therefore possible to operate at high frequencies with low alternating current levels to achieve rapid inductive heating up to the Curie point. The same minimal thermal mass allows rapid decay of heat into tissue and/or the conductor with cessation of current. The tool, having low thermal mass, provides a rapid means for temperature regulation across a therapeutic range between about 37 degrees Celsius and about 600 degrees Celsius, and preferably between about 40 and about 500 degrees Celsius.

While Curie point has been previously described as a temperature cap, a material with a Curie point beyond the anticipated therapeutic need may be selected and the temperature regulated below the Curie point according to one aspect of the present invention.

Figure 8:
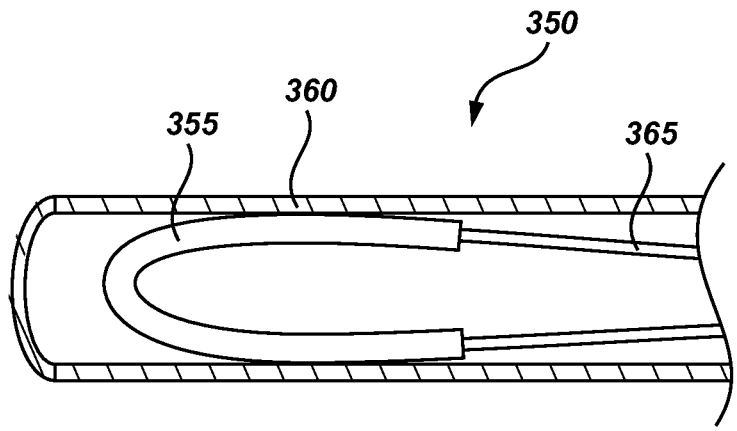
FIG. 8 shows a cut-away view of a retracted snare.

Turning now to FIG. 8, a cut-away view of a snare 350 in a retracted position is shown. A ferromagnetic coating is placed on a conductor to form a snare loop 355 and then placed within a sheath 360. While retracted, the snare loop 355 may rest within the sheath 360 (or some other applicator, including a tube, ring or other geometry designed to reduce the width of the snare when retracted). The sheath 360 may compress the snare loop 355 within its hollow body. The sheath 360 may then be inserted into a cavity where the target tissue may be present. Once the sheath 360 reaches the desired location, the snare loop 355 may be extended outside the sheath 360, and end up deployed similar to FIG. 9A. In one embodiment, the conductor 365 may be pushed or pulled to cause extension and retraction of the snare loop 355.

Figure 9A:
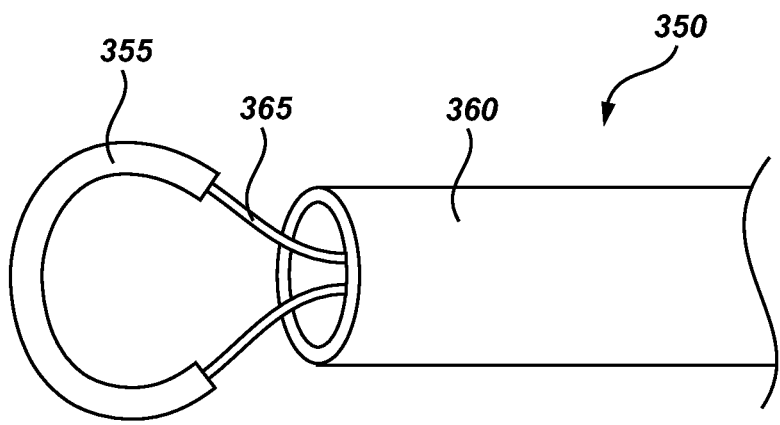
FIG. 9A shows a side view of an extended snare.

Turning now to FIG. 9A, a side view of a snare 350 in an extended position is shown. Once extended, the snare 355 loop may be used in several different ways. In one embodiment, the snare loop 355 may be placed substantially around the target tissue, such that the tissue is within the snare loop 355. The ferromagnetic coating may then be caused to be inductively heated as discussed above. The snare loop 355 is then retracted back into the sheath 360 such that the target tissue is separated and removed from tissue adjacent the target tissue. The desired temperature range or power level may be selected for hemostasis, increased tissue separation effectiveness or other desired setting. For example, in one embodiment, the snare 350 is configured for nasal cavity polyp removal.

In another use, the snare 350 may be configured for tissue destruction. Once within the desired cavity, the snare may be extended such that a portion of the snare loop 355 touches the target tissue. The snare loop 355 may then be inductively heated such that a desired tissue effect occurs. For example, in one embodiment, the sheath may be placed near or in the heart and the snare loop 355 inductively heated to cause an interruption of abnormal areas of conduction in the heart, such as in atrial ablation.

Figure 9B:
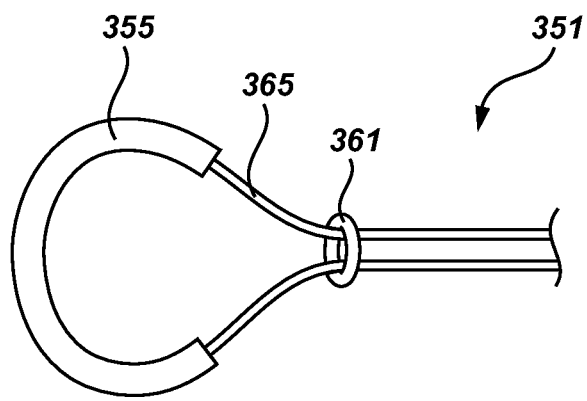
FIG. 9B shows an alternate embodiment of an extended snare.

Turning now to FIG. 9B, an alternate embodiment of a snare 351 is shown. The applicator may be a ring 361 instead of a sheath as in FIG. 9A. Similar to the sheath, the ring 361 may be used to force the loop 355 into an elongated position. Various devices could be used to hold the ring 361 in place during use.

A method of separating tissue may include the steps of: selecting a conductor having a ferromagnetic coating disposed on a portion thereof; placing the portion of the conductor having the ferromagnetic coating within a tube; inserting the tube into a cavity; deploying the portion of the conductor having the ferromagnetic coating within the cavity; and delivering an oscillating electrical signal to the conductor so as to heat the ferromagnetic coating while the heated ferromagnetic coating is in contact with a target tissue.

Optional steps may include: the deploying step further comprising placing the ferromagnetic coating substantially around the target tissue; retracting the ferromagnetic coating portion of the conductor into the tube; causing hemostasis in the target tissue; forming the conductor into a bent geometry such that a portion of the conductor remains within the tube; and touching a ferromagnetic covered portion of the bent geometry to the target tissue.

A method of removing tissue may include the steps of: selecting a conductor having at least one portion having a ferromagnetic conductor disposed thereon; and placing the ferromagnetic conductor around at least a portion of the tissue and pulling the ferromagnetic conductor into contact with the tissue so that the ferromagnetic conductor cuts the tissue.

Optional steps may include: using a conductor having a plurality of ferromagnetic conductors in an array or passing an oscillating electrical signal through the conductor while the ferromagnetic material is in contact with the tissue.

Figure 10A:
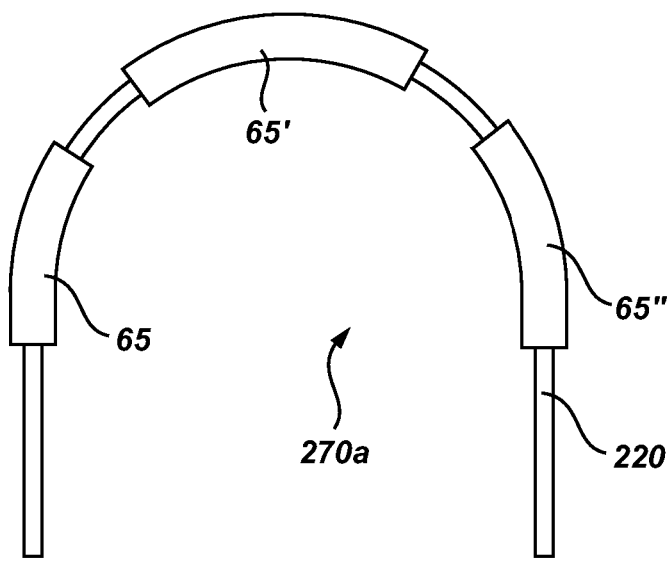
FIG. 10A shows a close-up view of a ferromagnetic coated conductor surgical tool with a loop geometry and linear array of coatings.

Turning now to FIG. 10A, a close-up view of a cutting tip with a loop geometry and linear array of coatings is shown. While the above embodiments have disclosed a continuous ferromagnetic coating on a conductor, in another embodiment, there may be more than one coating separated by gaps on a single conductor. This is termed a linear array of ferromagnetic elements (an example of a parallel array of ferromagnetic elements can be seen in FIGS. 18A-18C).

Figure 10B:
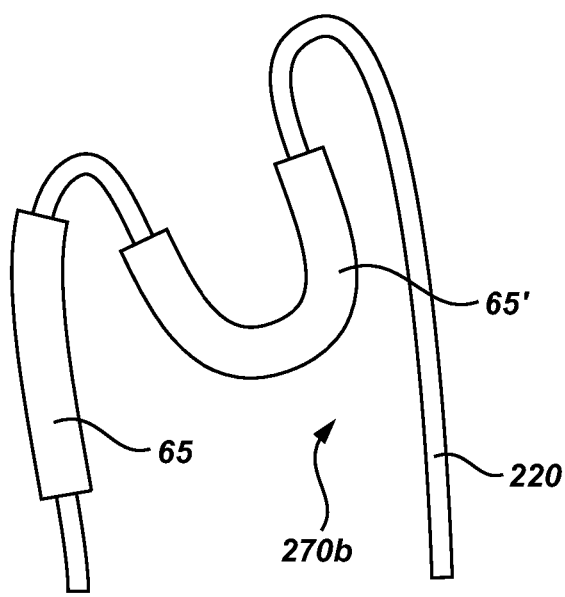
FIG. 10B shows a close up view of a ferromagnetic coated conductor surgical tool with an alternate hook geometry and linear array.

In one embodiment, a loop geometry 270a may have multiple ferromagnetic coatings 65, 65', and 65" which are separated by gaps on a wire conductor 220. In another embodiment shown in FIG. 10B, a close up view of a cutting tip with an alternate hook geometry 270b and linear array of ferromagnetic coatings 65 and 65' is shown on a wire conductor 220. The linear array may include the advantage of allowing flexibility in building a desired thermal geometry.

The conductor 66 which may be formed of an alloy having shape memory, such as Nitinol (nickel titanium alloy). A Nitinol or other shape memory alloy conductor can be bent into one shape at one temperature, and then return to its original shape when heated above its transformation temperature. Thus, a physician could deform it for a particular use at a lower temperature and then use the ferromagnetic coating to heat the conductor to return it to its original configuration. For example, a shape memory alloy conductor could be used to form a snare which changes shape when heated. Likewise, a serpentine shape conductor can be made of Nitinol or other shape memory alloy to have one shape during use at a given temperature and a second shape at a higher temperature. Another example would be for a conductor which would change shape when heated to expel itself from a catheter or endoscope, and then enable retraction when cooled.

In another embodiment, the ferromagnetic coatings may be formed in such a way that one or more coatings among the linear array may receive more power by tuning the oscillating electrical energy. The tuning may be accomplished by adjusting the frequency and/or load matching performed by the power source to specific ferromagnetic coatings.

Figure 11:
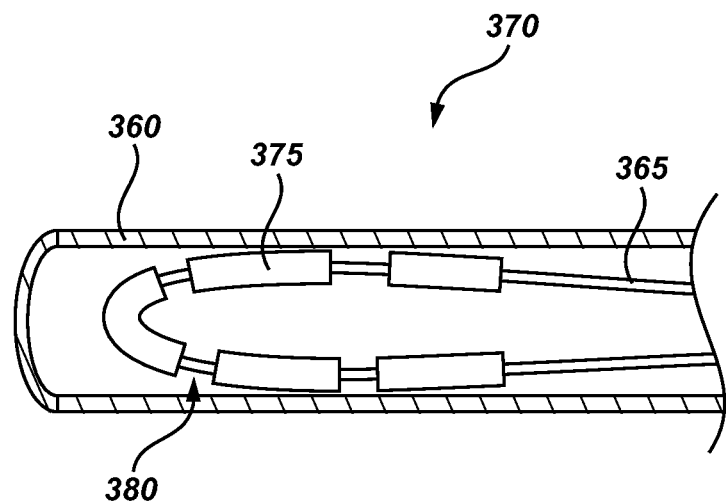
FIG. 11 shows a cut-away view of a retracted snare with an array of coatings.

Turning now to FIG. 11, a cut-away view of a snare tool 370 with a linear array of coating segments 375 in a retracted position is shown. In some embodiments, some ferromagnetic coatings may lack the elasticity to effectively bend into a retracted position. Therefore, individual coating segments 375 may be separated by gaps 380 such that the conductor 365 may be flexed while the coating segments 375 may remain rigid.

Figure 12:
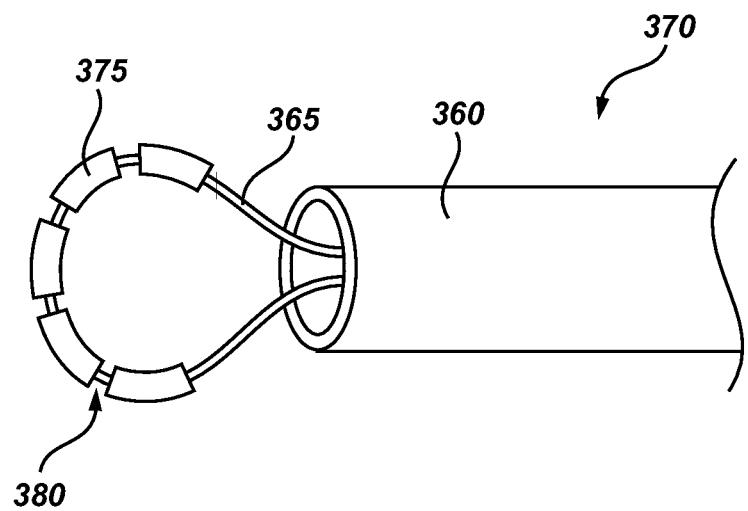
FIG. 12 shows a side view of an extended snare with a linear array of coatings.

Similarly, the snare tool 370 may be extended, as seen in FIG. 12. The gaps 380 between the coating segments 375 may be adjusted such that the heating effect will be similar in the gaps 380 as the coating segments. Thus, the snare tool 370 with linear array may act similar to the snare with flexible coating in FIGS. 8 and 9.

Turning now to FIG. 13, a cross-sectional view of a single layer cutting tip in the ferromagnetic-coated region is shown. The ferromagnetic coating 65 is disposed over a wire conductor 220. The ferromagnetic coating 65 provides several advantages. First, the ferromagnetic coating 65 is less fragile when subjected to thermal stress than ferrite beads, which have a tendency to crack when heated and then immersed in liquid. The ferromagnetic coated conductor 60 (See e.g., FIG. 1) has been observed to survive repeated liquid immersion without damage. Further, the ferromagnetic coating 65 has a quick heating and quick cooling quality. This is likely because of the small amount of ferromagnetic coating 65 that is acted upon by the magnetic field, such that the power is concentrated over a small area. The quick cooling is likely because of the small amount of thermal mass that is active during the heating. Also, the composition of the ferromagnetic coating 65 may be altered to achieve a different Curie temperature, which would provide a maximum self-limiting thermal ceiling attribute to the device.

Turning now to FIGS. 14A, 14B and 15, a multilayer surgical tool tip is shown. A cross section of 14A along the 221 line may result in FIG. 14B which shows alternating layers of wire conductor 220 and 220' and ferromagnetic coating 65 and 65'. Heating capacity may be increased by layering thin layers of alternating conductor 220 and 220' material and ferromagnetic coating 65 and 65', while still maintaining quick heating and cooling advantages. FIG. 15 shows an axial cross-sectional view from FIG. 14A along the 390 line. The alternating layers of conductor 220 and 220', and ferromagnetic coating 65 and 65' may also be seen.

Figure 16:
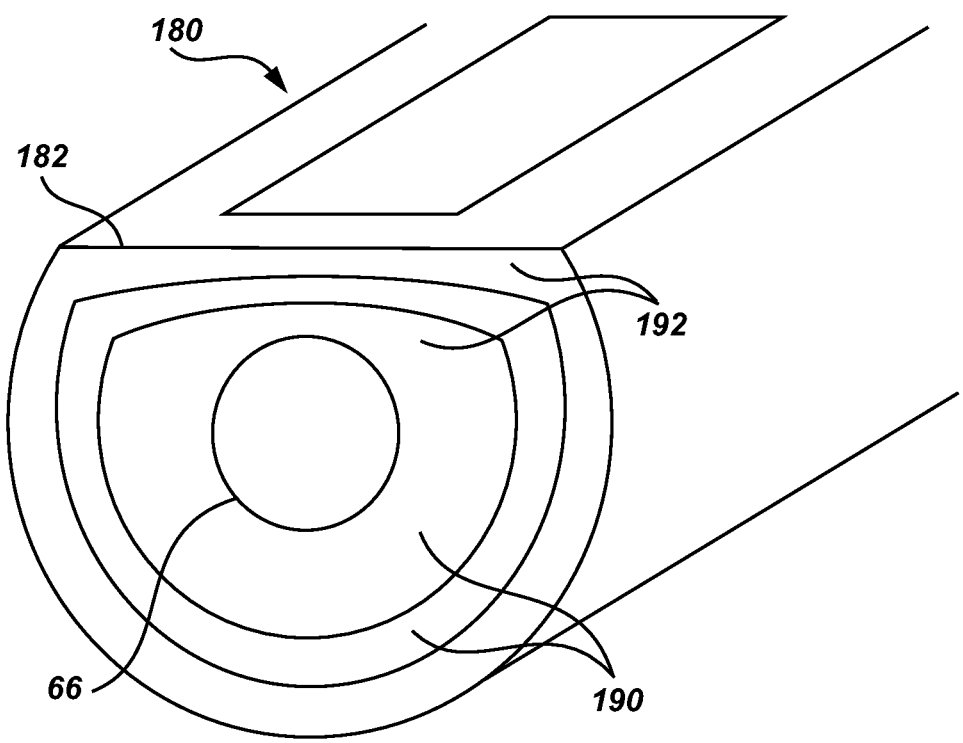
FIG. 16 shows a cross-sectional view of a flattened side cylindrical geometry ferromagnetic coated conductor showing electromagnetic lines of flux.

Turning now to FIG. 16, a flattened side cylindrical geometry is shown. The flat surface 180 can be manufactured to cause a thin plating 182 of ferromagnetic coating on the conductor 66 relative to the thicker plating around the rest of the conductor 66. This thin plating 182 may result in selective first onset heating in this flat surface 180. Inductive heating may be proportional to flux density within the magnetically permeable coating. In one embodiment, an asymmetrically thinned coating has a small cross sectional thickness and may generate higher hysteresis losses in the form of heat. Thus, a therapeutic temperature may be achieved with yet lower power at the flat surface 180 with higher flux density 192 compared to a cooler opposite side with a diminished flux density 190. An advantage is that fast temporal response and distributed optimal heating at the tissue interface may be enhanced.

Figure 17:
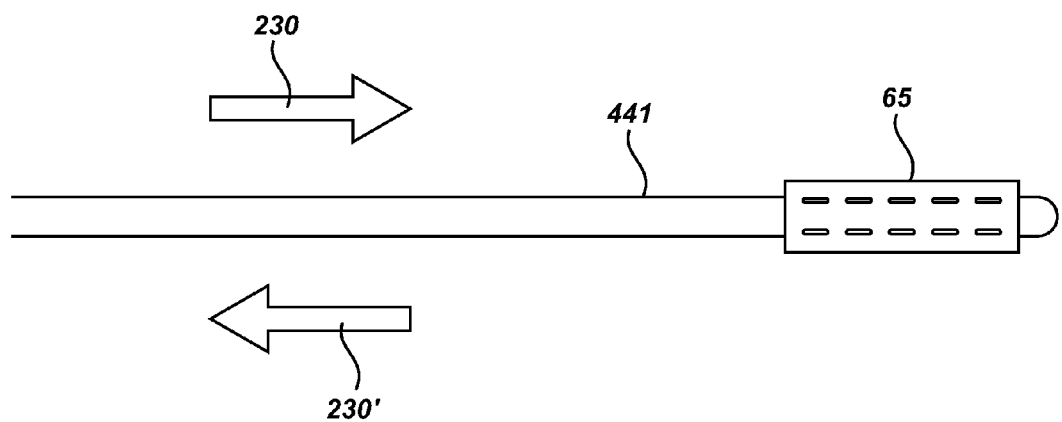
FIG. 17 shows a closed conductor tip in accordance with another aspect of the present invention.

Turning now to FIG. 17, the ferromagnetic coating 65 may also be configured to focus the temperature increase on the outside of the ferromagnetic coating 65, further reducing the time needed to cool the ferromagnetic coating 65 in a relatively high power application. An example of such a configuration is shown in FIG. 17, wherein the fields generated by the current flow 230 and 230' (the arrows) may have a cancelling effect with respect to each other within the ferromagnetic coating 65 surrounding both conductors, keeping the ferromagnetic material between the looped conductor 441 cooler than the ferromagnetic material at the perimeter.

Turning now to FIGS. 18A through 18D, several surgical tip 194 geometries are demonstrated. In FIG. 18A, a surgical tip 194a with a single small diameter electrically conductive wire plated with the thin film magnetic material 196 is shown. In FIG. 18B, the surgical tip 194b with two small diameter electrically conductive wires plated with the thin film magnetic material 196' is shown. In FIG. 18C, a surgical tip 194c with three small diameter electrically conductive wires plated with the thin film magnetic material 196" are shown. It is thus contemplated that a tip geometry may consist of a plurality of small diameter electrically conductive wires plated with the thin film magnetic material. Such a design maintains the temporal heat responsiveness (rapid onset, rapid offset) essential to the dynamic surgical environment due to minimal mass of the ferromagnetic coated conductor(s). It is thus possible to configure a flat tine with two or more spaced wires as a practical monothermal or multithermal tool. Further, the tips 194a, 194b and 194c may also be exchangeable as seen in FIG. 18D, which has a receptacle 198 for the tips 194a, 194b and 194c in FIGS. 18A through 18C. It will be appreciated that the generator system may be configured to adjust the power jointly delivered to two or more of the conductors and that a user control (as shown in other figures) can be provided for that purpose.

The ferromagnetic coating 65 can be used to contact the tissue directly, or, a non-stick coating, such as TEFLON (PTFE), or similar material, could be applied over the ferromagnetic coating and conductor to prevent sticking to the tissue. Alternatively, the ferromagnetic coating could be coated with another material, such as gold, to improve biocompatibility, and/or polished, to reduce drag force when drawing through tissue. The ferromagnetic coating could also be coated by a thermally-conductive material to improve heat transfer. In fact, a single coating may be selected to have multiple desirable properties.

Turning now to FIGS. 19A through 22C, the ferromagnetic coated conductor may be attached to a primary geometry. The primary geometry may provide an attachment surface or an internal site for the conductor with a ferromagnetic coating. Thus the advantages of the ferromagnetic coating on a conductor may be combined with the advantages of the primary geometry and its corresponding material. The primary geometry may be selected for various reasons, including but not limited to, material strength, rigidity, heat conduction, resistance to thermal heat transfer, surface area, or additional functionality.

As used herein, a primary geometry means a structure to which a ferromagnetic coated conductor may be attached and which defines the shape of the tool. For example, a primary geometry could be a scalpel, tines of forceps, the face of a spatula, or a ball shape at the end of a probe. The conductor geometry, therefore, may be disposed upon the primary geometry, may extend through a hole in the primary geometry, and/or be embedded in the primary geometry. For example, a primary geometry may be a scalpel, while the conductor geometry may be the serpentine shape of a ferromagnetic coated wire upon the primary geometry.

Figure 19A:
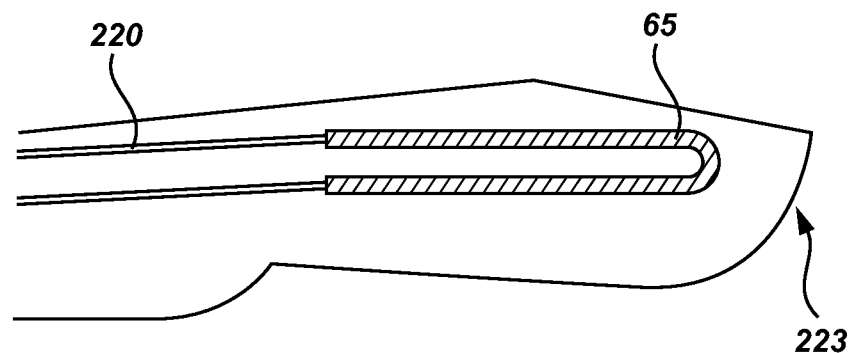
FIG. 19A shows a normally cold cutting scalpel with alternate inductive ferromagnetic thermal function.
Figure 19B:
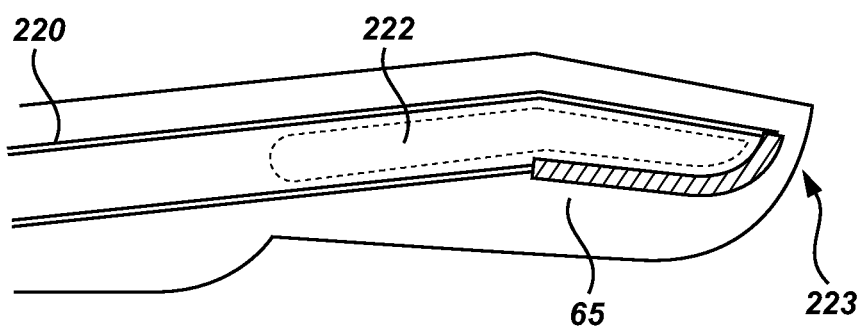
FIG. 19B shows an alternate embodiment of a normally cold cutting scalpel with alternate inductive ferromagnetic thermal function.

Referring to FIGS. 19A and 19B, a cold cutting scalpel 223 with alternate inductive ferromagnetic thermal function is shown. The cold cutting scalpel 223 may be used for cutting through the application of a blade having a cutting edge and having a secondary thermal function activated when required, such as for coagulation. In the embodiments shown in FIGS. 19A and 19B, this is achieved by placing a ferromagnetic coated wire conductor 220 upon the side of a scalpel shaped primary geometry, which can cut tissue without activation of the conductor or ferromagnetic coating 65. The cold cutting scalpel 223 may be used classically to make incisions in tissue. However, if the patient begins to bleed, the cold cutting scalpel 223 operator may activate the ferromagnetic coated conductor and place the side of the cold cutting scalpel 223 (and correspondingly, the ferromagnetic coated conductor) upon the bleeding tissue. The thermal effect may then cause the tissue to seal and cease bleeding. After deactivation of the ferromagnetic coated conductor, the scalpel operator may then return to making incisions with the benefits of the cold cutting scalpel 223.

There are several advantages to the use of such a cold cutting scalpel 223. The dual-use tool does not require the cold cutting scalpel 223 operator to remove one tool and replace it with another, causing risk of further damage and delay. Due to the ferromagnetic coating 65, the cold cutting scalpel 223 may also have a quick thermal response time (the heat-up and cool-down time) in the region of the ferromagnetic coating 65 such that the cold cutting scalpel 223 may be used on the targeted area and reduce waiting time. In cases where it may be desirable to heat the entire cold cutting scalpel, thermal response time may be further reduced by removing a center portion 222 of the blade (as seen in FIG. 19B), resulting in a non-contiguous portion of the blade that may occur between or adjacent to the conductor path. Removing the center portion 222 of the blade may further reduce the thermal mass and correspondingly the thermal response time.

In one embodiment, related to FIG. 19B, the ferromagnetic coating may be limited to a part of the scalpel, such as the tip of the cold cutting scalpel 223. This limiting would cause only the tip to heat, while the remaining portions of the primary geometry would remain at a lower temperature. This limiting of the heating to a portion of the primary geometry in proximity to the ferromagnetic coating may provide a higher degree of accuracy and usefulness in smaller spaces. Similarly, the ferromagnetic coated wire conductor 220 may form a pattern, such as a zigzag or serpentine pattern, across the surface of the cold cutting scalpel 223 to increase the heating coverage of the surface.

Scalpel effects may also be enhanced by the thermal effects of the ferromagnetic coated wire conductor 220. In one embodiment, the scalpel may have multiple parts with different temperature ranges addressable to each part. For example, energy to the scalpel blade may be used to cut, while energy to the sides of the blade may be used to coagulate tissue walls. In another embodiment, the ferromagnetic coated wire conductor 220 may be activated to provide additional cutting ability when moving through more difficult tissue. In another embodiment, the ferromagnetic coated conductor may be activated to provide a more smooth cutting process in conjunction with the scalpel blade. A user control may be used to select a power setting to be delivered by a power source, which may be correlated with a desired temperature or tissue effect.

Turning now to FIG. 20A, a thermal surgical tool with a spatula shaped geometry is shown. The spatula 224 may have a ferromagnetic coating 65 on a wire conductor 220 that follows the perimeter of the spatula shape as shown. In an alternate embodiment, the ferromagnetic coated portion of the wire conductor 220 may form a pattern across the surface of the geometry such that the surface is more evenly covered by the ferromagnetic coated portion of the wire conductor 220.

A spatula geometry may be useful for various tissue effects and procedures. In one embodiment, the spatula is used for hemostasis or tissue welding during surgery. After an incision has been made, if needed, the spatula may be applied to the incised tissue to achieve hemostasis or even tissue welding. In another embodiment, the spatula is pressed into tissue and thermal energy is used for tissue ablation.

Turning now to FIG. 20B, the thermal surgical tool with a spatula shaped geometry is shown in forceps form. The spatula forceps 225 may be used in combination such that each spatula has a separate power control or the forceps may have a power control in common. Such a tool can be used to clamp vessels to stop blood flow, and then cause hemostasis and cutting of the vessels with heat.

Turning now to FIGS. 20C and 20D, a side view of FIG. 20A is shown in two different embodiments. The ferromagnetic coating and wire conductor may be attached to the primary geometry in several ways. In one embodiment shown in 20C, the ferromagnetic coating 65 and conductor may be attached to the surface of the primary geometry. Alternatively in 20D, the ferromagnetic coating 65 and conductor may be embedded within the primary geometry. Depending upon the desired effect, the tools depicted in FIGS. 20A, 20B, 20C and 20D can be applied to tissue in such a manner that the side of the tool on which the ferromagnetic coated conductor 65 is located can contact the tissue, or the opposite side can be applied to the tissue.

Turning now to FIGS. 21A, 21B and 21C, thermal surgical tools with ball-shaped geometries are shown. A horizontally wrapped ball 226 or a vertically wrapped ball 231 may be internally or externally wrapped with a wire conductor 220 with a ferromagnetic coating 65 as seen in FIG. 21A and FIG. 21C. FIG. 21B shows a ball geometry 227 which may contain a wire conductor 220 with a ferromagnetic coating prepared in another shape, such as a horseshoe shape. A ball-shaped heating element, examples of which have been provided in FIGS. 21A through 21C, may be formed which can be used to coagulate or provide a therapeutic effect over a large surface area of tissue. The ball may also be effective in tissue ablation, as it may radiate thermal energy in most, if not all, directions.

Figure 22A:
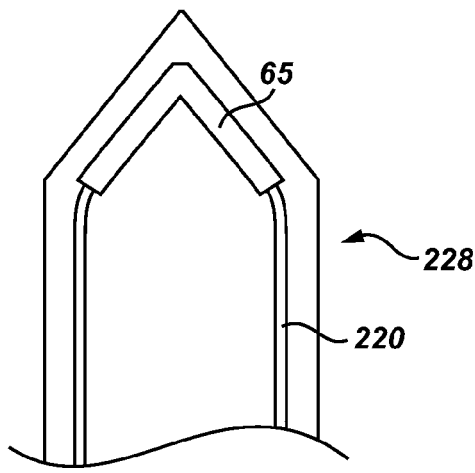
FIG. 22A shows a thermal surgical tool with a pointed geometry.

Turning now to FIG. 22A, a thermal surgical tool with a pointed geometry is shown. The pointed tool 228 may have a ferromagnetic coating 65 on a wire conductor 220 that follows the perimeter of the pointed tool shape as shown. In an alternate embodiment, the ferromagnetic coated portion of the wire conductor 220 may form a pattern across the point surface of the geometry such that the point surface is more evenly covered by the ferromagnetic coated portion of the wire conductor 220. The pointed tool 228 may be particularly useful for making incisions that penetrate layers of tissue providing a means for coagulation while cutting, such as coagulation of tissue around the site of trocar insertion for laparoscopic surgery.

Figure 22B:
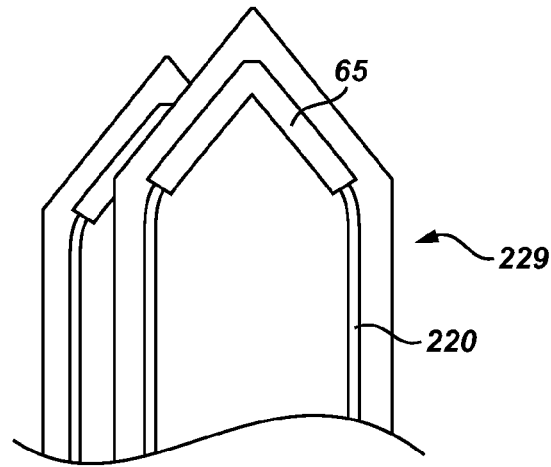
FIG. 22B shows a thermal surgical tool with a pointed geometry in a forceps configuration.

Turning now to FIG. 22B, the thermal surgical tool with a pointed geometry is shown in forceps form. The pointed forceps 229 may be used in combination such that each pointed geometry has a separate power control or the forceps may have a power control in common. Such a tool can be configured for achieving hemostasis and cutting in small vessel ligation.

While some primary geometries have been shown in singular form, the primary geometries may be used in combination. This may include two or more of the same primary geometry or differing primary geometries, including forceps applications. Each primary geometry may be commonly controlled for power or have separate power controls for each primary geometry. Furthermore, solid primary geometries may be altered similar to the scalpel primary geometry shown above such that portions of the primary geometries may be removed to reduce thermal mass and correspondingly, thermal response time.

While some of the primary geometries have been shown to have symmetrical construction, the primary geometries may have asymmetrical or directional construction such that only a portion of the primary geometry would be active. This may be accomplished by placing the ferromagnetic coating only on the portion of conductor wire residing on the area of the primary geometry desired to be active. For example, the spatula geometry may be configured to be active in one area if the ferromagnetic coated conductor is not symmetrically positioned on the spatula structure. This may be further enhanced by providing a pattern, such as a zigzag or serpentine pattern, on the desired active portion of the geometry.

Figure 22C:
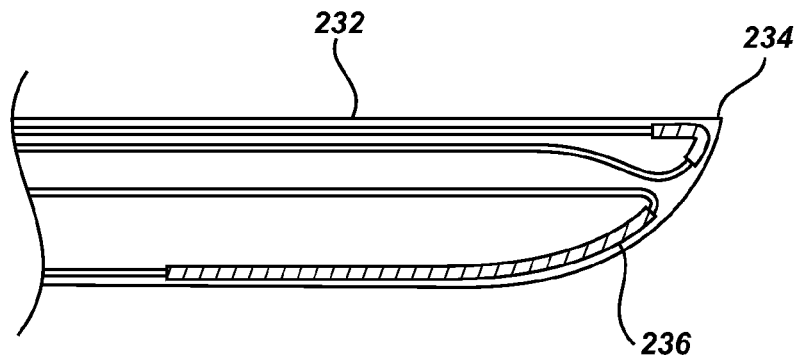
FIG. 22C shows a thermal surgical tool having two different activatable thermal zones.

In another embodiment, a portion of the primary geometry may be activated. By using multiple conductors with a ferromagnetic coating 65 attached to different portions of a primary geometry, a portion of the primary geometry may be selectively activated. For example, a scalpel geometry 232 may be divided into a tip portion 234 and a face portion 236 as shown in FIG. 22C. A scalpel operator may then choose whether to activate only the tip portion 234, only the face portion 236, or the tip portion 234 in conjunction with the face portion 236 of the scalpel geometry, depending on the surface area desired. Similarly, in a forceps application, the forceps may be divided into inside and outside portions. If the forceps operator desires to remove something that may be surrounded by the forceps, such as a polyp, the internal portions may be activated while the external portions remain deactivated. If opposing sides of a void need to be sealed, the outside surfaces of the forceps may be activated.

By using multiple conductors with a ferromagnetic coating 65 attached to different portions of a primary geometry and separately controlled power sources, different portions of the primary geometry may be activated at the same time for different uses or effects. For example, an edge portion of a primary geometry may be activated for cutting while the blade portion may be activated for hemostasis.

A method of treating tissue may thus include the steps of: selecting a primary geometry having a conductor disposed thereon, the conductor having a ferromagnetic coating disposed on a portion thereof; disposing the ferromagnetic coating into contact with the tissue; and delivering an oscillating electrical signal to the conductor so as to heat the ferromagnetic coating and treat the tissue.

Optional steps of the method may include choosing a primary geometry selected from the group of scalpel, spatula, ball and pointed geometry. Treating of the tissue may include incising, causing hemostasis, ablating or vascular endothelial welding.

A method for tissue destruction may include the steps of selecting a conductor having a ferromagnetic coating disposed on a portion thereof; and delivering an oscillating electrical signal to the conductor so as to heat the ferromagnetic coating and destroy tissue.

Optional steps of the method may include monitoring the tissue and ceasing delivery of the oscillating electrical signal to the conductor when the desired tissue destruction has occurred or undesired tissue effects are to be prevented.

A method for forming a surgical instrument may include the steps of: selecting a primary geometry; coating a conductor with ferromagnetic material; and disposing the conductor on the primary geometry.

Optional steps of the method may include providing electrical connections on the conductor configured for receiving oscillating electrical energy.

Figure 23A:
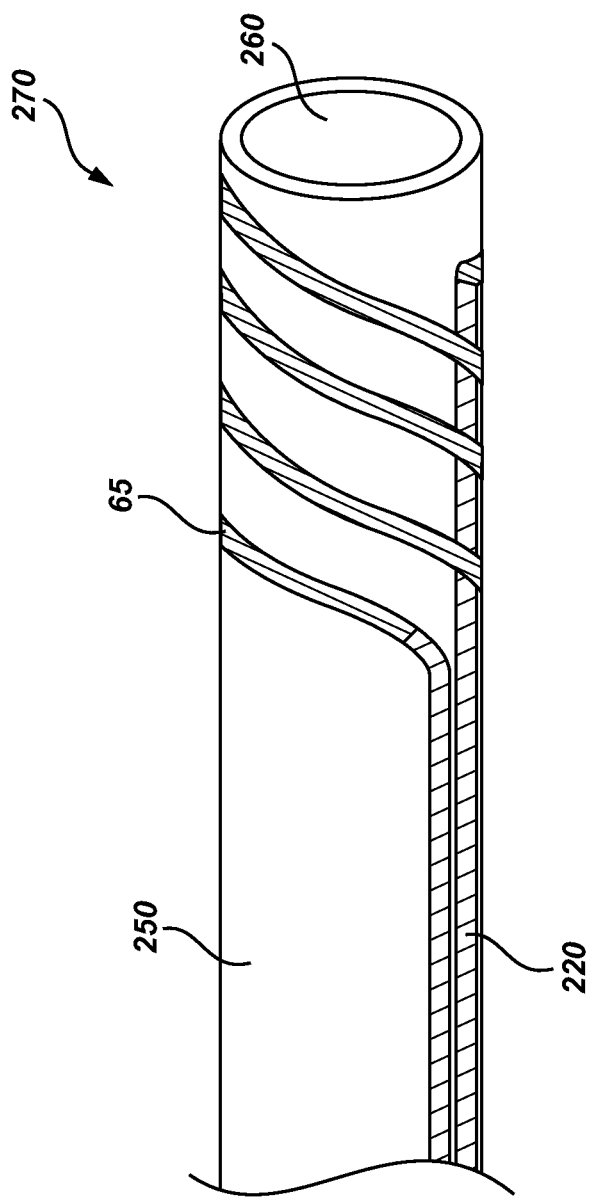
FIG. 23A shows a perspective view of a catheter having a coil of ferromagnetic coated conductor disposed around the tip of the catheter.

Turning now to FIG. 23A, a catheter 270 having a conductor 220 which is at least partially coated with ferromagnetic material 65 disposed around the tip of the catheter is shown. Alternatively, depending upon the therapeutic effect desired, the location of the coil of ferromagnetic coating 65 could be inside the catheter tip, or a single loop of ferromagnetic coated conductor having a circumference which approximates that of the catheter central channel 260 could be located at the end of the catheter tip.

Figure 23B:
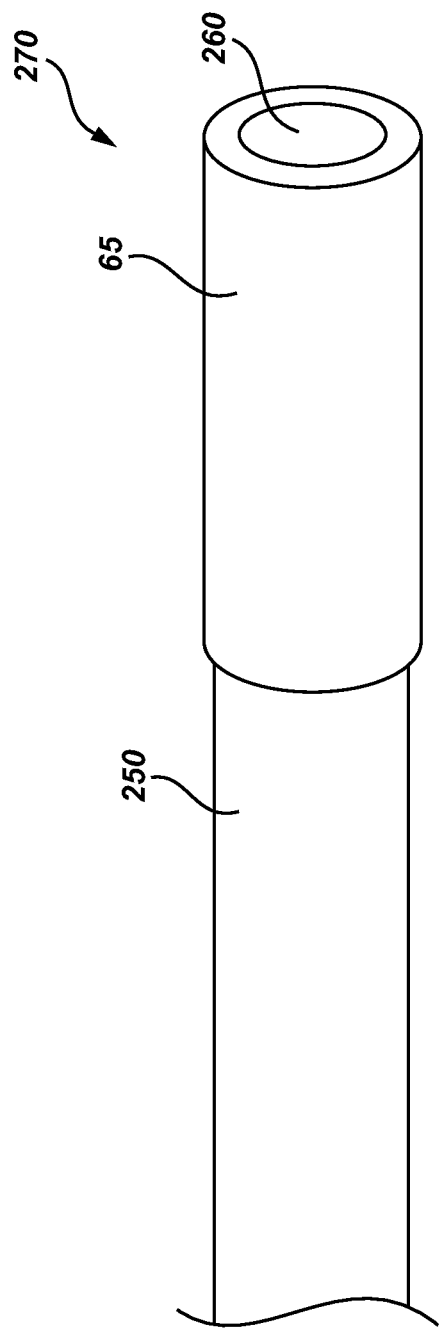
FIG. 23B shows a perspective view of an ferromagnetic coated conductor surgical tool catheter tip.

In FIG. 23B, another ferromagnetic coated catheter 270 is shown. While in some embodiments the conductor may be a wire, coil, or annular structure, a ferromagnetic coated catheter 270 could also be formed wherein the catheter 270 itself would serve as an alternate conductor 250 with a ferromagnetic coating 65. In this embodiment, the catheter 270 could consist of two coaxial conductors, separated by an insulator. At the distal tip of the catheter 270, a conductive coating can be applied such that a continuous electrical path is created by the coaxial conductors. The ferromagnetic coating can be dispersed about the external diameter surface near the distal tip of the catheter, as shown in FIG. 23B, or, upon the end of the catheter at the annular surface connecting the coaxial conductors. This would allow the ferromagnetic coated catheter 270 to perform other functions, such as irrigation, aspiration, sensing, or, to allow viewing access via optical fibers, through a central channel 260, as is common in many interventional as well as open and minimally invasive surgical procedures. Furthermore, the central lumen of the catheter could be used to provide access to other sensing modalities, including, but not limited to, impedance and pH.

Figure 24:
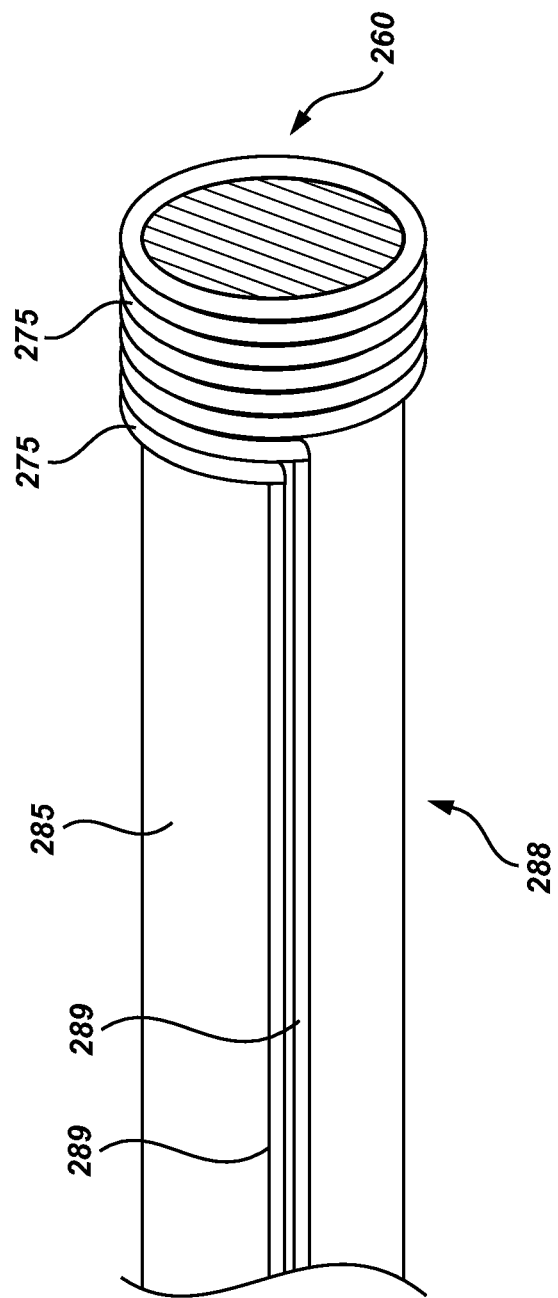
FIG. 24 shows a side view of an alternate embodiment of an ferromagnetic coated conductor surgical tool catheter tip.

Turning now to FIG. 24, a side view of an alternate embodiment of a ferromagnetic coated conductor surgical tool catheter tip 288 is shown. In one embodiment, the conductor may consist of a ferromagnetic coated conductor positioned on a substrate 285 forming a body with a central channel. The ferromagnetic coating may consist of a plated ferromagnetic coating 275 on top of a conductor 289. The plating may be placed on the outside of the substrate 285 such that the thermal effects are directed externally. This may allow the catheter tip to apply thermal tissue effects to tissue walls.

In another embodiment, the inside of the substrate may contain the conductor 289 and ferromagnetic coating 275 such that the thermal effects are directed internally. An internal coating may allow delivery of a meltable solid to a desired area, such as in fallopian tube sealing and osteosynthesis applications.

Alternatively, the ferromagnetic coating 275 may surround the entrance to the central channel 260, such that the thermal effects may be directed in front of the tip. Having the thermal energy be directed in front of the central channel 260 entrance may aid in taking a tissue sample or removal of material, such as a polyp.

The plating may be accomplished through multiple methods. The substrate 285 may be extruded, molded or formed from various materials including high temperature thermoplastic, glass, or other suitable substrate material. The actual plating may be accomplished through electroplating, electroless plating, vapor deposition, or etching, or some combination thereof. Thus through the plating process, a catheter tip 288 may be formed with a ferromagnetic coating 275 on a conductor 280 with a continuous path.

The catheter may also have multiple channels. One channel may be a deployment channel for the ferromagnetic coated conductor. Another channel may be used for one or more sensors or sources, or each sensor or source may have its own channel—such as a temperature sensor, illumination source and endoscope. Other channels may include delivery, irrigation or aspiration of substances, including those associated with treatment, such as in osteosynthesis or fallopian tube sealing. In fact, the ferromagnetic coating may aid in the melting of such substances.

Figure 25:
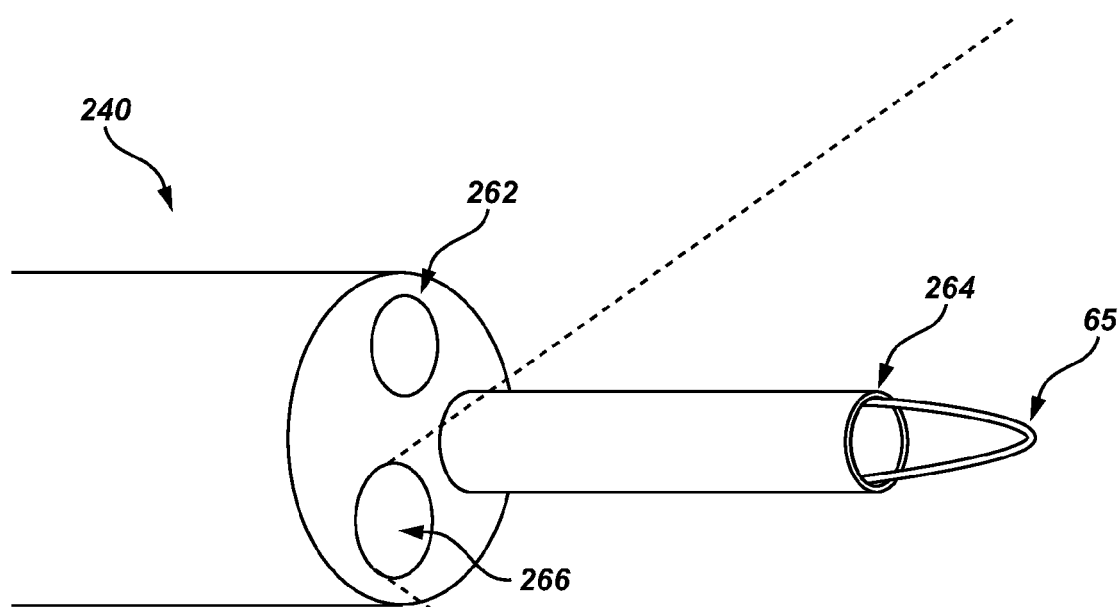
FIG. 25 shows an alternate embodiment of a ferromagnetic coated conductor surgical tool ferromagnetic tip disposed within an endoscope.

Turning now to FIG. 25, an endoscope 240 with a viewing channel 262 of rod lens type or organized fiber bundle type aside a light emitting source 266 is shown. A loop coagulator/cutter 264 is shown which consists of the ferromagnetic coated conductor 65. Such an adaptation is contemplated in snare applications such as colon polypectomy or sealing and cutting applications in various laparoscopic procedures. Other sensing modalities include near field tumor cell detection or infrared heat monitoring. Tool configurations similar to those used with the described endoscope 240 can be embodied in tools that can be delivered to target tissue through the lumen of a catheter.

In one embodiment, tumor cells are caused to be tagged with materials that fluoresce when exposed to ultra-violet light. The endoscope 240 may contain a light source 266, and sensor or optics within the channel 262 that return the detected florescence. The ferromagnetic coating 65 portion of the endoscope 240 may then be directed at the tagged tissue for destruction.

In another embodiment, materials are deposited around target tissue or bone in a solidified condition. Once delivered, the materials may be melted to conform at the site via activation by the endoscope 240 described above. Examples of use of this embodiment include fallopian tube sealing and osteosynthesis. Furthermore, such materials could be removed by melting with the same or similar endoscope 240, and aspirated through a central lumen of the endoscope 240. In yet further applications, materials may be delivered in liquid form, and cured by a thermal heating process induced by the endoscope 240.

Alternatively, the conductor may be part of a bundle of fibers. The fibers may be contained within a catheter or otherwise bundled together. The conductor may have a ferromagnetic coating, while the other fibers may have other purposes that include visual observation, sensing, aspiration, or irrigation.

A method of tissue ablation may include the steps of: selecting a catheter with a ferromagnetic covered conductor; causing the ferromagnetic covered conductor to touch tissue to be ablated; and delivering power to the ferromagnetic covered conductor.

Optional steps may include: directing the catheter to the tissue through the aid of an endoscope; selecting a ferromagnetic coated conductor disposed on the catheter; selecting a ferromagnetic coated conductor contained within the catheter; causing the ferromagnetic coated conductor to be deployed from the catheter; or touching the ferromagnetic coated conductor to the tissue to be ablated.

A method of delivering a substance into a body may include the steps of: selecting a catheter with a ferromagnetic coated conductor; placing a substance in the catheter; inserting the catheter into a body; and causing power to be sent to the ferromagnetic coated conductor to induce a thermal effect in the substance.

Optional steps may include: selecting a substance for osteosynthesis; selecting a substance for fallopian tube sealing; or melting the substance in the catheter.

A method of treating tissue may include the steps of: selecting a catheter with a ferromagnetic coated conductor; placing the catheter in contact with tissue; and selecting a power setting. The temperature range may correspond to a temperature range or desired tissue effect. The desired tissue effect may be selected from the group of vascular endothelial welding, hemostasis, searing, sealing, incision, ablation, or vaporization. In fact, the power setting may correspond to a desired tissue effect.

Figure 26:
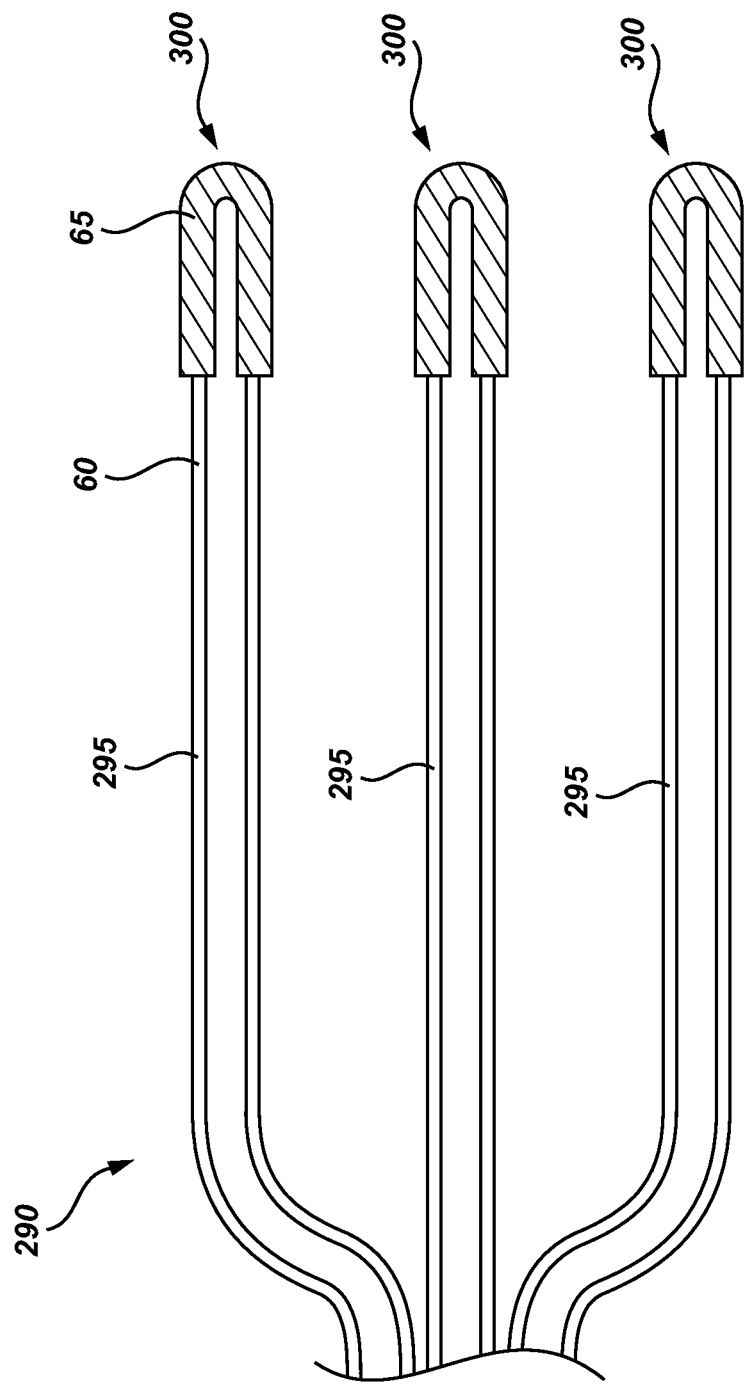
FIG. 26 shows a tissue ablation tool.

Turning now to FIG. 26, a tissue ablation tool 290 is shown. In typical applications of tissue ablation, an arm or tine 295 is inserted into undesired tissue. One or more tips 300 may be activated such that the tissue temperature is raised to a desired level for a desired amount of time. Once the desired amount of time has passed with the tissue temperature held at the desired temperature, or undesired effects are noticed, the one or more tips 300 may be deactivated and removed from the tissue.

In one embodiment, a conductor may be contained within one or more arms or tines 295 with tips 300 that may contain ferromagnetic coatings 65. The tips 300 may be inserted into tissue and temperature controlled until tissue destruction occurs or one or more undesired tissue effects occur. The tissue effects may be monitored through sensors in the tines 295 or externally.

One or more sensors may be placed in multiple ways. In one embodiment, a sensor is placed in the tine and away from a ferromagnetic coated tip 300. In another embodiment, one tip 300 may have a ferromagnetic coating, while an alternate tip 300 may have no coating, but a sensor disposed thereon or contained therein. The sensors may monitor tissue effects or return signals to be observed or processed. This may include sensors such as temperature sensors, cameras and remote imaging. In another embodiment, the temperature may be monitored through external imaging.

A sensor may thus form part of a feedback loop. By monitoring one or more tissue effects, the ablation tool may self-adjust power settings. This self-adjustment may allow the system to operate below the Curie point and still maintain a desired tissue effect and/or temperature range.

In the case where more than one tip 300 is used, the tips 300 with a ferromagnetic coating 65 may be individually controlled such that the thermal profile is concentrated in the desired area. This may also allow a second tine to monitor tissue effects, while a primary tine is used to perform the thermal function.

While a diagram has been shown of a multi-tip tissue ablation tool in FIG. 26, a single tissue ablation tool may be made in a configuration similar to, for example, FIG. 7C.

Besides the advantages of uses in tissue, the surgical tool may also be self-cleaning. In one embodiment, when activated in air, the tool may achieve a temperature sufficient to carbonize or vaporize tissue debris.

Figure 27:
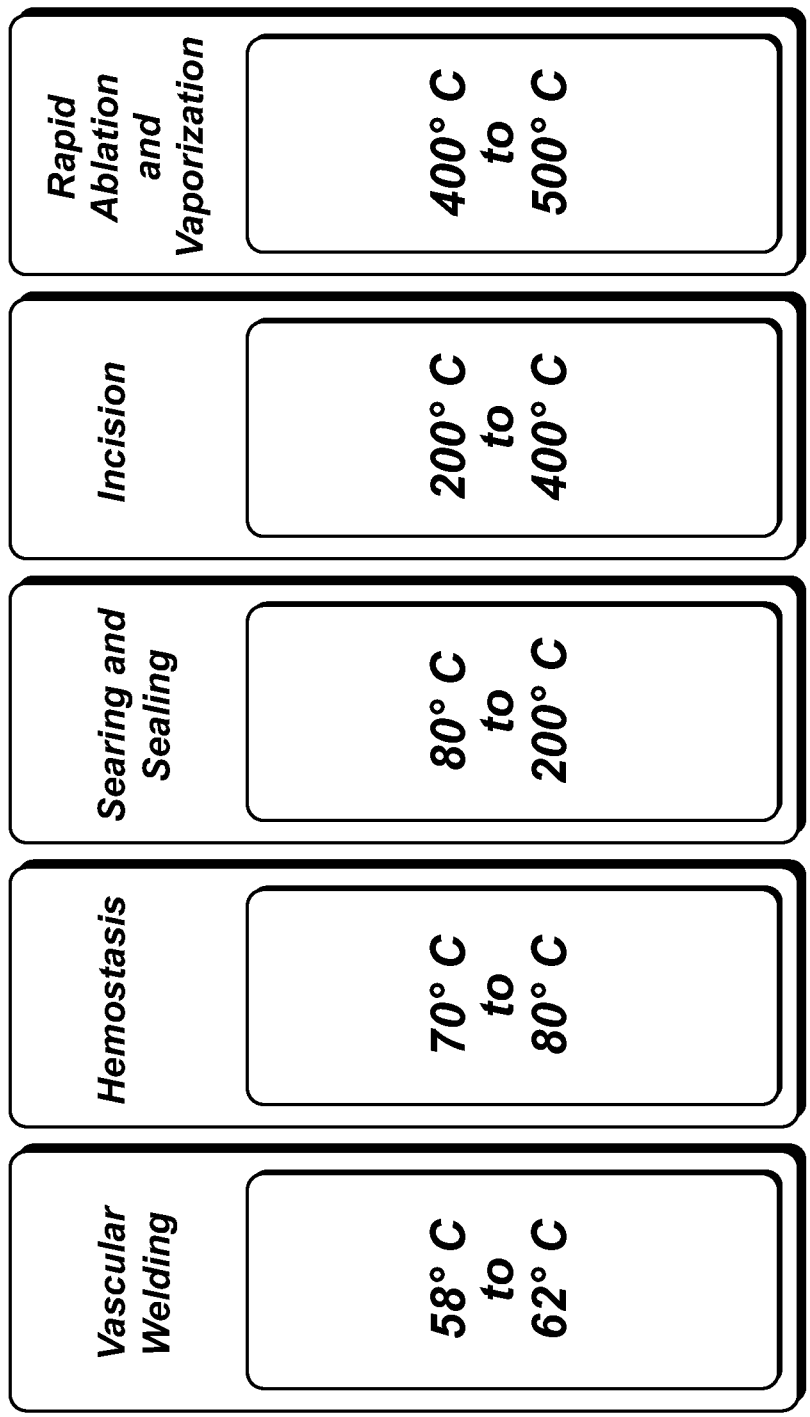
FIG. 27 shows a thermal spectrum as related to tissue effects.

Turning now to FIG. 27, a temperature spectrum is disclosed. Tissue may react differently at different temperatures with a tissue treatment element (such as a ferromagnetic coated conductor) and thus temperature ranges will result in different treatments for tissue. Specific tissue treatments are somewhat variable due to inconsistencies including tissue type and patient differences. The following temperatures have been found to be useful. Vascular endothelial welding may be optimal at 58-62 degrees Centigrade. Tissue hemostasis without sticking may be achieved at 70-80 degrees Centigrade. At higher temperatures, tissue searing and sealing may occur more quickly, but coagulum may build-up on the instrument. Tissue incision may be achieved at 200 degrees Centigrade with some drag due to tissue adhesion at the edges. Tissue ablation and vaporization may occur rapidly in the 400-500 degree Centigrade range. Thus, by controlling the temperature of the device the "treatment" of tissue or other materials can be controlled, depending on whether vascular endothelial welding, tissue incision, hemostasis, tissue ablation, etc. is desired.

According to the spectrum disclosed above, power delivery settings corresponding to the desired temperature range may be included in the power delivery switch. In one embodiment, the foot pedal may have several stops that indicate to the surgeon the likely tip temperature range of the current setting.

Figure 28:
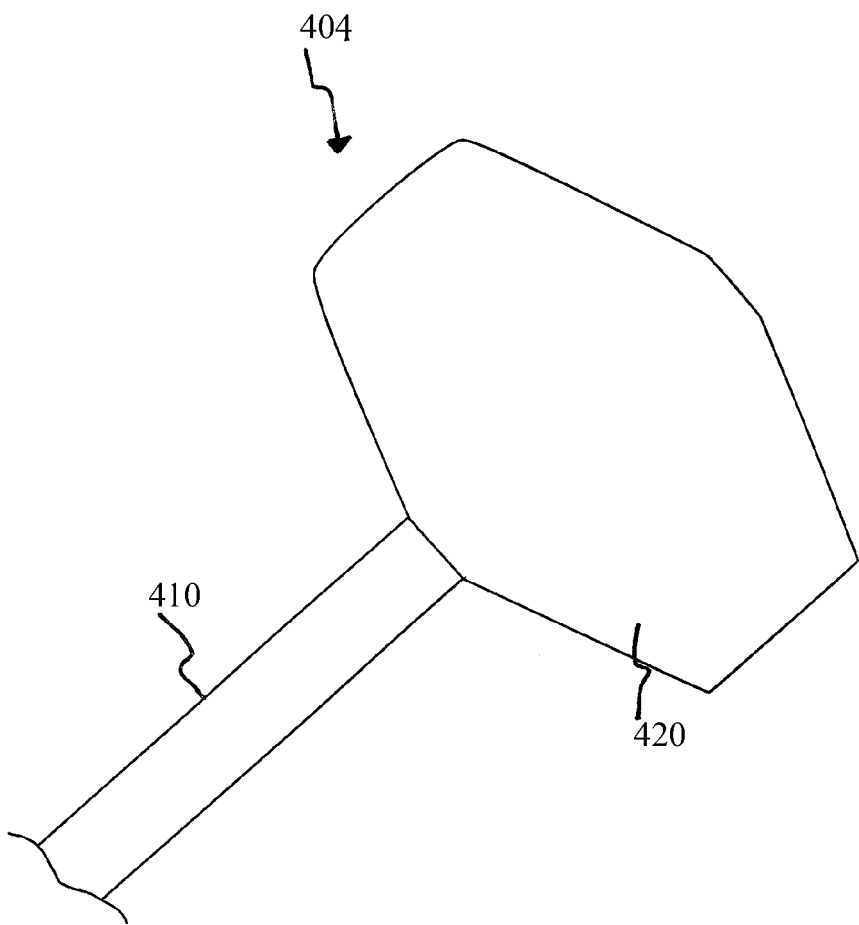
FIG. 28 shows a perspective view of an end filled balloon catheter.
Figure 29:
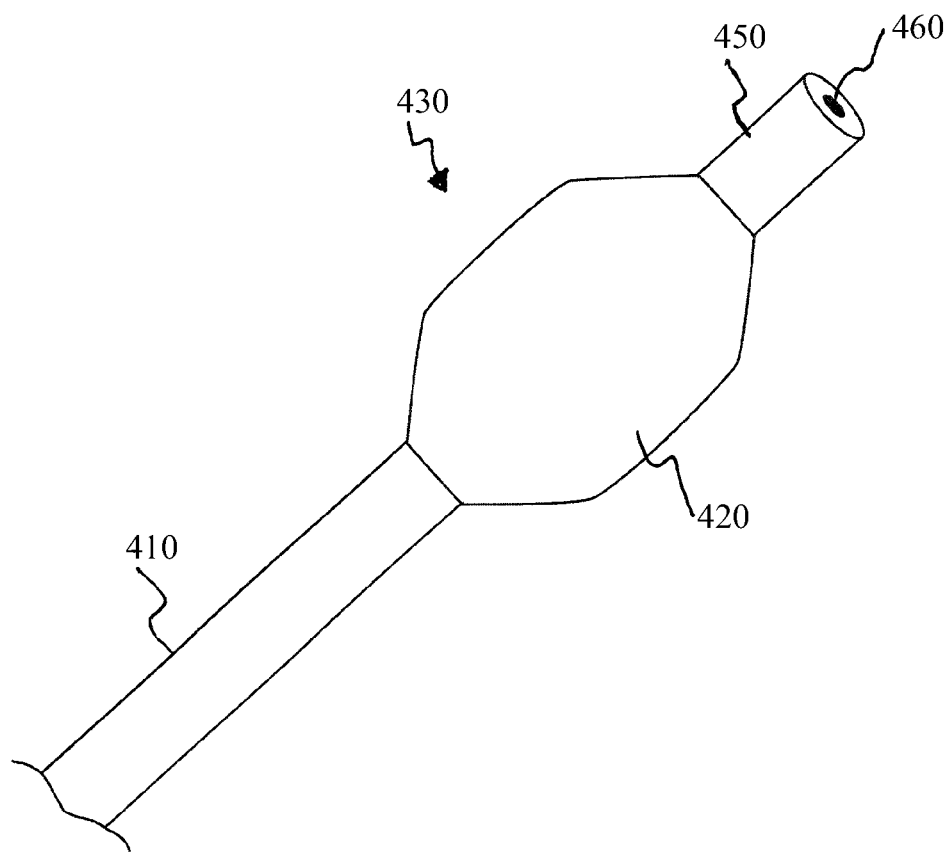
FIG. 29 shows a perspective view of a center filled balloon catheter.

Turning now to FIGS. 28 and 29, there are shown balloon catheters 404 and 430 which may be part of a thermal system or a surgical tool in accordance with aspects of the present invention. A balloon catheter 404 may include a catheter body 410 which is generally elongate and may include one or more lumens for passing fluids or other material therethrough. The catheter 404 may also include an expandable balloon 420.

The balloon 420 may be expanded by insertion of matter, such as gas or liquid, into the balloon chamber so that the balloon is able to perform some function. Similarly, the balloon 420 may be contracted by the removal of matter from the balloon chamber to cause the balloon 420 to collapse and facilitate insertion into or retraction from a confined area.

The fluid which is used to expand the balloon 420 may be heated so that a heating effect may be applied to tissue or some other structure within a body via the balloon. While hot fluid may be injected into the catheter body 410 and thus the balloon 420, in accordance with the principles of the present invention, a heating element may be contained in the catheter body 410 and/or within the balloon 420 to heat fluid or other material in the balloon 420 and impart heat to a surface touching or disposed sufficiently adjacent the balloon body 420. While a gas may be used as the fluid, liquids generally have better heat conduction and are likely to be used more frequently.

A fluid with a high specific heat may be desirable, as the temperature of the fluid may remain more constant as the heat is delivered to the surface of the balloon 420. In one embodiment, D5W (dextrose 5% in water) may be used because of its high specific heat (0.965), its common use availability in Intravenous Therapy and its hypotonic properties in case of breakage. In another embodiment, normal saline solution which is commonly used in intravenous therapies may be used because of its high specific heat (0.997) and hypotonic properties in case of breakage.

In one embodiment the balloon 420 may include stretchable material that may conform to external surfaces. Thus, the balloon may conform to an interior structure in a body while heat is being applied. In another embodiment, the material may not be stretchable, but may include another desirable trait such as puncture resistance or heat transfer.

A heating element (not shown in FIGS. 28 and 29) may include a ferromagnetic element, such as a ferromagnetic covered conductor coil, to heat the fluid. A ferromagnetic covered conductor may be advantageous because it may use a simple power source without any electrical conductive path through the solution or stray RF pathways. A ferromagnetic covered conductor may also be advantageous because it can generate significant heat very quickly.

In other embodiments, the ferromagnetic element may be one or more ferromagnetic covered elements running adjacent to the channel 460 or may be disposed parallel to and inside the channel 460. In another embodiment, a ferromagnetic covered conductor is placed in the center of the channel 460, and the fluid flows around it.

Referring to FIG. 28, a top view of an end filled balloon catheter 404 is shown. The end filled balloon catheter 404 may include the catheter body 410 ending with an expandable balloon 420 extending from or surrounding the catheter tip. The tip may be expanded to fit within a cavity, which is further described in conjunction with FIGS. 31 and 32 below. An end filled balloon catheter 404 has the advantage of expanding away from the tip and the sides of the catheter. This allows precise placement of the balloon 420 against tissue desired to be treated with minimal interference from the catheter body 410.

Referring to FIG. 29, a perspective view of a center filled balloon catheter 430 is shown. A center filled balloon catheter 430 may include a catheter body 410 which is surrounded by an expandable balloon 420. Extending beyond the balloon 420 may be a catheter tip 450. A lumen 460 may extend through the catheter body 410 and be used for passing a guidewire for placement, or to allow the injection and/or aspiration of material to or from the body in which the catheter 430 is placed. The catheter body 410 may be guided by a sensor or camera disposed in the lumen 460 or extending through the catheter tip.

The catheters 404, 430 may have several lumens or channels within. This may include a lumen 460 for a guidewire, fluid flow, sensing and/or other operations near the desired site. A second lumen may be used to direct fluid into the balloon 420 to thereby expand and/or contract the balloon 420.

Figure 30:
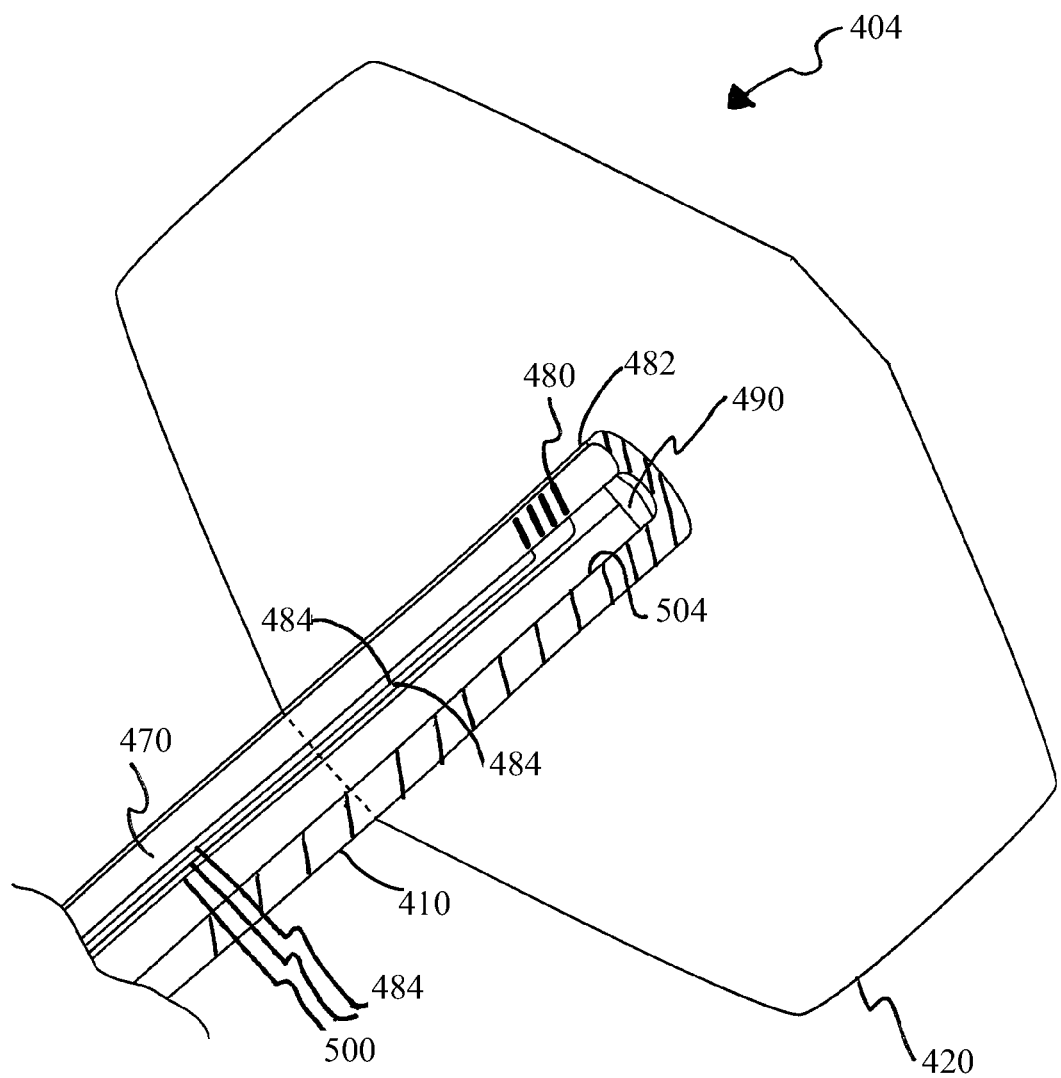
FIG. 30 shows a cut-away view of the end filled balloon catheter of FIG. 28.

Turning now to FIG. 30, a cut-away or cross-sectional view of the end filled balloon catheter 404 of FIG. 28 is shown. A heated fluid may be used to expand the balloon portion 420 of the catheter 404. In accordance with one aspect of the invention, the catheter body 410 may have walls which define a fluid channel or lumen 470 having a ferromagnetic coil 480 disposed therein and a port 482 for releasing the fluid into the balloon 420. It will be appreciated that the ferromagnetic coil 482 may be made in a variety of ways, including coating a thin layer of ferromagnetic material over a conductor coil.

In the embodiment shown in FIG. 30, a conductor 484 may extend along the catheter body 410 such that only a portion of the conductor 484 forming the conductor coil 480 extends into the fluid lumen 470. It will be appreciated, however, that the entire length of the conductor 484 disposed in the catheter 404 could be disposed in the fluid lumen 470 and could be used to heat fluid passing through the lumen. Additionally, all or part of the conductor 484 could be coated with a ferromagnetic coating.

The conductor coil 480 (e.g. portions which are covered with ferromagnetic material) may be activated to heat fluid passing over the coil 480 by heating the ferromagnetic layer disposed on the conductor 484. The fluid flow rate, heat transfer coefficient and amount of power delivered to the coil 484 may be adjusted to achieve a desired temperature within the fluid as it passes into the balloon 420. While not shown in FIG. 30, it will be appreciated that all or a portion of the conductor coil 480 could extend into the balloon 420 to provide initial heating of the fluid or to provide continual heating of the fluid in the balloon 420.

One or more sensors 490 may monitor the fluid in the balloon 420 and/or the fluid within the fluid lumen 470. In one embodiment, a sensor unit 490 may have a fluid side sensor and a balloon side sensor. The systems may be powered and/or communicate through wires 500 within the catheter.

By monitoring the temperature, the sensor(s) 490, the conductor 484 and conductor coil 480 may form a balloon heating system which acts as a closed loop-system through feedback. The temperature of fluid within the channel 470 may correlate with the amount of heat transferred to the fluid. The temperature of fluid within the balloon 420 may help in the understanding of heat loss from the balloon 420, and/or the effect of incoming heated fluid. The temperature of the heated fluid may also ensure maintenance of a desired temperature.

In some cases, other sensors may be desired. For instance, the balloon 420 may be transparent to enable a visual sensor or optic feedback for guidance and/or monitoring of tissue being treated or destroyed by the balloon 420. A light may be included to aid in the vision sensing. While shown in FIG. 30 as being closed, the lumen 504 defined by interior walls of the catheter body 410 and containing the sensor(s) 490, may be open to allow better viewing and/or advancement of the sensor(s) or other materials into or out of the balloon 420.

Figure 31:
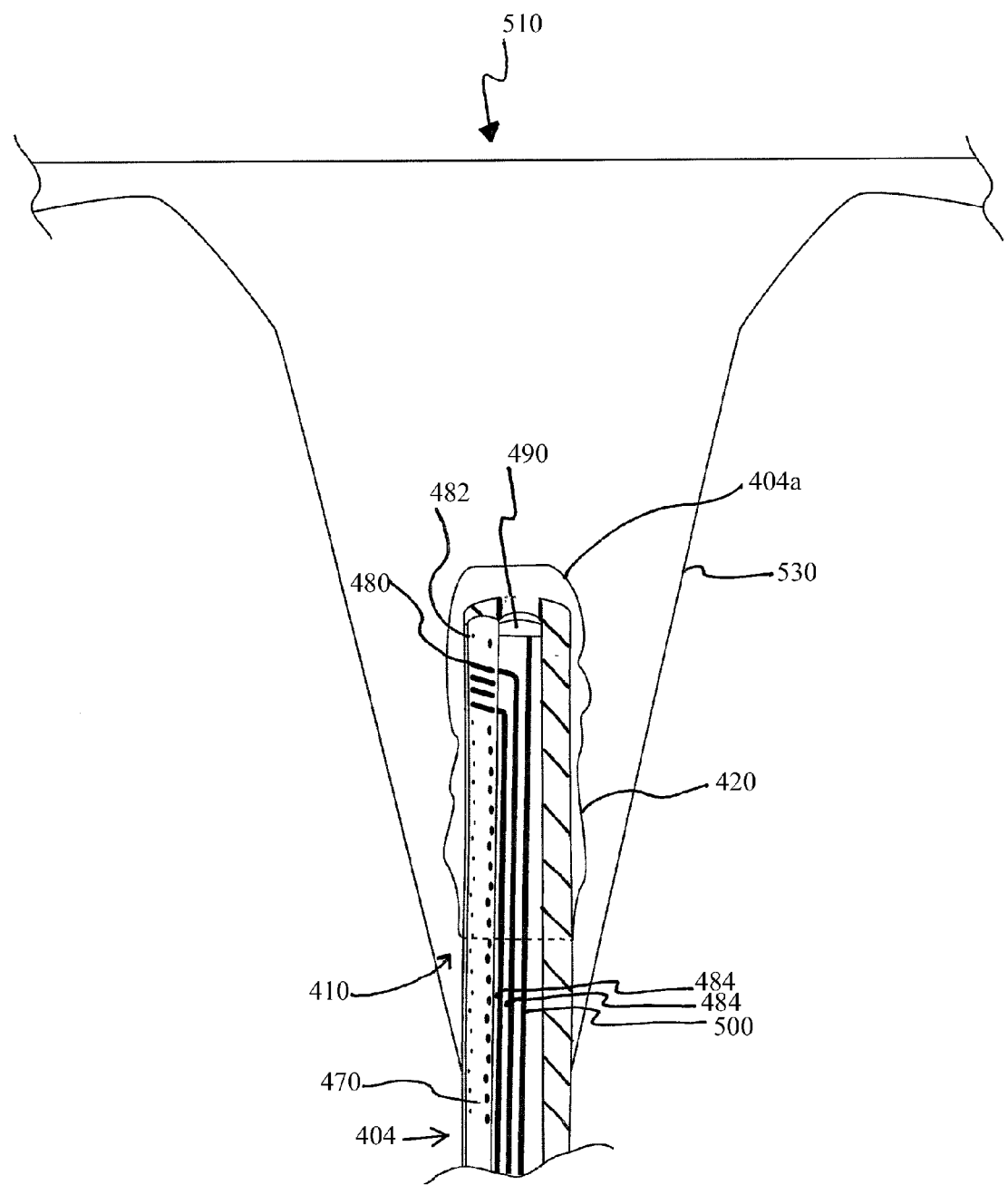
FIG. 31 shows a cut-away view of a deflated end filled balloon catheter during an endometrial ablation procedure.
Figure 32:
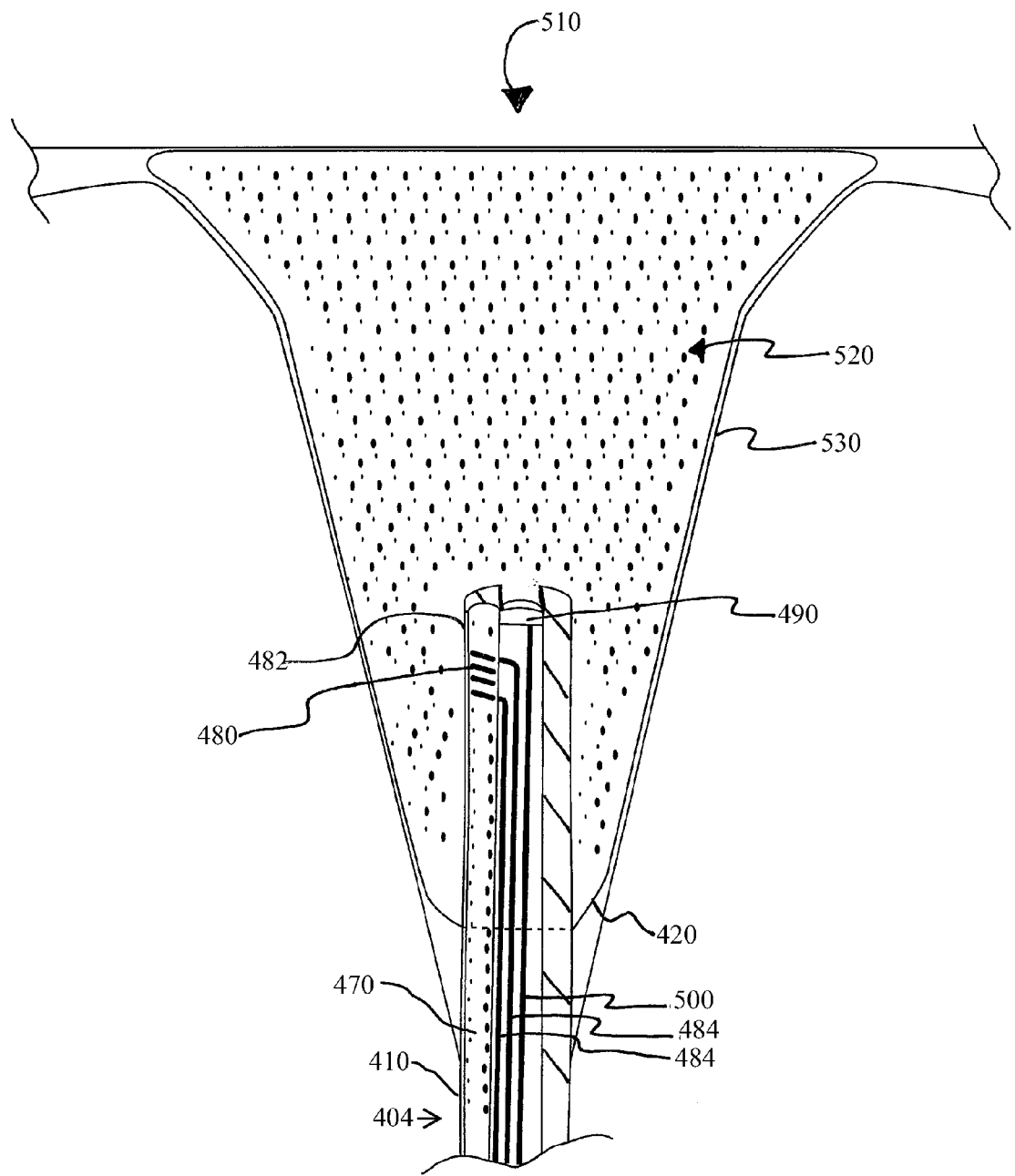
FIG. 32 shows a cut-away view of an inflated end filled balloon catheter during an endometrial ablation procedure.

Turning now to FIGS. 31 and 32, a catheter 404 is shown in cross-section performing two phases of an endometrial ablation procedure. A preparation phase is shown in FIG. 31, where a deflated end filled balloon catheter 404 is inserted into a uterus 510 and any baseline measurements are taken. A treatment phase is shown in FIG. 32, where the endometrial lining 530 of a uterus 510 is ablated with applied heat through the transfer of heat from the fluid 520 through the expanded balloon 420 to the endometrial lining 530. After treatment, the balloon 420 may be collapsed and the catheter 404 removed from the uterus.

Turning specifically to FIG. 31, a cross-sectional view of a deflated end filled balloon catheter 404 is shown during insertion for an endometrial ablation procedure. The catheter 404 includes a collapsed balloon 420, while the fluid channel 470 defined by the catheter body 410 may be primed with a fluid, typically a liquid such as saline solution, etc. The distal end 404a of the catheter 404 may then be inserted through the cervix into the uterus 510.

In one embodiment, the balloon 420 may be clear or otherwise transparent and the sensor unit 490 may include a visual sensor to view the surrounding tissue before the heating procedure begins. In another aspect of the invention, temperature readings and other measurements, such as a visual color check, may be performed before the procedure. After the insertion and any pre-measurements are taken, the balloon 420 may be filled with a heat transfer fluid for the treatment phase.

Turning now to FIG. 32, a cross-sectional view of the catheter body 410 of an inflated end filled balloon catheter 404 during an endometrial ablation procedure is shown. Fluid 520 has been injected into the balloon 420 through a fluid lumen 470. As the fluid passes through the fluid lumen 470 and out the port 482, the fluid may be heated by activating the ferromagnetic coil 480. This is typically done by providing energy to the conductor 484, around which the ferromagnetic coating is applied to form the coil 480.

The heating may be regulated by a sensor unit 490 that may detect the temperature of the fluid in the channel 470 and/or the temperature of the fluid 520 in the balloon 420. As more fluid 520 enters the balloon 420, the balloon 420 may expand and conform to the endometrial layer 530 of the uterus.

Once sufficient fluid 520 has been infused into the balloon 420 such that the balloon surface covers a sufficient part of the endometrial layer 530, the fluid flow may be stopped and the energy to the heating element may be stopped. The heating element may be activated after some fluid 520 is in the balloon to prevent damage to the balloon and the heating element may be left on to drive the fluid to or maintain the fluid at a desired temperature for sufficient time to destroy the endometrial tissue layer 530 in the uterus.

As a ferromagnetic covered conductor of the present invention has quick heating and cooling properties, more precise heating of the fluid may be provided as the heat provided by the heating element may be stopped quickly after the desired temperature is reached. Thus, the physician may be provided with more precise control of the temperature of the fluid 520 in the balloon 420.

Once expanded, the end filled balloon catheter 404 may remain expanded until the treatment is complete. In another embodiment, the treatment is performed until a specific color change is noted in the tissues through the balloon 420. In another embodiment, multiple factors are monitored, which may include time, temperature and/or tissue color, so that a treatment may more specifically correspond to an individual and/or potential problems may be noticed before they become damaged. This monitoring may be performed by a sensor unit 490 on the catheter 404.

While not shown in FIG. 31 or 32, all or part of the ferromagnetic coil 480 could be disposed on the outside of the catheter body to facilitate continued heating if needed. A mechanism for circulating the fluid could also be provided.

Figure 33:
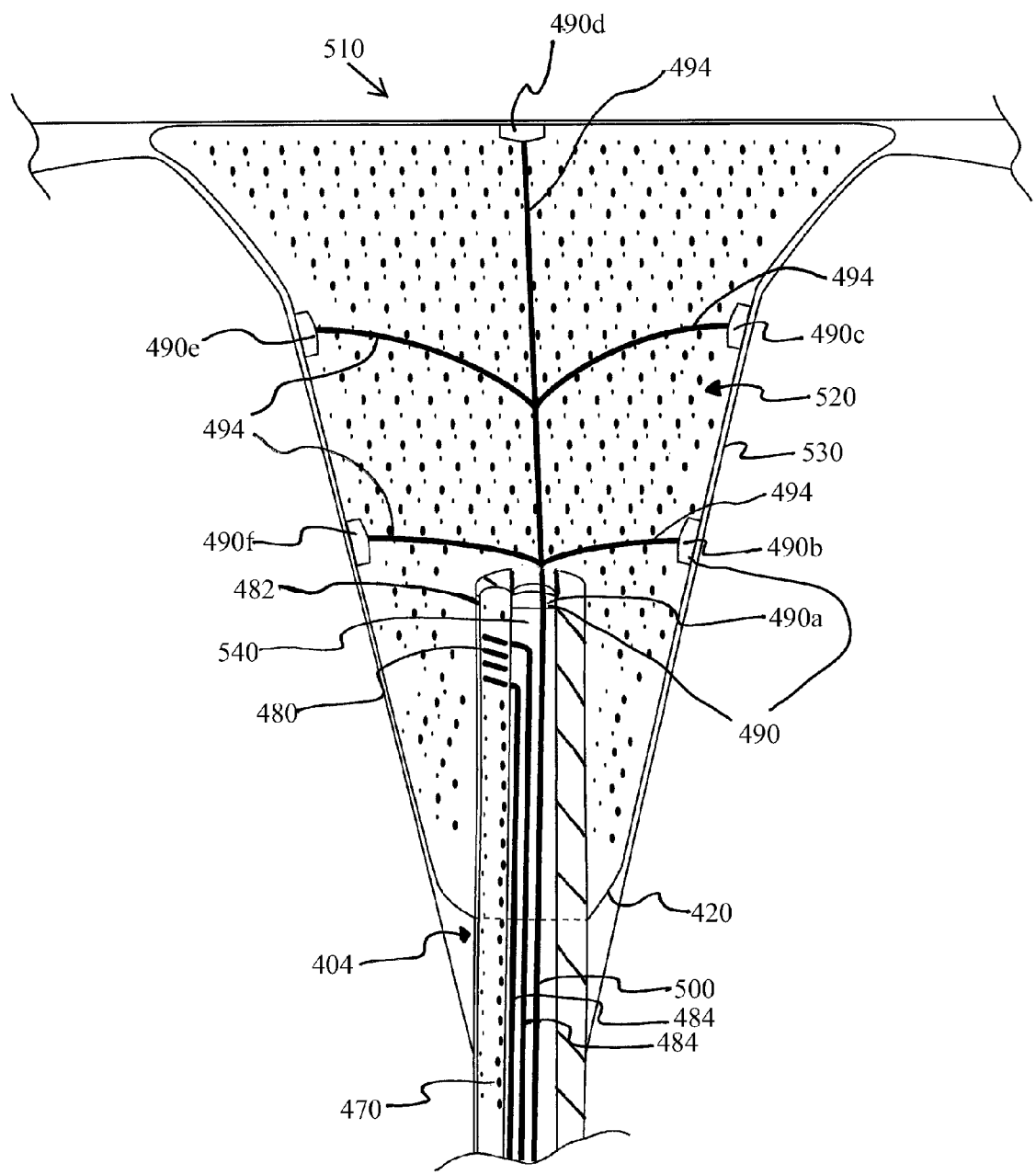
FIG. 33 shows a cut-away view of an inflated end filled balloon catheter with sensor network during an endometrial ablation procedure.

Turning now to FIG. 33, a cut-away view of an inflated end filled balloon catheter 404 with a sensor unit 490 during an endometrial ablation procedure is shown. The sensor unit 490 may be formed by a network of sensors 490a, 490b, 490c, 490d, 490e, 490f which also may be deployed with the balloon 420. The sensor network 490a, 490b, 490c, 490d, 490e, 490f may reside in a catheter channel or lumen 540 and be deployed out of the lumen 540 as the fluid 520 fills the balloon 420. Sensor units 490a, 490b, 490c, 490d, 490e, 490f may be attached to the balloon surface and monitor the uterus 510, including the endometrial layer 530. This monitoring may include temperature, tissue color, electrical properties (including without limitation resistance) and/or other desired properties.

In one embodiment, the sensor units 490a, 490b, 490c, 490d, 490e, 490f may be attached to the balloon 420 surface. The wires 494 for sensors 490a, 490b, 490c, 490d, 490e, 490f, and a portion of the balloon 420 may be contained within a cavity or channel within the catheter. When fluid expands the balloon 420, the sensor units 490a, 490b, 490c, 490d, 490e, 490f and a portion of the balloon 420 may be pulled from the cavity and may generally follow the contour of the uterus 510.

In another embodiment, the sensors 490a, 490b, 490c, 490d, 490e, 490f may form part of the surface of the balloon 420. In its deflated state, the wires 494 and sensors 490a, 490*b*, 490*c*, 490*d*, 490*e*, 490*f* may rest near the catheter tip. In some cases, the wires 494 may actually reside in the lumen 540. When expanding, the wires 494 and sensors 490*a*, 490*b*, 490*c*, 490*d*, 490*e*, 490*f* may deploy with the balloon 420, e.g. be pulled into place by expansion of the balloon 420, or may be advanced independently.

By deploying sensors 490*a*, 490*b*, 490*c*, 490*d*, 490*e*, 490*f* onto the surface, the tissue may be more closely monitored and the sensor unit 490 may provide more accurate information about the monitored tissue. Similarly, the heated fluid 520 may be monitored by the sensor unit 490.

Figure 34:
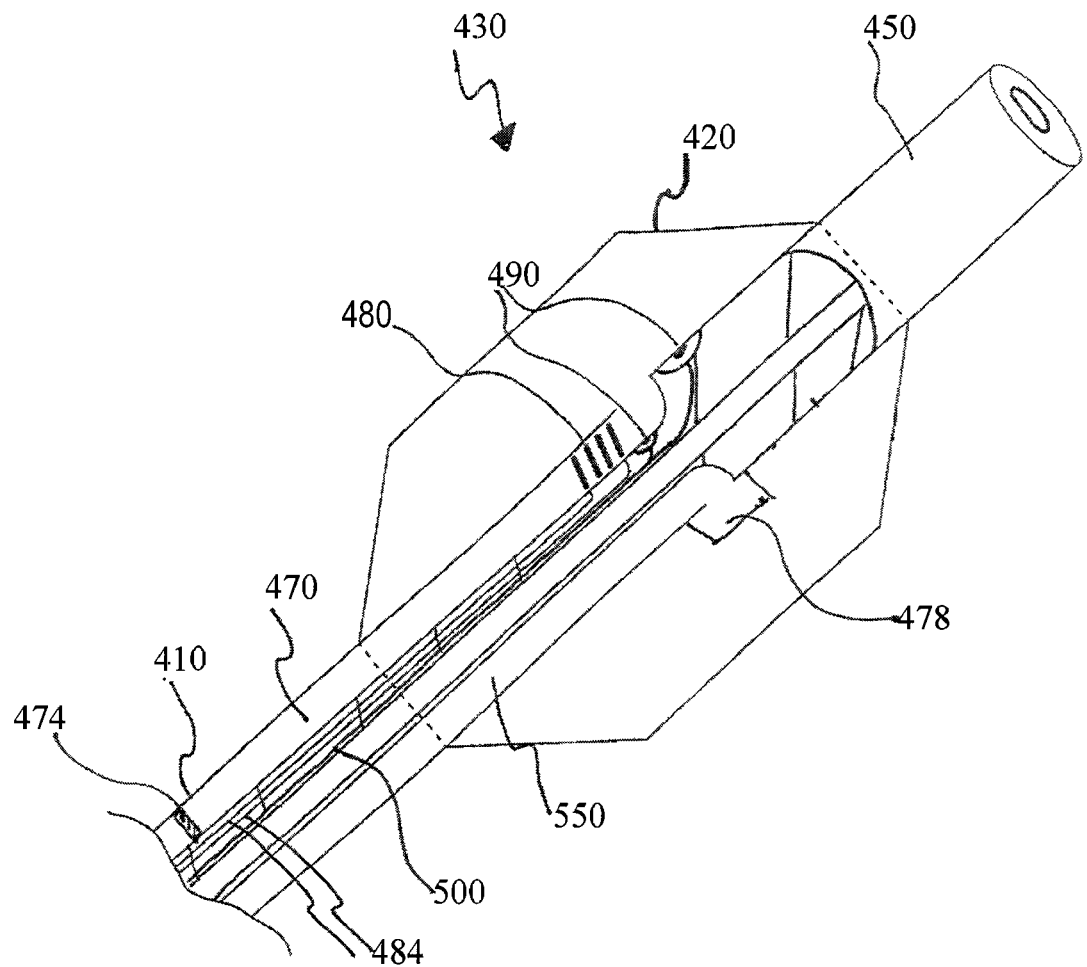
FIG. 34 shows a cut-away view of the center filled balloon catheter of FIG. 29.

Turning now to FIG. 34, a cut-away view of the catheter body 410 of the center filled balloon catheter 430 of FIG. 29 is shown. Similar to FIG. 30, a heated fluid may be used to expand a balloon 420 portion of the center filled balloon catheter 430. A fluid channel or lumen 470 may contain a ferromagnetic coil 480 which may be activated to heat liquid within the coil 480. The fluid flow rate and amount of power delivered to the coil 480 may be adjusted to achieve a desired temperature. One or more sensors 490 may monitor the fluid in the fluid lumen 470 and/or in the balloon 420.

In one embodiment, the sensor unit 490 may have a fluid side sensor and a balloon side sensor. The sensors 490 may be powered and/or communicate through one or more conductors or wires 500 within the catheter.

The body 410 of the catheter 430 may also define a plurality of lumens. In addition to the fluid lumen 470, the catheter body 410 may contain a recirculation lumen 550 that allows for fluid circulation. In one embodiment, the recirculation lumen 550 may allow liquid within the balloon to re-enter the catheter and pass by the ferromagnetic covered conductor coil 480. This may further allow for maintenance of temperature and constant heating. (A recirculation lumen may also be used in the embodiment of FIGS. 28 and 31-33 if desired). The fluid lumen 470 and recirculation lumen 550 may be disposed in communication with an external pump (not shown) and the pump may include a control for regulating the rate of flow to thereby control temperature within the balloon.

In the alternative, movement of the fluid may be caused by a pump 478 located within the balloon 420 of the catheter or externally attached to the recirculation channel. A valve or regulator 474 on the catheter or external thereto may be used to limit flow out of the balloon 420 sufficiently that the balloon 420 achieves its desired size or pressure, or to prevent undesired movement when a recirculation pump is not activated.

Figure 35:
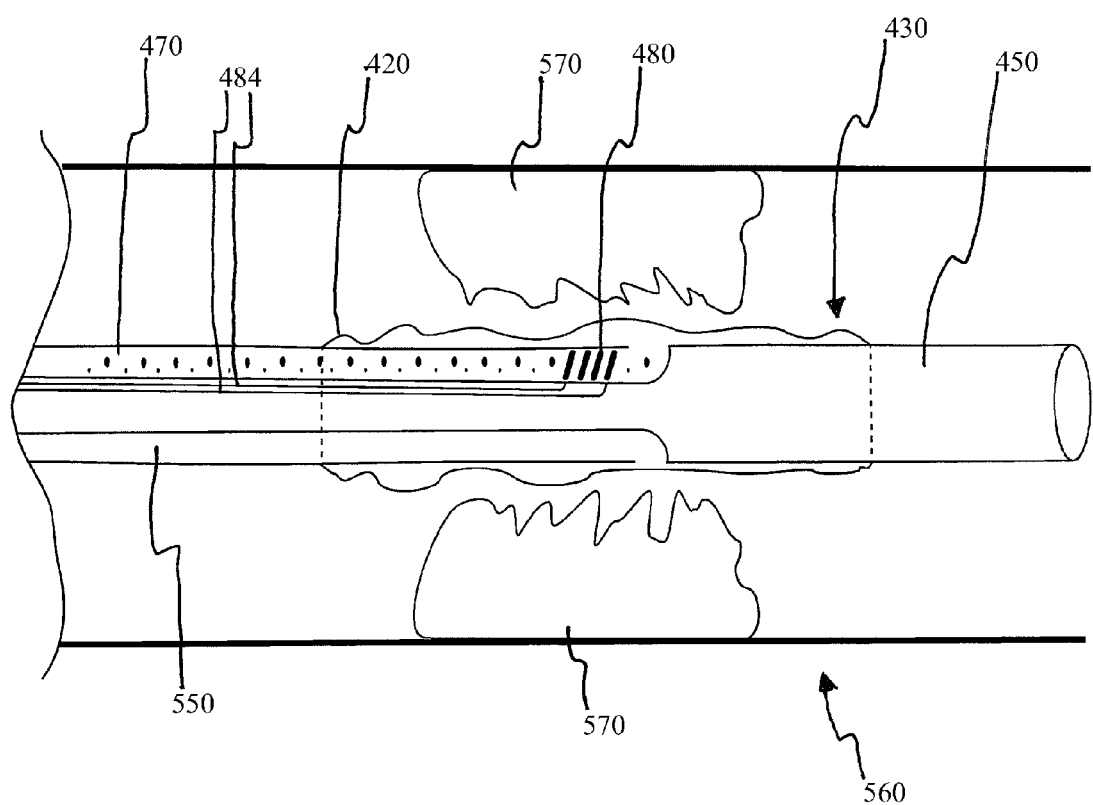
FIG. 35 shows a cut-away view of a deflated center filled balloon in a biological channel.
Figure 36:
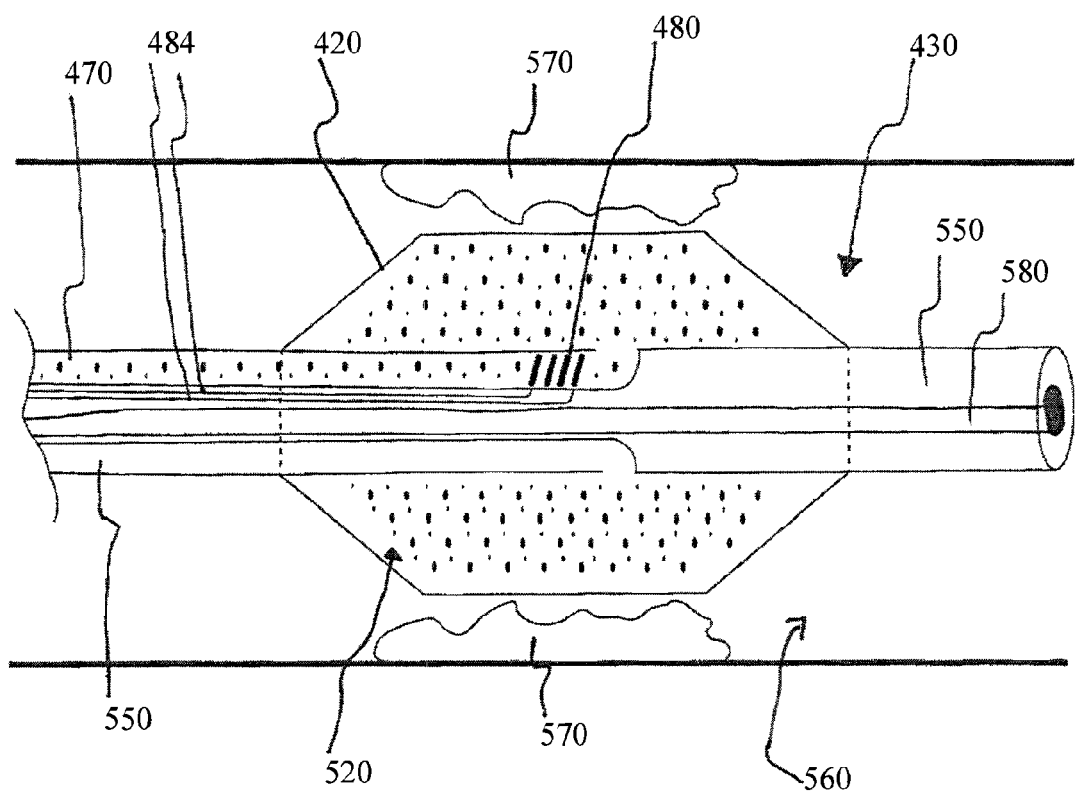
FIG. 36 shows a cut-away view of an inflated center filled balloon in a biological channel.

Turning now to FIGS. 35 and 36, a center filled balloon catheter 430 is shown in a biological channel 560 during insertion (FIG. 35) and after expansion (FIG. 36). A deflated center filled balloon catheter 430 may be inserted into the biological channel 560 and in-between biological material 570, such as tissue, plaque, residue, etc. Once in place, and any desired initial measurements are taken, the balloon 420 may be expanded with fluid 520. As the fluid 520 exits the fluid lumen 470, it may be heated by a ferromagnetic covered conductor coil 480 or other ferromagnetic structure. As the balloon 420 surface contacts the biological material 570, the fluid 520 may transfer heat to the biological material 570 through the surface of the balloon 420. Thus, the biological material 570, etc. may be melted, ablated or otherwise removed or destroyed by the applied heat. The heat may be monitored and/or controlled by feedback from one or more sensors 490 (See e.g., FIG. 34) within or on the catheter 430 or the balloon 420.

After the expansion portion of the procedure is complete, the balloon 420 may be deflated by removal of the fluid 520. The catheter 430 may then be removed from the biological channel 560. One of skill in the art will appreciate that the center filled balloon catheter 430 could be used, for example, to enlarge the opening through a partially clogged artery.

Referring specifically to FIG. 35, a cut-away view of a deflated center filled balloon catheter 430 in a biological channel 560 is shown. The catheter may be inserted in between biological material 570 such that the balloon 420 portion is centered near or within the material 570. The insertion may be aided by sensors (not shown), including internal or external sensors, guidewires, etc. In one embodiment, the catheter 430 may include a visual system, which may include optics or a visual sensor, to display feedback during insertion. In another embodiment, the catheter 430 may be inserted while using an external imaging device.

Referring specifically to FIG. 36, a cut-away view of a partially inflated center filled balloon 430 in a biological channel 560 is shown. Once placed, the balloon 420 may be expanded and the desired heat or temperature of the fluid 520 may be obtained for the desired period of time or effect. After deflation, the catheter 430 may be removed. In one embodiment, the catheter 430 may include an irrigation and/or suction lumen 580. The irrigation/suction lumen 580 may enable loose biological material, such as biological tissue 570 which has been partially or entirely destroyed, to be removed after the procedure without having to insert another instrument. The irrigation/suction lumen 580 also allows materials to be injected before, during, and/or after inflation of the balloon 420.

It should be recognized that while some features are discussed herein with respect to certain particular embodiments, such as some features associated with the end filled balloon catheter 404, they may be used in other embodiments, such as in the center filled balloon catheter 430, and vice versa. Thus, it will be appreciated that any of the embodiments discussed herein may include a feature which is shown in association with a different embodiment.

Figure 37:
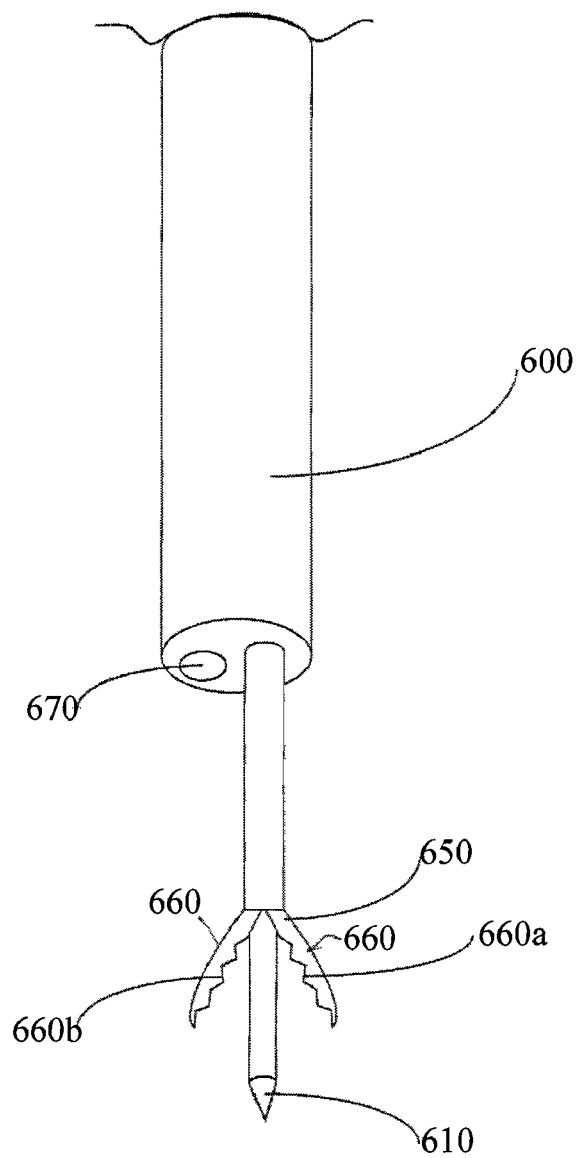
FIG. 37 shows a thermal surgical tool with a gripping mechanism and thermal surgical and sculpting tip.
Figure 38:
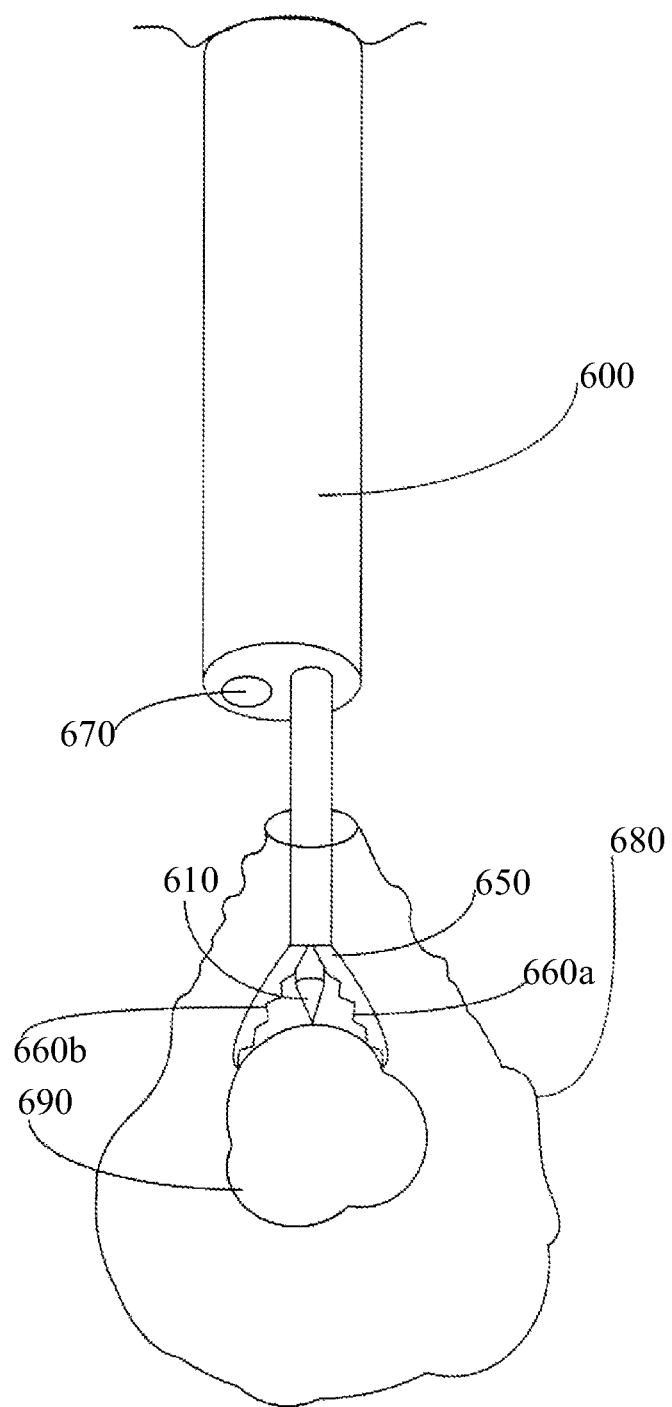
FIG. 38 shows a gall bladder, gall stone and thermal surgical tool.
Figure 39:
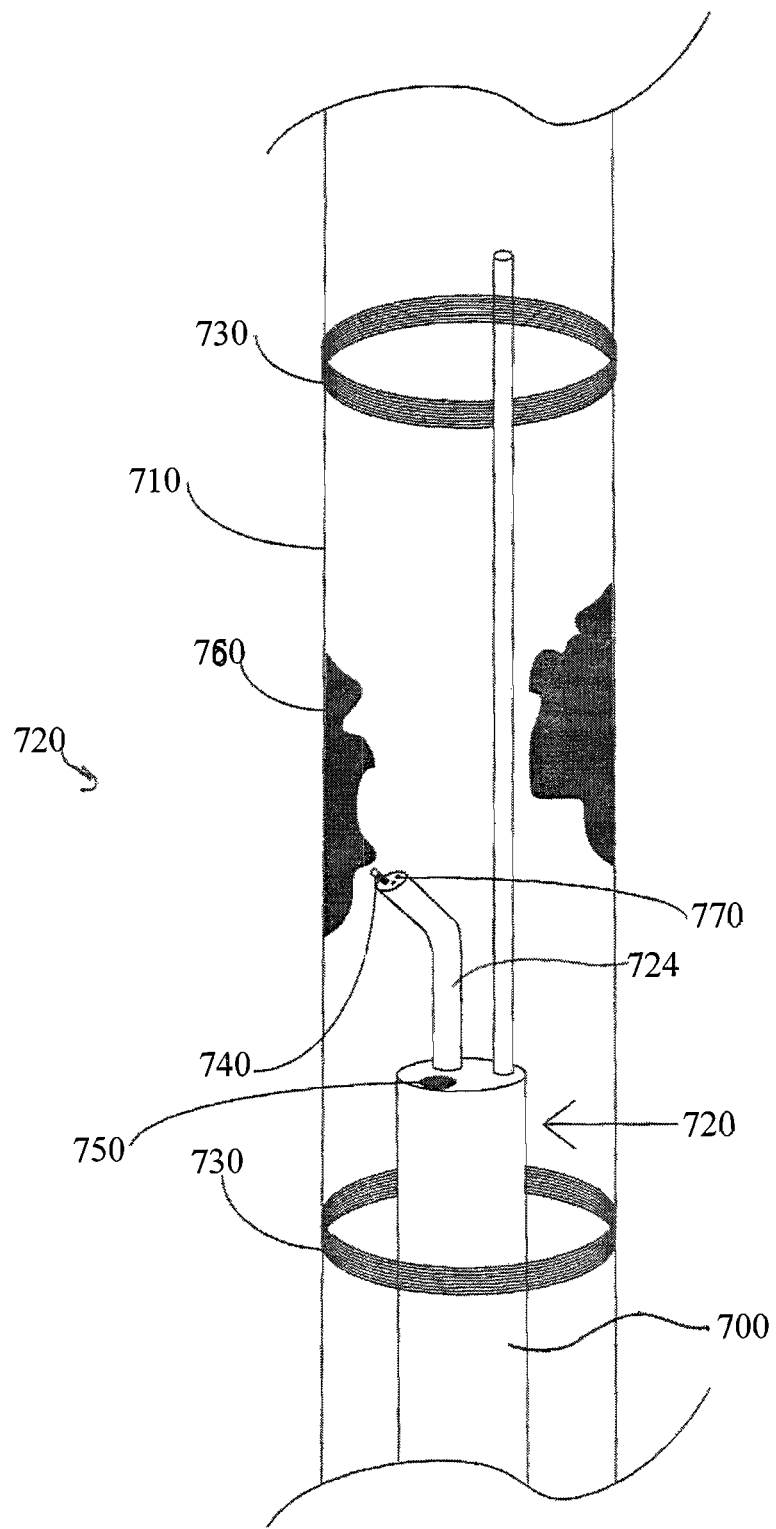
FIG. 39 shows an artery with a thermal removal system.

Turning now to FIGS. 37 through 39, alternate thermal surgical tools are shown which may also be used to alter biological material. For example, the thermal surgical tools shown in FIGS. 37 through 39 may be used to aid a body to remove blockages or disturbances by natural processes, smooth surfaces to prevent further damage, or even help surgeons remove biological material through small holes by altering the shape and/or state of the biological material.

Referring to FIG. 37, a surgical tool 600 with a thermal sculpting tip 610 is shown. The thermal sculpting tip 610 may include a thermal heating element, such as a ferromagnetic coated conductor to allow the thermal sculpting tip to be heated. The surgical tool 600 may be used to contour, shape, break up biological material, etc. For example, gall stones may be treated using the surgical tool 600 by breaking up or dissolving the gall stones. Where a gall bladder with gall stones is being removed from the body, larger gall stones may prevent the gall bladder from exiting a small incision. The surgeon may then crush the gall stones or make a larger incision to remove the gall bladder. Obviously, it is not preferred to make larger incisions. Thus, breaking up the stones may be preferred to make it easier for the gall bladder to pass through a small incision made in the body.

The surgical tool 600 may include one or more moveable arms 660 to form a gripping mechanism 650 as well as the thermal sculpting tip 610. The one or more moveable arms 660 forming the gripping mechanism 650 are disposed adjacent each other so as to allow for manipulation of a biological material. For example, the gripping mechanism 650 may be used to grip a gall stone during surgery. Where a gall bladder is being removed but will not easily pass through a small incision in the patient, thus, the surgical tool 600 may be used to break apart a gall stone in the gall bladder either mechanically or by the application of heat. Similarly, the surgical tool 600 may be used to grasp and destroy or sculpt other biological material.

According to another aspect of the invention, the edges 660a and 660b of the grasping mechanism 650 or arms 660 may have a ferromagnetically heated surgical edge such that the grasping mechanism 650 may be placed adjacent tissue or other material and then the thermal edges 660a, 660b activated to make a cut. The surgical tool 600 may include an optical system disposed in a port 670, such a camera or a lens attached to a fiber optic cable to view the surgery site. The port 670 may also be a fluid delivery passage used to insert or remove substances.

Referring to FIG. 38, an exemplary use of the surgical tool 600 to destroy gall stones is shown. The surgical tool 600 has been inserted into a gall bladder 680 containing a gall stone 690. The gall stone 690 may be grasped by the gripping mechanism 650 and the thermal surgical tip 610 may be deployed to cut, mechanically break or melt the gall stone 690. Thus, the gall stone's 690 size and/or state of matter may be changed (experimentation has shown that the gall stone 690 may be melted in many circumstances). After destruction of the gall stone 690, or a reduction in its size, the gall stone 690 as well as other contents of the gall bladder 680 may be removed through port 670. This allows the gall bladder 680 to be more easily removed from the body. By keeping a smaller surgical hole in the body, recovery time may be improved and scarring minimized. The surgical tool 600 may be similarly used to grasp other pieces of biological material to cut, reshape, or destroy the material.

Referring to FIG. 39, an artery 710 with a thermal removal system 720 is shown. In some cases, it may be beneficial to create an environment for the thermal surgical tool 700. In this case, a structure, such as a support structure 730, such as a balloon, retaining ring, ribs, etc., may be used to contain the surgical site and prevent undesired destruction or coagulation of the surrounding material. Fluid, such as blood, may be removed and, if needed, an alternate fluid may be inserted during the thermal procedure via port 750. The thermal surgical tip 740 may cut or melt the desired biological substance. The substance may then be removed and fluids replaced, if needed, and the support structures 730 may be retracted.

FIG. 39 shows an exemplary use of the thermal removal system 720. The thermal removal system 720 may include an endoscope or catheter 700 insertable into a blood vessel, artery, etc. which includes a plurality of ports or integrated tools. For example, a working thermal tool 724 or other tool may extend through one port for thermally shaping structures within the body.

One or more support structures 730 may be deployed in the blood vessel to secure the catheter 700 in place in the blood vessel, etc., and/or to isolate the area being worked on. Thus, for example, the support structures 730 may be disposed around a plaque 760 which needs to be removed. Using port 750, blood may be aspirated from the portion of artery 710 between the support structures 730 and replaced with some other solution so as to prevent coagulation of blood in the area where work is being performed.

A thermal surgical tip 740 of the thermal tool 724 may be inserted through or may be held in the catheter 700. The thermal surgical tip 740 may include, for example, a ferromagnetic coated conductor or other thermal tools and may be used to melt or cut away some or all of the plaque 760 which is restricting flow through the vessel. The portions of the plaque 760 which are cut away can then be removed through the port 750 with a tool or by simple aspiration. The thermal surgical tool 700 may also include an aspiration channel 770 within the working catheter or tool 724 which can be used to remove melted plaque 760 or provide other communication with the work area. If desired, the artery 710 may be flushed to ensure that all of plaque 760 is removed before retracting the support structures 730 and allowing blood flow to return.

Figure 40:
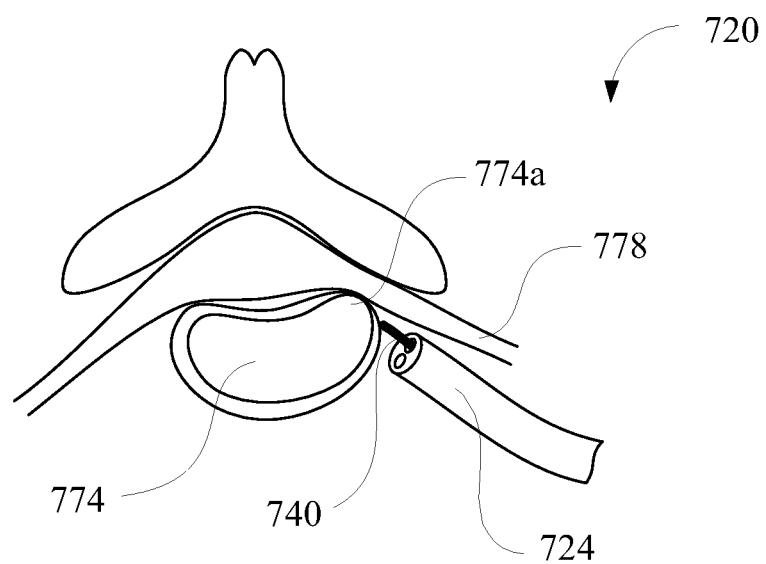
FIG. 40 shows a thermal surgical tool being used on a herniated spinal disc.

The thermal removal system 720 may also be used to perform a variety of surgical and/or therapeutic procedures. For example, the thermal removal system 720 may be used to sculpt biological material in a variety of contexts. In addition to the removal of plaque, the thermal removal system 720 may include a thermal tool 724 with a thermal tip 740 which can be used, for example to remove all or part of a herniated portion 774a of a spinal disk 774 as shown in FIG. 40. A herniated portion 774a of a disc 774 can extend into contact with a portion of the spinal nerve 778 and cause considerable pain in the back, arm or leg depending on which vertebrae is involved.

In accordance with one aspect of the present invention, the thermal tip 740 may be advanced into contact with the herniated portion 774a of the spinal disc 774 and use heat to ablate or cut away the herniated portion. The thermal tool may also seal off the location of the tissue removal on the disc to reduce the risk of complications.

While the thermal tip may use a number of thermal mechanisms, a thermal tip 740 formed from a ferromagnetic material in a manner similar to the multiple configurations discussed above, is advantageous because it can be configured to rapidly heat and, depending on its construction, can rapidly cool. This allows the surgeon to heat the tip as desired and then cool the tip and thereby reduce the risk of accidental injury to a nerve, etc. caused by a hot thermal tip 740.

Figure 41:
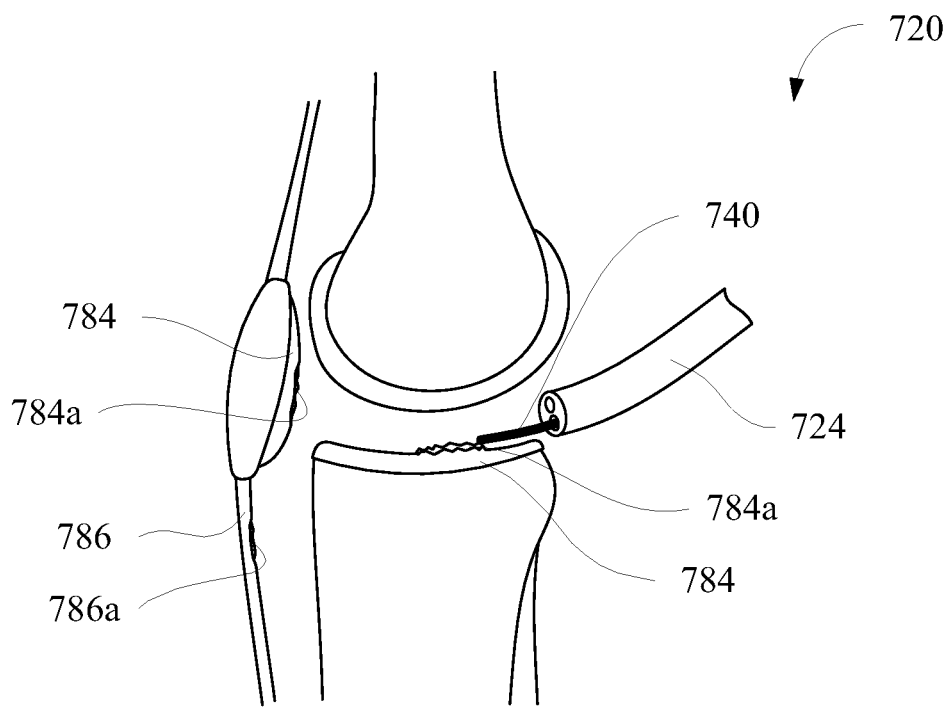
FIG. 41 shows a thermal surgical tool being used on cartilage in a knee.

It will be appreciated that there are number of other applications for a thermal tool as discussed herein. Other uses may include, without limitation, sculpting cartilage in the knee such that tears or rough portions on tendons or cartilage in the knee may be smoothed, as shown in FIG. 41. A thermal system 720 may involve a tool 724, such as a catheter, endoscope or electrosurgical knife which can be inserted into a knee joint. A thermal tip 740 may be brought into contact with cartilage 784 or a tendon 786 to smooth out a rough or torn portion 784a, 786a. The heat of the thermal tip 740 can be used to cut or otherwise shape the rough or torn cartilage or tendon. By smoothing the rough portion 784a, 786a of the cartilage or tendon, the interaction with other anatomical structures may be more regular, reducing the risk of the structures catching and causing more damage and/or the discomfort of the person.

In the alternative, the thermal removal systems discussed herein may also be used during liposuction. The thermal tip 740 or other thermal structure discussed above may be activated to melt and remove fat in conjunction with an aspiration device. One of skill in the art will appreciate that uses for the thermal removal system 720 described herein are only illustrative and many uses will be apparent in light of the present disclosure.

It will be appreciated that while the word melt was used for discussing a state change of materials, the thermal surgical tool may be used to change the phase of the biological material, such as sublimate or vaporize the biological material. Likewise, the thermal tool can be used to simply cut away tissue.

It will be appreciated that the thermal surgical tool or system in accordance with the present invention will have a wide variety of uses. Not only can the tools be used on humans they can also be used to treat other animals, such as in the context of veterinarian procedures. The tools may also be used ex vivo to cut tissues or biomaterials, such as those used for implantation, into smaller pieces for other uses.

Certain embodiments of the surgical system may have broad application within surgery as well. A loop geometry may have advantages in cutting, coagulation and biopsy applications. A blade geometry may have advantages for cutting and hemostasis applications. The point geometry may have advantages in dissection and coagulation applications, and in particular, neurodissection and coagulation. Moreover, the application using a particular geometry may be made more precise by altering the diameter, length, material characteristics, and/or other characteristics discussed above.

While the present invention has been described principally in the area of surgical tools and the treatment of live tissue (though it can be used on dead tissue as well), it will be understood that a tool made in accordance with the present invention and the methods discussed herein may have other uses.

Other uses of the instruments discussed herein will be understood by those skilled in the art in light of the present description. In accordance with one aspect of the present invention, a surgical tool may include a balloon catheter comprising a catheter body having a first end and a second end and comprising a channel and an opening; a balloon forming a chamber, the chamber in fluid communication with the opening in the catheter body; and a thermal element disposed in communication with the balloon for heating fluid passing through the channel and/or located in the balloon. The balloon catheter of may include the thermal element comprising a conductor at least partially covered with ferromagnetic material; the balloon forming a chamber disposed at the first end of the catheter body and the balloon expanding longitudinally and laterally away from the first end of the catheter; the balloon forming a chamber is disposed between the first end and the second end of the catheter body; the expanded balloon substantially conforming to the shape of a biological structure; the thermal element being substantially disposed in the channel of the catheter body, with a fluid in communication with the thermal element being directed into the chamber of the balloon through the channel in the catheter body to thereby heat the fluid; at least a portion of the thermal element being disposed in the balloon to thereby maintain the temperature of a fluid contained in the chamber; a sensor disposed on the catheter body; a plurality of sensors, wherein at least one of the plurality of sensors is configured to extend away from the catheter body; at least one of the plurality of sensors monitors a characteristic of a biological structure selected from the group consisting of temperature, tissue color, and electrical properties; the catheter body further comprising a plurality of channels, and wherein the plurality of channels allows a fluid to circulate into and out of the chamber of the balloon; fluid circulation being regulated by a pump disposed on the catheter; and/or fluid being introduced into the chamber of the balloon under pressure and fluid circulation is regulated by a valve, or combinations thereof.

A method for treating tissue in accordance with the present invention may include selecting a catheter having a balloon attached thereto and a thermal element disposed therealong; and passing fluid through the catheter and into the balloon; wherein the fluid is brought into contact with the thermal element to heat the fluid. The method may also include selecting a catheter having a ferromagnetic thermal element disposed therein; and/or heating the fluid as it passes through the catheter, or combinations thereof.

A thermally adjustable surgical tool comprising in accordance with the present invention may include an electrical conductor, a ferromagnetic coating covering at least a portion of the electrical conductor; and one or more moveable arms, wherein the one or more moveable arms are disposed adjacent each other so as to allow for manipulation of a biological material. The surgical tool may also include the one or arms being used to grasp the biological material; at least one arm of the one or more arms comprising a portion of which is coated with a ferromagnetic material; the at least one arm being configured to cut the biological material when the at least one arm is adjacent to the biological material by supplying power to the thermally adjustable surgical tool such that the temperature of the ferromagnetic material substantially increases; a catheter body having a lumen, and wherein the lumen is configure to remove the biological material from a surgical site; a sensor configured to detect tissue properties proximate to the ferromagnetic coating or the one or more arms; the sensor comprising an optical system for viewing a site, and wherein the site is located substantially adjacent to where the biological material is manipulated; and/or the optical system being selected from the group consisting of a camera and a lens attached to a fiber optic cable, or combinations thereof.

A thermal shaping system according to the present invention may include a thermally adjustable surgical tool having an electrical conductor and a ferromagnetic coating covering at least a portion of the electrical conductor and a support structure, wherein the ferromagnetic coating is configured to treat a biological material at a site, and wherein the support structure is configured to substantially maintain a defined area at the site where the biological material is treated. The system may also include a catheter body having a lumen for aspirating a fluid from the site or introducing a fluid into the site; a support structure deployable from the thermally adjustable surgical tool and configured to be positioned adjacent the site; and/or the lumen being configured to aspirate blood from the site and then introduce a fluid, other than blood, into the site prior to treating a biological material, or combinations thereof.

A surgical tool in accordance with the present invention may include a catheter, a tool extendable from the catheter, the tool having a thermal element disposed therein; and at least one arm disposed to engaged tissue and hold the tissue adjacent the thermal element. The tool may also include a plurality of arms; and/or the thermal element being disposed on at a thermal tip and wherein the at least one arm has a thermal surface, or combinations thereof.

A surgical tool in accordance with the invention may include a catheter; a plurality of support structures disposed in communication with the catheter; and a thermally adjustable tool disposal between the support structures. The tool may also include a ferromagnetic thermal element; the support structure comprising balloons.

A method of treating biological material in accordance with the present invention may include selecting a thermally adjustable surgical tool having a ferromagnetic heating element, placing the ferromagnetic heating element adjacent the biological material; and delivering power to the ferromagnetic heating element to heat the ferromagnetic heating element and thereby treat the biological material. The method may also include selecting a thermally adjustable surgical tool having a ferromagnetic heating element comprises selecting a catheter having a balloon and a ferromagnetic heating element disposed along the catheter so as to heat fluid used to fill the balloon; directing a fluid through the catheter and into the balloon and heating the fluid with the ferromagnetic heating element; the ferromagnetic heating element comprising a ferromagnetic coated conductor substantially disposed in a channel of the catheter body, and wherein the fluid is directed into the chamber of the balloon via the channel and passes by the ferromagnetic coated conductor so as to heat the fluid; disposing at least a portion of the ferromagnetic coated conductor between the catheter and the balloon to thereby maintain the temperature of the fluid contained in the chamber; selecting a catheter having at least at least one sensor disposed thereon; selecting a catheter having at least one sensor on a surface of the balloon and disposing the balloon such that the at least one sensor extends away from the catheter body when a fluid is directed into the chamber of the balloon; at least one sensor extending to a position adjacent a surface of a biological structure; the catheter comprising a plurality of channels, and wherein the method further comprises the step of circulating the fluid into the balloon through one channel and out of the balloon through another channel; disposing a pump on the catheter to regulate fluid circulation into and out of the balloon; directing the fluid into the chamber of the balloon under pressure and regulating fluid circulation in the balloon using a valve; at least one moveable arm disposed so as to allow for manipulation of a biological material. using the at least one arm to grasp the biological material; the step of coating a portion of the at least one arm with a ferromagnetic material; the step of cutting the biological material with the at least one arm coated with a ferromagnetic material; the step of selecting a thermally adjustable surgical tool comprising a catheter body having a lumen, and removing the biological material from a surgical site through the lumen after the biological material is manipulated; the step of disposing an optical system on the thermally adjustable surgical tool for viewing a surgical site located substantially adjacent to where the biological material is manipulated; melting the biological material using the ferromagnetic heating element; the step of attaching a deployable support structure to the thermally adjustable surgical tool, wherein the deployable support structure substantially maintains a surgical site where the tissue is being treated; the step of selecting a thermally adjustable surgical tool which comprises a catheter body having a lumen, and aspirating a fluid from the surgical site or introducing a fluid into the surgical site via the lumen; the step of aspirating a fluid comprising blood from the surgical site, and introducing a fluid other than blood into the surgical site prior to treating a biological material; the step of flushing the surgical site with a fluid; and/or the step of flushing the surgical site by delivering a fluid to the surgical site via the lumen after to the biological material has been treated, or combinations thereof.

There is thus disclosed an improved heated balloon catheter. It will be appreciated that numerous changes may be made to the present invention without departing from the scope of the claims. The appended claims are intended to cover such modifications.

What is claimed is:

1. A balloon catheter comprising:
a catheter body having a first end and a second end and comprising at least one channel and an opening;
a balloon forming a chamber, the chamber in fluid communication with the opening in the catheter body; and
a thermal element disposed in communication with the balloon for heating fluid, the thermal element comprising a ferromagnetic heating element in the form of a ferromagnetic coil.

2. The balloon catheter of claim 1, wherein the ferromagnetic coil comprises a conductor at least partially covered with ferromagnetic material.

3. The balloon catheter of claim 1, the balloon forming the chamber is disposed at the first end of the catheter body and wherein the balloon is configured to be expandable longitudinally and laterally away from the first end of the catheter body.

4. The balloon catheter of claim 1, wherein the balloon forming the chamber is disposed between the first end and the second end of the catheter body.

5. The balloon catheter of claim 1, wherein the balloon is inflatable and is configured to substantially conform to a shape of a biological structure when inflated.

6. The balloon catheter of claim 1, further comprising the fluid disposed in the balloon, wherein the thermal element is substantially disposed in the at least one channel of the catheter body, and wherein the fluid is disposed in communication with the thermal element to thereby heat the fluid and is directed into the chamber of the balloon through the at least one channel in the catheter body.

7. The balloon catheter of claim 1, further comprising fluid disposed in the balloon, the fluid having a temperature, and wherein at least a portion of the thermal element is disposed in the balloon to thereby maintain the temperature of the fluid contained in the chamber.

8. The balloon catheter of claim 1, further comprising a sensor disposed on the catheter body.

9. The balloon catheter of claim 1, further comprising a plurality of sensors, wherein at least one of the plurality of sensors is configured to extend away from the catheter body.

10. The balloon catheter of claim 9, wherein the at least one of the plurality of sensors is configured to monitor a characteristic of a biological structure selected from the group consisting of temperature, tissue color, and electrical properties.

11. The balloon catheter of claim 1, wherein the at least one channel comprises a plurality of channels, and wherein the plurality of channels are configured to allow the fluid to circulate into and out of the chamber of the balloon.

12. The balloon catheter of claim 11, wherein circulation of the fluid is regulated by a pump disposed on the catheter body.

13. The balloon catheter of claim 11, wherein the fluid is introduced into the chamber of the balloon under pressure and circulation of the fluid is regulated by a valve.

14. A method for treating biological material, the method comprising:
selecting a catheter body having a fluid channel, a balloon disposed along the catheter body in fluid communication with the fluid channel, and a ferromagnetic heating element disposed so as to be in contact with the fluid contained within the balloon catheter for heating the fluid, wherein the ferromagnetic heating element comprises a ferromagnetic coil;
passing fluid through the catheter body and into the balloon; wherein the fluid is brought into contact with the thermal element to heat the fluid; and
contacting the biological material with the balloon.

15. The method according to claim 14, wherein the method comprises heating the fluid as it passes through the catheter body.

16. A balloon catheter comprising:
a catheter body having a fluid channel;
a balloon disposed along the catheter body in fluid communication with the fluid channel; and
a ferromagnetic heating element disposed so as to be in contact with fluid contained within the balloon catheter for heating the fluid, wherein the ferromagnetic heating element comprises a ferromagnetic coil.

17. The balloon catheter of claim 16, further comprising a sensor disposed in the balloon catheter.

18. The balloon catheter of claim 17, wherein the balloon catheter has the fluid disposed therein and further comprising a temperature sensor for monitoring temperature of the fluid in the fluid channel.

19. The balloon catheter of claim 16, wherein the balloon is sufficiently clear to conduct a visual color check of tissue adjacent to the balloon.

20. The balloon catheter of claim 16, wherein the ferromagnetic coil is disposed in the balloon catheter.

21. The balloon catheter of claim 16, wherein the ferromagnetic coil is disposed in the balloon.

22. The balloon catheter of claim 16, further comprises a valve positioned to regulate circulation of the fluid in the balloon.

23. The balloon catheter of claim 16, wherein the balloon is defined by an outer wall and further comprising a plurality of sensors disposed on the outer wall of the balloon.

24. The balloon catheter of claim 16, wherein the balloon is shaped to conform to a body part when inflated.

25. The balloon catheter of claim 24, wherein the balloon is shaped to substantially fill a uterus when inflated.

26. The balloon catheter of claim 16, further comprising at least one sensor extendable into the balloon and deployable independent of the balloon.

27. The balloon catheter of claim 2, wherein the at least one sensor comprises a plurality of sensors which are deployable separately from the balloon.

* * * * *